United States Patent
Ruiz Echevarria et al.

(10) Patent No.: US 12,146,139 B2
(45) Date of Patent: Nov. 19, 2024

(54) OLIGONUCLEOTIDE INTERFERENCE TREATMENTS OF PROSTATE CANCER

(71) Applicant: The Board of Regents of the University of Oklahoma, Norman, OK (US)

(72) Inventors: Maria Jesus Ruiz Echevarria, Edmond, OK (US); Joshua Moses Corbin, Oklahoma City, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 0 days.

(21) Appl. No.: 17/441,895

(22) PCT Filed: Nov. 16, 2020

(86) PCT No.: PCT/US2020/060753
§ 371 (c)(1),
(2) Date: Sep. 22, 2021

(87) PCT Pub. No.: WO2021/097437
PCT Pub. Date: May 20, 2021

(65) Prior Publication Data
US 2022/0275374 A1  Sep. 1, 2022

Related U.S. Application Data

(60) Provisional application No. 62/935,521, filed on Nov. 14, 2019.

(51) Int. Cl.
*C12N 15/113* (2010.01)
*A61P 35/00* (2006.01)

(52) U.S. Cl.
CPC .......... *C12N 15/1138* (2013.01); *A61P 35/00* (2018.01); *C12N 2310/11* (2013.01); *C12N 2310/122* (2013.01); *C12N 2310/14* (2013.01); *C12N 2310/531* (2013.01)

(58) Field of Classification Search
CPC ............ C12N 15/1138; C12N 2310/11; C12N 2310/122; C12N 2310/14; C12N 2310/531; C12N 2310/20; A61P 35/00
See application file for complete search history.

(56) References Cited

U.S. PATENT DOCUMENTS

| | | |
|---|---|---|
| 2002/0081577 A1 | 6/2002 | Kilkuskie et al. |
| 2006/0240554 A1* | 10/2006 | Chen ........................ A61P 31/08 435/375 |
| 2018/0251762 A1 | 9/2018 | Peter et al. |
| 2018/0320187 A1 | 11/2018 | Peter et al. |
| 2021/0054383 A1* | 2/2021 | Hagedorn .......... C12N 15/1138 |

FOREIGN PATENT DOCUMENTS

| | | | |
|---|---|---|---|
| WO | 2003072705 A2 | 9/2003 | |
| WO | WO-2010007522 A1 * | 1/2010 | ......... A61K 31/7088 |
| WO | 2012135736 A2 | 10/2012 | |
| WO | WO-2013166004 A2 * | 11/2013 | ........... A61K 31/713 |

OTHER PUBLICATIONS

Ostling, P., et al.; "Systematic Analysis of MicroRNAs Targeting the Androgen Receptor in Prostate Cancer Cells"; Cancer Res 71:5 (2011) 1956-1967.
Shen, J., et al.; "Dysregulation of Circulating MicroRNAs and Prediction of Aggressive Prostate Cancer"; Prostate 72:13 (2012) 1469-1477.
Galio, L., et al.; "Ovis aries uncharacterised small RNA, clone P3A6"; GenBank HE599875.1; 2013; 1 page.
Hydrbring, P., et al.; "Clinical applications of microRNAs"; F1000Research 2:136 (2013) 16 pages.
Lewis, H., et al.; "miR-888 is an expression prostatic secretions-derived microRNA that promotes prostate cell growth and migration"; Cell Cycle 13:2 (2014) 227-239.
Toropainen, S., et al.; "SUMO ligase PIAS1 functions as a target gene selective androgen receptor coregulator on prostate cancer cell chromatin"; Nucleic Acids Research (2014) 14 pages.
Fujiwara, N., et al.; "miR-634 Activates the Mitochondrial Apoptosis Pathway and Enhances Chemotherapy-Induced Cytotoxicity"; Cancer Res 75:18 (2015) 3890-3901.
Wang, T., et al.; Identification and characterization of essential genes in the human genome; Science 350:6264 (2015) 1096-1101.
Coarfa, C., et al.; "Comprehensive proteomic profiling identifies the androgen receptor axis and other signaling pathways as targets of microRNAs suppressed in metastatic prostate cancer"; Oncogene 35:18 (2016) 2345-2356.
GenBank submission HE599875.1, Ovis aries uncharacterised small RNA, clone P3A6, Jan. 4, 2013 [online]. [Retrieved on Apr. 1, 2021]. Retrieved from the internet: <URL: https://www.ncbi.nlm.nih.gov/nuccore/HE599875>Entire document.
Depriest, A.D., et al.; "Regulators of Androgen Action Resource: a one-stop shop for the comprehensive study of androgen receptor action"; Database (2016) 1-11.

(Continued)

*Primary Examiner* — J. E. Angell
(74) *Attorney, Agent, or Firm* — Hall Estill Law Firm

(57) ABSTRACT

Interfering nucleic acids and methods of their use in treat prostate cancers, such as aggressive prostate cancers. The nucleic acids may be, for example, short interfering RNA (siRNA), short hairpin RNA (shRNA), antisense RNA, antisense DNA, Chimeric Antisense DNA/RNA, and microRNA (miRNA) oligonucleotides. The oligonucleotide has a seed sequence that is complementary to a sequence of either a gene or an mRNA encoding an androgen receptor (AR) coregulator or a fragment thereof having AR coregulator activity. The nucleic acid compound may have a non-natural modification in the oligonucleotide, and/or an organic moiety conjugated to the oligonucleotide. The oligonucleotide has inhibitory activity against the expression or biological activity of the AR coregulator.

26 Claims, 13 Drawing Sheets
Specification includes a Sequence Listing.

(56) References Cited

OTHER PUBLICATIONS

Wilting, S.M., et al.; "Aberrant methylation-mediated silencing of microRNAs contributes to HPV-induced anchorage independence"; Oncotarget 7:28 (2016) 43805-43819.

Chakraborty, C., et al.; "Therapeutic miRNA and siRNA: Moving from Bench to Clinic as Next Generation Medicine"; Molecular Therapy: Nucleic Acids 8 (2017) 132-143.

Fei, T., et al.; "Genome-wide CRISPR screen identifies HNRNPL as a prostate cancer dependency regulating RNA splicing"; PNAS (2017) ES207-ES215.

Ivkovic, T.C., et al.; "microRNAs as cancer therapeutics: A step closer to clinical application"; Cancer Letters 407 (2017) 113-122.

Putzbach, W., et al.; "Many si/shRNAs can kill cancer cells by targeting multiple survival genes through an off-target mechanism"; eLife (2017) 1-43.

Zhou, Y., et al.; "TEAD1/4 exerts oncogenic role and is negatively regulated by miR-4269 in gastric tumorigenesis"; Oncogene 36 (2017) 6518-6530.

Gao, Q.Q., et al.; "6mer seed toxicity in tumor suppressive microRNAs"; Nature Communications 9:4504 (2018) 1-16.

Hasegawa, T., et al.; "Characterization and Evidence of the miR-888 Cluster as a Novel Cancer Network in Prostate"; Mol Cancer Res 16:4 (2018) 669-681.

Mizoguchi, A., et al.; "MicroRNA-8073: Tumor suppressor and potential therapeutic treatment"; PLOS One (2018) 1-15.

Chen, D., et al.; "MircroRNA-634 functions as a tumor suppressor in pancreatic cancer via directly targeting heat shock-related 70-kDa protein 2"; Experimental and Therapeutic Medicine 17 (2019) 3949-3956.

Fernandes, R.C., et al.; "Interplay between the androgen receptor signaling axis and microRNAs in prostate cancer"; Endrocine-Related Cancer 26:5 (2019) R237-R257.

Hanna, J., et al.; "The Potential for microRNA Therapeutics and Clinical Research"; Frontiers in Genetics 10:478 (2019) 1-6.

Hu. C.-Y., et al.; "MiR-506-3p acts as novel tumor suppressor in prostate cancer through targeting GALNT4"; Eur Rev Med Pharmacol Sci 23 (2019) 5133-5138.

Kiener, M., et al.; "miR-221-5p regulates proliferation and migration in human prostate cancer cells and reduces tumor growth in vivo"; BMC Cancer 19:627 (2019) 1-17.

Liu, K., et al.; "Prognostic value of miR-221 in human malignancy: evidence from 3041 subjects"; BMC Cancer 19:867 (2019) 1-10.

Wu, X., et al.; "lncRNA SNHG20 promotes prostate cancer migration and invastion via targeting the miR-6516-5p/SCGB2A1 axis"; am J Transl Res 11:8 (2019) 5162-5169.

Qi, J., et al.; "EIF3J-AS1 promotes glioma cell growth via up-regulating ANXA11 through sponging miR-1343-3p"; Cancer Cell Int 20:428 (2020) 1-13.

Gokita, K., et al.; "Therapeutic Potential of LNP-Mediated Delivery of miR-634 for Cancer Therapy"; Molecular Therapy: Nucleic Acids 19 (2019) 330-338.

Wang, L., et al.; "Exosome-transferred LINC01559 promotes the progression of gastric cancer via PI3K/AKT signaling pathway"; Cell Death and Disease 11:273 (2020) 1-14.

Zenner, M.L., et al.; "Oncogenic and tumor-suppressive microRNAs in prostate cancer"; Current Opinion in Endocrine and Metabolic Research 10 (2020) 50-59.

Corbin, J.M., et al.; "Seed-mediated RNA interference of androgen signaling and survival networks induces cell death in prostate cancer cells"; Molecular Therapy: Nucleic Acids 24 (2021) 337-351.

Javed, Z., et al.; "Targeting androgen receptor signaling with MicroRNAs and Curcumin: a promising therapeutic approach for Prostate Cancer Prevention and intervention"; Cancer Cell Int 21:77 (2021) 1-13.

PCT/US2020/060753; "International Search Report and Written Opinion"; dated Apr. 27, 2021; 12 pages.

EP20887785; "Supplementary Partial European Search Report"; European Patent Office; dated Jan. 17, 2024; 13 pages.

Toropainen, S., et al.; "SUMO legase PIAS1 functions as a target gene selective androgen receptor coregulator on prostate cancer cell chromatin"; Nucleic Acids Research (2014) 1-14.

PCT/US2020/060753; "International Preliminary Report on Patentability"; International Bureau of WIPO; dated May 17, 2022; 7 pages.

\* cited by examiner shScramble
 shL3
 shTMEFF2-3
 shTMEFF2-9

OLIGONUCLEOTIDE INTERFERENCE TREATMENTS OF PROSTATE CANCER

CROSS-REFERENCE TO RELATED APPLICATIONS

The present application is a national stage application of a PCT application having International Application No. PCT/US2020/060753, filed Nov. 16, 2020, which claims priority to U.S. Provisional Application having U.S. Ser. No. 62/935,521, filed Nov. 14, 2019, which claims the benefit under 35 U.S.C. 119(e), the disclosure of which is hereby expressly incorporated herein by reference.

SEQUENCE LISTING

The instant application contains a Sequence listing which has been submitted electronically in ASCII format and is hereby incorporated by reference in its entirety. Said ASCII copy, created Dec. 21, 2020, is named 820233-02507_Corrected_SEQ_LISTING_ST25.txt and is 46,849 bytes in size.

BACKGROUND

Ribonucleic acid interference (RNAi) via small interfering ribonucleic acids (siRNA) and short hairpin RNAs (shRNA) is a useful tool for knocking-down messenger RNA (mRNA) expression and studying gene function. Both siRNA and shRNA utilize the evolutionarily conserved microRNA (miRNA) gene regulatory process to decrease targeted mRNA expression. In short, after shRNA processing by the endogenous miRNA processing enzymes, one strand of the resulting mature double stranded RNA is loaded onto the RNA-induced silencing complex (RISC). Similar to endogenous mature miRNAs, the loaded RNA guides RISC to target transcripts via sequence complementarity, resulting in subsequent transcript degradation and/or translation inhibition. The RNA strand that is intended to guide RISC to the desired target transcript is called the guide strand, while the complementary strand is called the passenger. The seed sequence, nucleotides 2-7, on the 5' end of the mature guide strand is the most important sequence for determining RISC transcript targeting. It has been found that, like miRNAs, numerous transcripts can be targeted by a single sh/siRNA via seed sequence complementarity, especially to the three-prime untranslated region (3' UTR) of target transcripts, often resulting in undesired off target effects (OTEs). For this reason, numerous strategies have been developed to determine whether RNAi-induced phenotypes are generated by knocking-down the target gene of interest or off target transcripts. These strategies include: the use multiple independent RNAi target sequences, and demonstration of phenotypic recovery using recombinant overexpression of the target gene. The discovery of alternate knockdown/knockout methods, such as the potent CRISPR Cas9 system, has also aided researchers in the study of gene function.

Prostate cancer (PCa) is a major public health concern, as it remains the most commonly diagnosed non-skin malignancy and the second leading cause of cancer related deaths in men. The androgen signaling is essential for cell growth, differentiation and survival during prostate development, homeostasis and cancer progression. This dependency is exploited in PCa therapy with androgen deprivation therapy and targeted androgen receptor (AR) inhibitors. While these therapies are initially beneficial, the majority of patients eventually relapse with a resistant and lethal form of the disease called castration-resistant PCa (CRPC). In most cases, CRPC cells retain AR expression and remain dependent on its activity for growth and survival, and adaptations, such as, increased AR coregulator expression, AR amplification and/or mutation and constitutively AR splice variants that lack ligand binding, such as AR variant 7 (AR-V7), allow PCa cells to tolerate and grow in the androgen depleted environment. However, in an increasing subset of patients, CRPC cells lose AR expression and gain complete independence from AR transcriptional activity for growth and survival. Currently, the poor prognosis for patients with AR positive and AR negative CRPC underscores the need for the development of novel therapeutic agents and strategies. It is to such a need that the present disclosure is directed.

BRIEF DESCRIPTION OF THE DRAWINGS

FIG. 2A-D results demonstrate that TMEFF2-targeted shRNA mediated low androgen signaling phenotype is disconnected from TMEFF2 expression.

DETAILED DESCRIPTION

Figure 1A:
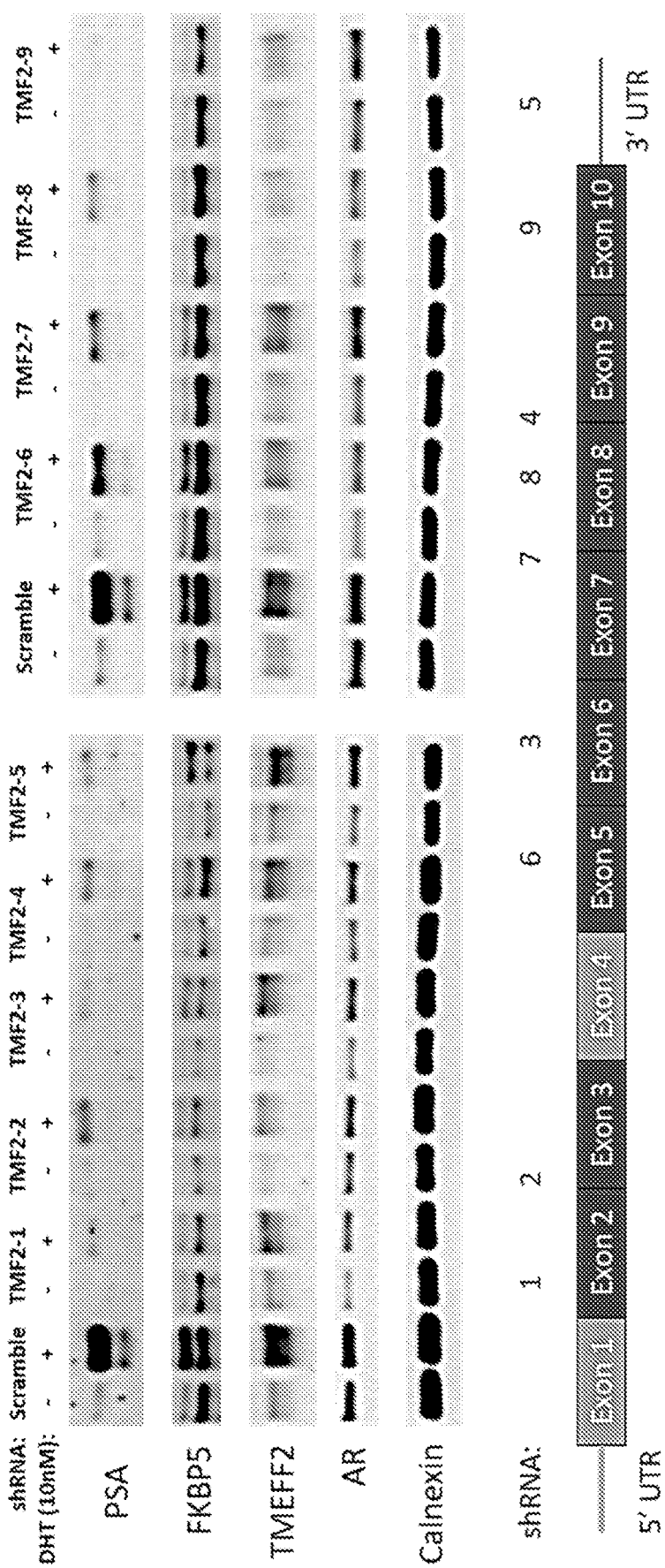
FIG. 1A shows Western blot analysis of nine independent shRNAs targeting 8 of 10 exons and 3'UTR of the TMEFF2 transcript. The schematic bar in the lower panel indicates targeted exon were exons 2, 3, and 5-10 and that untargeted exons were exons 1 and 4. Numbers above the bar indicate the corresponding shRNA name. shScramble control shRNA were transduced into LNCaP cells. Western blot analysis shows the levels of TMEFF2 (target gene), AR, and two androgen responsive proteins, PSA and FKBP5. Cells were grown in the presence and absence of 10 nM DHT for 24 hours to test androgen response. Calnexin was used as a loading control. Multiple shRNAs targeting TMEFF2 reduce AR and androgen responsive protein levels in LNCaP and 22Rv1 PCa cell lines.

The present disclosure is directed to a novel therapeutic strategy for treating prostate cancer (PCa) that relies on large-scale RNA interference (RNAi) of a network of androgen receptor (AR) coregulators. RNA interference (RNAi) is a biological mechanism to modulate gene expression which is mediated by small RNA molecules that recognize and bind to target mRNA(s) of specific genes thereby inhibiting their expression or promoting their degradation. The present work shows that certain small RNAs can inhibit networks of androgen receptor (AR) co-regulators, promoting growth inhibition and death of PCa cells, which depend on the activity of the AR and its coregulators to grow. This death mechanism is specific to cancer cells and does not affect viability of normal cells, and can kill PCa cells that have become resistant to conventional therapies. As further shown below, this disclosure relates to the therapeutic use of toxic small RNAs to kill prostate cancer cells via RNAi of networks of AR-coregulators.

Death Induced by Survival gene Elimination (DISE) is a process in which certain small interfering ribonucleic acids (siRNAs) or short hairpin ribonucleic acids (shRNAs) induce toxicity specifically in transformed cells through off-target seed region complementarity to the three-prime untranslated region (3' UTR) of essential survival genes, resulting in reduced expression. Paradoxically, DISE was identified using shRNA derived from the CD95/CD95L tumor suppressor and subsequently observed using shRNAs from several other tumor suppressors. We hypothesized that a DISE mechanism targeting genes that are regulated by androgen signaling is relevant to PCa. Consequently we have demonstrated that RNAi to the transmembrane protein with EGF like and two follistatin like domains 2 (TMEFF2), an androgen regulated tumor suppressor gene with restricted expression to adult brain and prostate, triggers a DISE-like mechanism in PCa cells. The present disclosure shows that certain shRNAs targeted to TMEFF2 inhibit androgen signaling and are toxic to prostate cancer (PCa) cells through a similar off-target seed mediated mechanism that also targets androgen signaling regulatory genes, resulting in potent inhibition of androgen mediated transcriptional response and cell death. We call this PCa-specific DISE-like mechanism the Androgen Network-DISE (AN-DISE). Importantly, AN-DISE effectively kills castration resistant PCa (CRPC) cells that arise as a consequence of conventional therapies targeting androgen signaling. Given the sensitivity of CRPC cells, and the general toxicity of essential gene depletion in cancer cells, AN-DISE provides a useful strategy for treating prostate cancer, particularly CRPC.

Before further describing various embodiments of the compounds, compositions, and methods of the present disclosure in more detail by way of exemplary description, examples, and results, it is to be understood that the compounds, compositions, and methods of present disclosure are not limited in application to the details of specific embodiments and examples as set forth in the following description. The description provided herein is intended for purposes of illustration only and is not intended to be construed in a limiting sense. As such, the language used herein is intended to be given the broadest possible scope and meaning; and the embodiments and examples are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the present disclosure. However, it will be apparent to a person having ordinary skill in the art that the present disclosure may be practiced without these specific details. In other instances, features which are well known to persons of ordinary skill in the art have not been described in detail to avoid unnecessary complication of the description. It is intended that all alternatives, substitutions, modifications and equivalents apparent to those having ordinary skill in the art are included within the scope of the present disclosure. While the compounds, compositions, and methods of the present disclosure have been described in terms of particular embodiments, it will be apparent to those of skill in the art that variations may be applied to the compounds, compositions, and methods and in the steps or in the sequence of steps of the methods described herein without departing from the concept, spirit, and scope of the inventive concepts.

All patents, published patent applications, and non-patent publications mentioned in the specification or referenced in any portion of this application, including the priority document U.S. Provisional patent application Ser. No. 62/935, 521, filed on Nov. 14, 2019, are herein expressly incorporated by reference in their entirety to the same extent as if each individual patent or publication was specifically and individually indicated to be incorporated by reference.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular. Where used herein, the specific term "single" is limited to only "one".

As utilized in accordance with the methods, compounds, and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, includes ranges of 1-20, 10-50, 50-100, 100-500, and 500-1,000, for example. Reference to an integer with more (greater) or less than includes any number greater or less than the reference number, respectively. Thus, for example, reference to less than 100 includes 99, 98, 97, etc. all the way down to the number one (1); and less than 10 includes 9, 8, 7, etc. all the way down to the number one (1). A strand length in a range of 12 to 50 nucleotides refers to an oligonucleotide having at least 12 nucleotides and less than 51 nucleotides, and includes any range bounded by two different integers in said range of 12, 13, 14, 15, 16, 17, 18, 19, 21, 22, 23, 24, 25, 26, 27, 28, 29, 30, 31, 32, 33, 34, 35, 36, 37, 38, 39, 40, 41, 42, 43, 44, c 45, 46, 47, 48, 49, and 50 nucleotides, including for example 18 to 25, 20 to 24, or 20-22.

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the terms "about" or "approximately" are used to indicate that a value includes the inherent variation of error in the disclosed embodiments, or the variation that exists among the study subjects. As used herein the qualifiers "about" or "approximately" are intended to include not only the exact value, amount, degree, orientation, or other qualified characteristic or value, but are intended to include some slight variations due to measuring error, manufacturing tolerances, stress exerted on various parts or components, observer error, wear and tear, and combinations thereof, for example. The term "about" or "approximately", where used herein when referring to a measurable value such as an amount, a temporal duration, and the like, is meant to encompass, for example, variations of ±20% or ±10%, or ±5%, or ±1%, or ±0.1% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein any reference to "one embodiment" or "an embodiment" means that a particular element, feature, structure, or characteristic described in connection with the embodiment is included in at least one embodiment and may be included in other embodiments. The appearances of the phrase "in one embodiment" in various places in the specification are not necessarily all referring to the same embodiment and are not necessarily limited to a single or particular embodiment.

Where used herein the term "active agent" refers to an oligonucleotide comprising a seed-sequence as described herein, or to a nucleic acid compound comprising an oligonucleotide comprising a seed sequence as described herein. The oligonucleotide may be an siRNA, shRNA, DNA or RNA antisense oligonucleotide, chimeric antisense DNA/RNA, or microRNA, or other biochemical or molecule that is biologically active as described herein. By "biologically active" is meant the ability to modify the molecular, biochemical, or physiological system of a cell, organ, or organism, without reference to how the active agent has its physiological effects. In one non-limiting embodiment, biologically active refers to the ability of an active agent to target and interfere with the normal function of one or more AR coregulators.

The term "pharmaceutically acceptable" refers to active agents, compounds and compositions which are suitable for administration to humans and/or animals without undue adverse side effects such as toxicity, irritation and/or allergic response commensurate with a reasonable benefit/risk ratio. The compounds or conjugates of the present disclosure may be combined with one or more pharmaceutically-acceptable excipients, including carriers, vehicles, and diluents which may improve solubility, deliverability, dispersion, stability, and/or conformational integrity of the compounds or conjugates thereof.

As used herein, "pure," or "substantially pure" means an object species is the predominant species present (i.e., on a molar basis it is more abundant than any other object species in the composition thereof), and particularly a substantially purified fraction is a composition wherein the object species comprises at least about 50 percent (on a molar basis) of all macromolecular species present. Generally, a substantially pure composition will comprise more than about 80% of all macromolecular species present in the composition, more particularly more than about 85%, more than about 90%, more than about 95%, or more than about 99%. The term "pure" or "substantially pure" also refers to preparations where the object species is at least 60% (w/w) pure, or at least 70% (w/w) pure, or at least 75% (w/w) pure, or at least 80% (w/w) pure, or at least 85% (w/w) pure, or at least 90% (w/w) pure, or at least 92% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure.

Non-limiting examples of animals within the scope and meaning of the term "mammal" include dogs, cats, rats, mice, guinea pigs, chinchillas, horses, goats, cattle, sheep, zoo animals, Old and New World monkeys, non-human primates, and humans.

"Treatment" refers to therapeutic treatments. "Prevention" refers to prophylactic or preventative treatment measures or reducing the onset of a condition or disease. The term "treating" refers to administering a composition to a subject for therapeutic purposes and/or for prevention, or to a procedure conducted on or to the subject, e.g., a surgical procedure.

The terms "therapeutic composition" and "pharmaceutical composition" refer to an active agent-containing composition that may be administered to a subject by any method known in the art or otherwise contemplated herein, wherein administration of the composition brings about a therapeutic effect as described elsewhere herein. In addition, the compositions of the present disclosure may be designed to provide delayed, controlled, extended, and/or sustained release using formulation techniques which are well known in the art.

The term "effective amount" refers to an amount of an active agent which is sufficient to exhibit a detectable therapeutic or treatment effect in a subject without excessive adverse side effects (such as substantial toxicity, irritation and allergic response) commensurate with a reasonable benefit/risk ratio when used in the manner of the present disclosure. The effective amount for a subject will depend upon the subject's type, size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

The term "ameliorate" means a detectable or measurable improvement in a subject's condition, disease or symptom thereof. A detectable or measurable improvement includes a subjective or objective decrease, reduction, inhibition, suppression, limit or control in the occurrence, frequency, severity, progression, or duration of the condition or disease, or an improvement in a symptom or an underlying cause or a consequence of the disease, or a reversal of the disease. A successful treatment outcome can lead to a "therapeutic effect," or "benefit" of ameliorating, decreasing, reducing, inhibiting, suppressing, limiting, controlling or preventing the occurrence, frequency, severity, progression, or duration of a disease or condition, or consequences of the disease or condition in a subject.

A decrease or reduction in worsening, such as stabilizing the condition or disease, is also a successful treatment outcome. A therapeutic benefit therefore need not be complete ablation or reversal of the disease or condition, or any one, most or all adverse symptoms, complications, consequences or underlying causes associated with the disease or condition. Thus, a satisfactory endpoint may be achieved when there is an incremental improvement such as a partial decrease, reduction, inhibition, suppression, limit, control or prevention in the occurrence, frequency, severity, progression, or duration, or inhibition or reversal of the condition or disease (e.g., stabilizing), over a short or long duration of time (hours, days, weeks, months, etc.). Effectiveness of a method or use, such as a treatment that provides a potential therapeutic benefit or improvement of a condition or disease, can be ascertained by various methods and testing assays.

In at least certain embodiments, the active agents of the present disclosure are oligonucleotides (generally single stranded), and may be referred to as antisense oligonucleotides ("ASO"). As used herein, the terms "antisense oligonucleotide" and "ASO" refer to an oligomeric nucleic acid that is capable of hybridizing with its complementary target sequence, generally resulting in the modulation of the normal function of the nucleic acid (e.g., mRNA or gene) having the target sequence. "Antisense" further refers to an oligomer having a sequence of nucleotide bases and a subunit-to-subunit backbone that allows the antisense oligomer to hybridize to a target sequence in an RNA by Watson-Crick base pairing, to form an RNA:oligomer heteroduplex within the target sequence, e.g., with an mRNA. The antisense oligomer (oligonucleotide) may have exact sequence complementarity to the target sequence or near complementarity, and may include modified (non-natural) nucleobases in place of naturally complementary nucleobases. Examples of such modified nucleobases are shown below.

As used herein, the term "shRNA" or "short hairpin RNA" refers to a sequence of ribonucleotides comprising a single-stranded RNA polymer that makes a tight hairpin turn on itself to provide a "double-stranded" or duplexed region. shRNA can be used to silence gene expression via RNA interference. shRNA hairpin is cleaved into short interfering RNAs (siRNA) by the cellular machinery and then bound to the RNA-induced silencing complex (RISC). It is believed that the complex inhibits RNA as a consequence of the complexed siRNA hybridizing to and cleaving RNAs that match the siRNA that is bound thereto.

As used herein, the term "RNA interference" or "RNAi" refers to the silencing or decreasing of gene expression by siRNAs. It is the process of sequence-specific, posttranscriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi inhibits the gene by compromising the function of a target RNA, completely or partially. Both plants and animals mediate RNAi by the RNA-induced silencing complex (RISC); a sequence-specific, multicomponent nuclease that destroys messenger RNAs homologous to the silencing trigger. RISC is known to contain short RNAs (approximately 22 nucleotides) derived from the double-stranded RNA trigger, although the protein components of this activity are unknown. However, the 22-nucleotide RNA sequences are homologous to the target gene that is being suppressed. Thus, the 22-nucleotide sequences appear to serve as guide sequences to instruct a multicomponent nuclease, RISC, to destroy the specific mRNAs. Biochemical reactions that recapitulate this phenomenon generate RNA fragments of 21 to 23 nucleotides from the double-stranded RNA. These stably associate with an RNA endonuclease, and probably serve as a discriminator to select mRNAs. Once selected, mRNAs are cleaved at sites 21 to 23 nucleotides apart.

As used herein, the term "siRNA" refers to a short interfering RNA. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand"; the strand homologous to the target RNA molecule is the "sense strand", and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

In at least certain embodiments, the active agents (e.g., oligonucleotides) may have strand lengths comprising, for example, approximately 12 to 50, or 18 to 40, or 20 to 30 nucleotides, including a targeting sequence (i.e., a seed sequence) that is complementary to a target sequence of a nucleic acid which comprises a portion of an AR coregulator, such as an AR coregulator as listed elsewhere herein, a pre-mRNA transcribed from an AR coregulator, and/or (2) a mature mRNA processed from said pre-mRNA. For example, when an oligonucleotide binds to the target sequence of a preprocessed mRNA, it effectively inhibits splicing at the normal splice acceptor site and thus produces a splice variant mRNA, leading to truncated or otherwise aberrant versions of the encoded protein upon translation, or when the oligonucleotide binds to the target region of a mature mRNA, it effectively inhibits proper translation of the mRNA into an encoded protein.

The term "nucleic acid" is well known in the art. A "nucleic acid" as used herein will generally refer to a molecule (i.e., a strand) of DNA, RNA or a derivative or analog thereof, comprising a nucleobase. A nucleobase includes, for example, a naturally-occurring purine or pyrimidine base found in DNA (e.g., an adenine "A," a guanine "G," a thymine "T" or a cytosine "C") or RNA (e.g., an "A," a "G," a uracil "U" or a "C"). The term nucleobase also includes non-natural bases as described below. The term "nucleic acid" encompasses the terms "oligonucleotide" and "polynucleotide," each as a subgenus of the term "nucleic acid." The term "oligonucleotide" generally refers to a molecule of between about 3 and about 100 nucleobases in length. The term "polynucleotide" generally refers to at least one molecule of greater than about 100 nucleobases in length. These definitions generally refer to a single-stranded molecule, but in specific embodiments will also encompass an additional strand that is partially, substantially or fully complementary to the single-stranded molecule. Thus, a nucleic acid may encompass a double-stranded molecule that comprises a complementary strand or "complement" of a particular sequence comprising a molecule. As used herein, a single-stranded nucleic acid may be denoted by the prefix "ss," and a double-stranded nucleic acid by the prefix "ds. The terms "polynucleotide sequence" or "nucleic acid," as used herein, include any polynucleotide sequence which encodes a peptide or fusion protein (or polypeptide) including polynucleotides in the form of RNA, such as mRNA, or in the form of DNA, including, for instance, cDNA and genomic DNA obtained by cloning or produced by chemical synthetic techniques or by a combination thereof. The RNA or DNA may be double-stranded or single-stranded. Single-stranded DNA may be the coding strand, also known as the sense strand, or it may be the non-coding strand, also referred to as the anti-sense strand.

Where a strand is designated herein as RNA, and thus comprises uracil (U) nucleobases, the present disclosure is also directed to an equivalent DNA sequence where the U nucleobase is replaced with a thymine (T) nucleobase. For example, where an RNA active agent described herein comprises the seed sequence GUCUGA, the equivalent DNA active agent comprises the seed sequence GTCTGA.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Therefore, in the context of the present disclosure, the term "oligonucleotide" refers to an oligomer or polymer of RNA or DNA or mimetics thereof. This term includes oligonucleotides composed of naturally-occurring nucleobases, sugars and covalent internucleoside (backbone) linkages as well as oligonucleotides having non-naturally-occurring nucleobases, sugars and synthetic heterocycles and covalent internucleoside (backbone) linkages which function similarly. Such modified or substituted non-natural oligonucleotides, as compared to native (natural) forms may have desirable properties such as, for example, enhanced cellular uptake, enhanced affinity for nucleic acid target and increased stability in the presence of nucleases.

Where used herein, the term "oligonucleotide," is also intended to include linked nucleobase sequences containing modified backbones comprising non-natural internucleoside linkages. As defined in this specification, oligonucleotides having modified backbones include those that retain a phosphorus atom in the backbone and those that do not have a phosphorus atom in the backbone. Further, for the purposes of this specification, the term "nucleoside" is intended to refer to a nucleobase linked to a ribose or deoxyribose sugar (a natural nucleoside), and to a nucleobase linked to a non-ribose or non-deoxyribose heterocycle, e.g., a morpholine structure (a non-natural, or modified, nucleoside or other structures described elsewhere herein). Thus, a series of such modified, non-natural, nucleosides linked together via an internucleoside backbone can also be considered to be an oligonucleotide (a non-natural, or modified, oligonucleotide). Further, the term "sugar" where used herein in the context of a nucleoside, is intended to include "non-sugar" heterocyclic compounds, such as morpholines, as the portion of the internucleoside backbone which is linked to the nucleobase.

Oligonucleotides useful in the compounds and methods disclosed herein also include those comprising entirely or partially of naturally occurring nucleobases. Naturally occurring nucleobases as defined herein, include adenine, guanine, thymine, cytosine, and uracil. Although 5-methylcytosine (5-me-C) is technically a naturally occurring nucleobase, for the purposes of the present disclosure it will be included in the list of non-natural (a.k.a., modified) nucleobases.

As noted above, oligonucleotides of the present disclosure may further include those comprised entirely or partially of modified nucleobases and their corresponding nucleosides. These modified nucleobases include, but are not limited to, 5-uracil (pseudouridine), dihydrouracil, inosine, ribothymine, 5-me-C, 7-methylguanine, hypoxanthine, xanthine, 5-hydroxymethyl cytosine, 2-aminoadenine, 2-methyladenine, 6-methyladenine, 2-propyladenine, N6-adenine, N6-isopentenyladenine, 2-methylthio-N6-isopentenyladenine, 2-methylguanine, 6-methylguanine, 2-propylguanine, 1-methylguanine, 7-methylguanine, 2,2-dimethylguanine, 2-thiouracil, 2-thiothymine, 2-thiocytosine, 5-fluorouracil, 5-bromouracil, 5-chlorouracil, 5-iodouracil, dihydrouracil, 5-methyl-2-thiouracil, 2-thiouracil, 4-thiouracil, 5-methyluracil, uracil-5-oxyacetic acid methylester, uracil-5-oxyacetic acid, 5-carboxymethylaminomethyl-2-thiouracil, hypoxanthine, xanthine, 4-acetylcytosine, 5-(carboxyhydroxylmethyl) uracil, 5-methoxycarboxymethyluracil, 5-methoxyuracil, 5-methyl-2-thiouracil, 3-(3-amino-3-N-2-carboxypropyl) uracil, 5-carboxymethylaminomethyluracil, 5-methylaminomethyluracil, 5-methoxyaminomethyl-2-thiouracil, alkynyl derivatives of pyrimidine bases including 5-propynyl uracil, and 5-propynyl cytosine, 6-azo uracil, 6-azo cytosine, 6-azo thymine, 4-thiouracil, 8-halo-adenines, 8-amino adenine, 8-thiol adenine, 8-thioalkyl adenine, 8-hydroxyl adenine, 5-trifluoromethyl uracil, 3-methylcytosine, 5-methylcytosine, 5-trifluoromethyl cytosine, 7-methylguanine,7-methyladenine, 2-F-adenine, 2-amino-adenine, 8-azaguanine and 8-azaadenine, 7-deazaguanine, 8-halo-guanines, 8-amino guanine, 8-thiol guanine, 8-thioalkyl guanine, 8-hydroxyl guanine, 7-deazaadenine, 3-deazaguanine, 3-deazaadenine, beta-D-galactosylqueosine, beta-D-mannosylqueosine, 1-methylinosine, 2,6-diaminopurine, queosine, tricyclic pyrimidines, phenoxazine cytidine (1H-pyrimido[5,4-b][1,4]benzoxazin-2(3H)-one), and phenothiazine cytidine (1H-pyrimido [5,4-b] [1,4]benzothiazin-2(3H)-one.

The present disclosure also encompasses oligonucleotides which comprise targeting sequences (base sequences) that are complementary to particular nucleic acid target sequences taught herein. A nucleic acid is a "complement" or is "complementary" to another nucleic acid when it is capable of base-pairing with the other nucleic acid according to the standard Watson-Crick, Hoogsteen or reverse Hoogsteen binding complementarity rules. Polynucleotides (nucleic acids) are described as "complementary" to one another when hybridization occurs in an antiparallel configuration between two single-stranded polynucleotides.

More particularly, "complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target, and as such, as is understood in the art, the targeting sequence of an antisense oligonucleotide of the present disclosure need not be 100% complementary to that of its target sequence to be specifically hybridizable. An oligonucleotide is specifically hybridizable when binding of the oligonucleotide to the target sequence of the DNA or RNA molecule interferes with the normal function of the target DNA or RNA to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment, and in the case of in vitro assays, under conditions in which the assays are performed. An oligonucleotide and a target sequence are thus complementary to each other when a sufficient number of nucleobases of the oligonucleotide can hydrogen bond with the corresponding nucleobases of the target sequence, such that a desired effect will occur (e.g., antisense inhibition of a target nucleic acid, such as an AR coregulator).

For example, an oligonucleotide in which 18 of 20 nucleobases of the oligonucleotide are complementary to a target sequence, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an oligonucleotide which is 18 nucleobases in length having three noncomplementary nucleobases which are flanked by two regions of complete complementarity with the target nucleic acid, or are distributed in non-contiguous positions, would have 83% overall complementarity with the target sequence.

In other embodiments, the seed sequence of the antisense oligonucleotide provided herein is fully complementary (i.e. 100% complementary) to a target sequence of a nucleic acid, e.g., of an AR coregulator. As used herein, "fully complementary" means each nucleobase of the referenced portion of an oligonucleotide (e.g., the seed sequence) is capable of precise base pairing with the corresponding nucleobases of a target nucleic acid.

The term "target sequence" where used herein refers to a contiguous series of nucleobases in a specific nucleotide sequence (target region), for example of an mRNA. The term "target sequence" refers to a sequence that is a subsequence (portion or segment) of the target region, or to the entire sequence of the target region. A target sequence may include the 5' terminal nucleobase of a nucleic acid sequence plus adjacent internal nucleobases of the sequence, or the 3' terminal nucleobase plus adjacent internal nucleobases of the sequence, or only internal nucleobases within the sequence, or the target sequence may be 100% identical to the target region. In certain embodiments, a nucleic acid compound of the present disclosure comprises an oligonucleotide having a nucleobase sequence that, when written in the 5' to 3' direction, comprises the reverse complement of a target sequence of a nucleic acid target region to which it is targeted.

The terms "complementary" and "antisense" can be used interchangeably. Complementary also refers to polynucleotide sequences that are substantially complementary (antisense) over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches.

In certain embodiments, oligonucleotides of the present disclosure are synthesized using one or more modified nucleotides. As used herein, the terms "modified" and "modification" when used in the context of the constituents of a nucleotide monomer, i.e., sugar, nucleobase and internucleoside linkage (backbone), refer to non-natural changes to the chemical structure of these naturally occurring constituents or the substitutions of these constituents with non-naturally occurring ones, i.e., mimetics. For example, the "unmodified" or "naturally occurring" sugar ribose (of RNA) can be modified by replacing the hydrogen at the 2'-position of ribose with a methyl group. Similarly, the naturally occurring internucleoside linkage of nucleic acids is a 3' to 5' phosphodiester linkage that can be modified, in one embodiment, by replacing one of the non-bridging oxygen atoms of the phosphate linker with a sulfur atom to create a phosphorothioate linkage. Modified oligonucleotides are structurally distinguishable, but functionally interchangeable with naturally occurring or synthetic unmodified oligonucleotides and usually have enhanced properties such as increased resistance to degradation by exonucleases and endonucleases, or increased binding affinity.

As noted above, in certain embodiments, modifications to the oligonucleotides of the present disclosure encompass substitutions or changes in internucleoside linkages, sugar moieties, or nucleobases. Where used herein in reference to an oligonucleotide, the term "non-natural" or "unnatural" refers to an oligonucleotide which comprises at least one modification in an internucleoside linkage, a sugar, and/or a nucleobase thereof, wherein such modified internucleoside linkage, modified sugar, and/or modified nucleobase is not found naturally in DNA or RNA (unless specifically defined otherwise herein)

Non-naturally occurring internucleoside linkages of the oligonucleotides of the present disclosure include those that contain a phosphorus atom and also those that do not contain a phosphorus atom. Numerous phosphorus-containing modified oligonucleotide backbones are known in the art and may be used in the oligonucleotides of the present disclosure. Examples of phosphorus-containing internucleoside linkages of non-natural (modified) oligonucleotide backbones which may occur in the presently disclosed oligonucleotides include, but are not limited to, phosphorothioate, phosphorodithioate, phosphoramidite, phosphorodiamidate, morpholino, phosphotriester, aminoalkylphosphotriester, phosphonate, chiral phosphorothioates, methyl and other alkyl phosphonates including 3'-alkylene phosphonate, 5'-alkylene phosphonate and chiral phosphonate, phosphinate, phosphoramidates including 3'-amino phosphoramidate and aminoalkylphosphoramidate, thionophosphoramidate, thionoalkylphosphonate, thionoalkylphosphotriester, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage, and oligonucleotides having inverted polarity comprise a single 3' to 3' linkage at the 3'-most internucleotide linkage i.e., a single inverted nucleoside residue which may be abasic (the nucleobase is missing or has a hydroxyl group in place thereof) linkages. Examples of U.S. patents that teach the preparation of such phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050.

As noted above, in some embodiments, the internucleoside linkages are without phosphorus atoms and may instead comprise short chain alkyl or cycloalkyl internucleoside linkages, mixed heteroatom and alkyl or cycloalkyl internucleoside linkages, or one or more short chain heteroatomic or heterocyclic internucleoside linkages. In further embodiments, the non-naturally occurring internucleoside linkages are uncharged and in others, the linkages are achiral. In some embodiments, the non-naturally occurring internucleoside linkages are uncharged and achiral, such as peptide nucleic acids (PNAs).

It is understood that the sequence set forth in each sequence or SEQ ID NO contained herein is independent of any modification to sugar moieties, internucleoside linkages, or nucleobases of the sequence, unless otherwise specified. As such, antisense oligonucleotides of the present disclosure may be defined by a complementary correspondence to a sequence or SEQ ID NO disclosed herein, or segment thereof, and may comprise, independently, one or more modifications to a sugar moiety, an internucleoside linkage, or a nucleobase. Other embodiments of oligonucleotide backbones include siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Examples of U.S. patents that teach the preparation of such non-phosphorus containing oligonucleotides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439.

In certain oligonucleotide mimetics of the present disclosure, both the sugar moiety and the internucleoside linkage, i.e., the backbone, of the nucleotide units are replaced with non-natural groups. One such oligomeric compound is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Examples of U.S. patents that teach the preparation of PNA compounds include, but are not limited to, U.S. Pat. Nos. 5,539,082; 5,714,331; and 5,719,262.

The oligonucleotides described herein stabilized against nucleolytic degradation such as by the incorporation of a modification, e.g., a nucleotide modification. The oligonucleotides can include a non-natural nucleoside linkage such as a phosphorothioate linkage as the first, second, and/or third internucleotide linkage at the 5' or 3' end of the oligonucleotide sequence. In certain embodiments, the oligonucleotides can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-DMAP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) nucleotide. In a particular embodiment, the oligonucleotides include at least one 2'-O-methyl-modified nucleotide, and in some embodiments, all of the nucleotides include a 2'-O-methyl modification.

As noted elsewhere herein, the oligonucleotide can be further modified so as to be conjugated to an organic moiety such as a biogenic molecule that is selected to improve stability, distribution and/or cellular uptake of the oligonucleotide, e.g., cholesterol, forming the nucleic acid compound of the present disclosure. Such an organic moiety can be attached, e.g., to the 3' or 5' end of the oligonucleotide, and/or at the 2' position of the sugar moiety of a nucleotide of the oligonucleotide, such as the 2' ribose position.

The nucleic acid compound can further be in isolated form or can be part of a pharmaceutical composition, such as a pharmaceutical composition formulated for parental administration. The pharmaceutical compositions can contain one or more nucleic acid compounds, and in some embodiments will contain two or more inhibitory nucleic acid compounds, each one directed to a different target gene.

The oligonucleotides can be delivered in any of a variety of forms, including in liposomes as described above, and via expression vectors. The oligonucleotide can be endogenously expressed from transcription units inserted into DNA or RNA vectors. The recombinant vectors can be DNA plasmids or viral vectors for example. Viral vectors suitable for producing the presently disclosed oligonucleotides capable of reducing expression or activity of an AR coregulator can be constructed based on, but not limited to, adeno-associated virus, retrovirus, lentivirus, adenovirus, or alphavirus. The recombinant vectors which contain a nucleic acid for expressing the oligonucleotides disclosed herein can be delivered as described above and can persist in target cells. Alternatively, viral vectors can be used that provide for transient expression of the oligonucleotides. Such vectors can be repeatedly administered as necessary. Once expressed, in one embodiment, the oligonucleotides may interact with the target RNA and inhibit mRNA activity for example. The delivery vehicles (vectors) for the oligonucleotides optionally comprise an expression construct which includes an enhancer sequence, a promoter sequence, and other sequences necessary for expression of the products of the oligonucleotide sequence desired to be produced. In one embodiment, the promoter is cell-specific. The term "cell-specific" means that the particular promoter selected for the recombinant vector can direct expression of the selected transgene only in a particular cell type. As one example, the promoter is specific for expression in prostate cells. A number of viruses can be used in connection with the methods described herein, including papovaviruses, e.g., SV40, adenovirus, vaccinia virus, adeno-associated virus, herpesviruses including HSV and EBV, and retroviruses of avian, murine, and human origin. In certain embodiments, lentiviral vectors can be used in connection with the methods described herein. In certain embodiments, the lentiviral vector can be a doxycycline-inducible lentiviral vector engineered to express one or more shRNAs or siRNAs.

Specific vectors which may be used include, but are not limited to, adeno-associated virus vectors (e.g., as disclosed in U.S. Pat. Nos. 5,139,941, 5,436,146, and 5,622,856), an attenuated or gutless adenoviral vectors, (e.g., as disclosed in U.S. Pat. No. 5,935,935), lentiviral vectors (such as are disclosed in U.S. Pat. Nos. 5,665,577; 5,994,136; and 6,013,516), plasmids or synthetic (non-viral) vectors (such as disclosed in U.S. Pat. Nos. 4,394,448 and 5,676,954), and/or nanoparticles (such as disclosed, for example, in U.S. Pat. Nos. 6,217,912; 7,514,098; and 8,323,618), retroviral vectors (such as are disclosed in U.S. Pat. Nos. 5,672,510; 5,707,865; and 5,817,491), herpes virus vectors (such as are disclosed in U.S. Pat. No. 5,288,641), and sindbis virus vectors and papilloma virus vectors (such as are disclosed in EP 820 773). The vectors may be either monocistronic, bicistronic, or multicistronic. A recombinant vector (e.g., lenti-, parvo-, AAV) sequence can be packaged as a "particle" for subsequent infection (transduction) of a cell, ex vivo, in vitro or in vivo. Where a recombinant vector sequence is encapsulated or packaged into an AAV particle, the particle can also be referred to as a "rAAV." Such particles include proteins that encapsulate or package the vector genome. Particular examples include viral envelope proteins, and in the case of AAV, capsid proteins.

Thus, the oligonucleotides of the present disclosure may be used as a form of gene therapy. The term "gene therapy" as used herein means genetic modification of cells by the introduction of exogenous DNA or RNA into these cells, such as via an expression vector containing the oligonucleotide, for the purpose of expressing or replicating one or more peptides, polypeptides, proteins, oligonucleotides, or polynucleotides in vivo for the treatment or prevention of disease or deficiencies in humans or animals. Examples of gene therapy are disclosed for example in U.S. Pat. No. 5,399,346. Any suitable route of administration of the oligonucleotide-containing vector may be employed. For example, parenteral (subcutaneous, subretinal, suprachoroidal, intramuscular, intravenous, transdermal) and like forms of administration may be employed. Dosage formulations include injections, implants, or other known and effective gene therapy delivery methods.

Delivery of the oligonucleotide-expressing vectors can be systemic, such as by intravenous or intra-muscular administration, direct administration to a tumor site, such as a prostate tumor, by administration to target cells ex-planted from a subject followed by reintroduction into the subject, or by any other means that would allow for introduction into the desired target cell. The therapeutic and/or pharmaceutical compositions, in non-limiting embodiments, contain viral particles per dose in a range of, for example, from about $10^4$ to about $10^{11}$ particles, from about $10^5$ to about $10^{10}$ particles, or from about $10^6$ to about $10^9$ particles. In the context of AAV vectors, vector genomes are provided in in a range of, for example, from about $10^4$ to about $10^{14}$ vector genomes, from about $10^5$ to about $10^{13}$ vector genomes, from about $10^6$ to about $10^{13}$ vector genomes, from about $10^7$ to about $10^{13}$ vector genomes, from about $10^8$ to about $10^{13}$ vector genomes, or from about $10^9$ to about $10^{13}$ vector genomes. Such doses/quantities of AAV vector are useful in the methods set forth herein.

Because nucleases that cleave the phosphodiester linkages are expressed in almost every cell, unmodified nucleic acid molecules such as the inhibitory oligonucleotides of the present disclosure may be modified to resist degradation, as described above for example. Other biogenic molecules may be conjugated to the oligonucleotides to improve their ability to resist degradation, target certain cells, or to cross barriers like cell membranes or the blood brain barrier. Examples of biogenic molecules that can be conjugated to the oligonucelotides include lipids such as, but not limited to, stearic acid, palmitic acid, docosanoic acid, docosahexanoic acid, docosahexaenoic acid, cholesterol, tocopherol, and other C12-C22 saturated or unsaturated fatty acids; peptides such as but not limited to, cell-penetrating peptides (CPPs) such as penetratin, HIV-1 Tat peptides, pVEC-Cadherin 615-634, polyarginines (6-12), and transportan, linear and cyclic RGD-containing peptides, and SPACE peptide; receptor-specific ligands; aptamers (synthetic oligoribonucleotides); antibodies or antibody fragments; CpG-containing oligonucleotides; polyamines, such as spermine and spermidine; polymers such as dendrimers and polyethylene glycols (e.g., PEG 0.6 kDa-5,000 kDa); and saccharides such as N-acetylgalactosamine (GalNAc) and cyclodextrins. The biogenic molecule may be conjugated to the oligonucleotide by any suitable means, such as via linker or a cleavable bond such as but not limited to disulfide, thioether, pH sensitive (e.g., hydrazone or carboxymethyl-maleic anhydride), or ethylene glycol.

The oligonucleotides or nucleic acid compounds of the present disclosure may be delivered in the form of nanoparticles and microparticles which encapsulate the nucleic acid compounds within liposomes of cationic lipids or within PEG, for example. These delivery systems can enhance intracellular delivery either by protecting the nucleic acid compound from nuclease degradation and/or by promoting absorptive endocytosis. Further, the addition of dioleylphosphatidylethanolamine to liposome delivery systems results in the destabilization of endosomal membranes and promotion of release of the oligonucleotide after endocytosis. The nucleic acid compounds can be administered to cells by a variety of other methods known to those of skill in the art, including, but not limited to, ionophoresis, or by incorporation into other vehicles, such as hydrogels, cyclodextrins, biodegradable nanocapsules, and bioadhesive microspheres, or by proteinaceous vectors. In one example, the nucleic acid compounds can be delivered via the nanoparticle system shown in U.S. Patent Application Publication 2019/0255088. The liposomes may comprise amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323.

In certain embodiments, the nanoparticles which contain the nucleic acid compounds of the present disclosure may comprise a pharmaceutically acceptable carrier such as, but not limited to, poly(ethylene-co-vinyl acetate), PVA, partially hydrolyzed poly(ethylene-co-vinyl acetate), poly(ethylene-co-vinyl acetate-co-vinyl alcohol), a cross-linked poly (ethylene-co-vinyl acetate), a cross-linked partially hydrolyzed poly(ethylene-co-vinyl acetate), a cross-linked poly(ethylene-co-vinyl acetate-co-vinyl alcohol), poly-D,L-lactic acid, poly-L-lactic acid, polyglycolic acid, PGA, copolymers of lactic acid and glycolic acid, polycaprolactone, polyvalerolactone, poly (anhydrides), copolymers of polycaprolactone with polyethylene glycol, copolymers of polylactic acid with polyethylene glycol, polyethylene glycol; fibrin, Gelfoam™ (which is a water-insoluble, off-white, nonelastic, porous, pliable gel foam prepared from purified gelatin and water for injection), and combinations and blends thereof. Copolymers can comprise from about 1% to about 99% by weight of a first monomer unit such as ethylene oxide and from 99% to about 1% by weight of a second monomer unit such as propylene oxide. Blends of a first polymer such as gelatin and a second polymer such as poly-L-lactic acid or polyglycolic acid can comprise from about 1% to about 99% by weight of the first polymer and from about 99% to about 1% of the second polymer.

The oligonucleotides or nucleic acid compounds can be delivered directly by systemic administration such as using oral formulations or stereotactic injection into prostate or prostate tumor, typically in saline with chemical modifications to enable uptake, or other methods described elsewhere herein. In certain embodiments, such as when the oligonucleotide of the nucleic acid compound has a phosphorothioate backbone, the oligonucleotide binds to serum proteins, slowing excretion by the kidney. The aromatic nucleobases also interact with other hydrophobic molecules in serum and on cell surfaces. In certain embodiments, siRNA delivery systems involve complexing the RNA with cationic and neutral lipids, although encouraging results have also been obtained using peptide transduction domains and cationic polymers. Including PEGylated lipids in the formulation prolongs the circulating half-life of the particles.

As noted, one type of optimization of single-stranded DNA or RNA oligonucleotides is the use of chemical modifications to increase the nuclease resistance such as the introduction of phosphorothioate ("PS") linkages in place of the phosphodiester bond. This modification improves protection from digestion by nucleases. PS linkages also improved binding to serum proteins in vivo, increasing half-life and permitting greater delivery of active compound to tissues. Chemical modifications to subunits of the nucleotides can also improve potency and selectivity by increasing binding affinity of oligonucleotides for their complementary sequences. Examples of such modifications to the nucleoside sugars include 2'-O-methyl (2'-O-Me), 2'-fluoro (2'-F), and 2'-O-methoxyethyl (2'-MOE) RNA, and others as discussed elsewhere herein. Even more affinity can be gained using oligonucleotides modified with locked nucleic acid (LNA), which contains a methylene bridge between the 2' and 4' position of the ribose. This bridge "locks" the ribose ring in a conformation that is ideal for binding, leading to high affinity for complementary sequences. Related bridged nucleic acid (BNA) compounds have been developed and share these favorable properties. Their high affinity has permitted the development of far shorter oligonucleotides than previously thought possible which nonetheless retain high potency. The chemistry for introducing 2'-O-Me, 2'-MOE, 2'-F, or LNA into oligonucleotides is compatible with DNA or RNA synthesis, allowing chimeras with DNA or RNA bases to be easily obtained. This compatibility allows the properties of chemically modified oligonucleotides to be fine-tuned for specific applications, which is a major advantage for development that makes LNAs and other BNAs convenient tools for many applications.

Therapeutic administration of the active agents described herein include any method by which a nucleic acid (e.g., DNA or RNA), as known to one of ordinary skill in the art. For treatment of aggressive prostate cancer, delivery may be via, for example, oral administration and/or injection into the prostate gland or tumor or both.

In certain embodiments, the active agents can be delivered to an organelle, a cell, a tissue, a tumor or an organism via one or more injections (i.e., a needle injection), such as, for example, orally, subcutaneously, intradermally, intramuscularly, intravenously, or intraperitoneally.

A described inhibitory nucleic acid or other active agent can be incorporated into pharmaceutical compositions suitable for administration. For example, pharmaceutical compositions can comprise one or more the active agents and a pharmaceutically acceptable carrier.

Then active agent may be provided in a sustained release composition. The use of immediate or sustained release compositions depends on the nature of the condition being treated. If the condition consists of an acute or over-acute disorder, treatment with an immediate release form can be conducted over a prolonged release composition. Alternatively, for certain preventative or long-term treatments, a sustained release composition may be appropriate.

The active agent can be administered in a single dose or in multiple doses. Where the administration of the active agent is by infusion, the infusion can be a single sustained dose or can be delivered by multiple infusions. Injection of the active agent can be directly into the tissue at or near the site of aberrant or unwanted target gene expression. Multiple injections of the active agent can be made into the tissue, for example, into the prostate gland, into the prostate tumor, or near the tumor.

In addition to treating pre-existing aggressive or non-aggressive prostate cancers, active agents of the disclosure can be administered prophylactically in order to prevent or slow the conversion of a non-aggressive prostate cancer to an aggressive form. The active agent can be employed in combination therapies, meaning that the present compositions can be administered concurrently with, prior to, or subsequent to, one or more other desired therapeutic agents or medical procedures. The combination of therapies (therapeutic agents or procedures) to employ in a combination regimen will take into account compatibility of the desired therapeutic agents and/or procedures and the desired therapeutic effect to be achieved. It will also be appreciated that the therapies employed can achieve a desired effect for the same disorder (for example, a compound described herein can be administered concurrently with another therapeutic agent used to treat the same disorder), or they can achieve different effects (e.g., control of any adverse effects).

Known agents useful for treating cancers can be combined with the presently described active agents to treat a prostate cancer. For example, the active can be administered with another therapeutic agent simultaneously or sequentially in separate unit dosage forms or together in a single unit dosage form. The active agents are useful for individuals who have received prior medication for prostate cancer, as well as individuals who have received no prior medication for a cancer. Individuals of any age can be treated by the methods compositions of the disclosure.

It is understood that the appropriate dose of an active agent depends upon a number of factors within the knowledge of the ordinarily skilled physician, veterinarian, or researcher. The dose(s) vary, for example, depending upon the identity, size, and condition of the subject or sample being treated, further depending upon the route by which the active agents and pharmaceutical compositions are to be administered, and the effect which the practitioner desires the an active agent to have. It is furthermore understood that appropriate doses of an active agent depend upon the potency with respect to the expression or activity to be modulated. Such appropriate doses may be determined using the assays described herein. When one or more of these active agents are to be administered to an animal (e.g., a human), a relatively low dose may be prescribed at first, with the dose subsequently increased until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

In certain embodiments, an effective amount of the nucleic acid compound of the present disclosure will generally contain sufficient active agent to deliver from about 0.1 µg/kg to about 100 mg/kg (weight of active agent/body weight of patient). Particularly, the composition will deliver at least 0.5 µg/kg to 50 mg/kg, and more particularly at least 1 µg/kg to 25 mg/kg. Without wishing to be held to a specific dosage, it is contemplated that the various pharmaceutical compositions used to practice the method of the present disclosure may contain, but are not limited to, about 0.01 mg to about 10 mg of the peptide per kg body weight per dose.

Practice of the method of the present disclosure may include administering to a subject an effective amount of the nucleic acid compound in any suitable systemic or local formulation, in an amount effective to deliver the dosages listed above, including but not limited to an implantable material. In one embodiment, an effective, particular therapeutic dosage is 1 µg/kg to 10 mg/kg. The dosage can be administered on a one-time basis, or (for example) from one to five times per day or once or twice per week, or continuously via a venous drip, depending on the desired therapeutic effect. In one therapeutic method of the present disclosure, the composition is provided in an IV infusion in the range of from 1 mg/kg-10 mg/kg of body weight once a day. The duration of an intravenous therapy using the pharmaceutical composition of the present disclosure will vary, depending on the condition being treated and the condition and potential idiosyncratic response of each individual patient. In at least one embodiment, it is contemplated that the duration of each application of the nucleic acid compound may be in the range of 1 to 4 hours and given once every 12 or 24 hours by continuous intravenous administration. Other therapeutic drugs, intravenous fluids, cardiovascular and respiratory support could also be provided if requested by the attending physician in a manner known to one of ordinary skill in the art.

As used herein, the terms "complementary" or "complement" also refer to a nucleic acid comprising a sequence of consecutive nucleobases or semiconsecutive nucleobases (e.g., one or more nucleobase moieties are not present in the molecule) capable of hybridizing to another nucleic acid strand or duplex even if less than all the nucleobases do not base pair with a counterpart nucleobase. In certain embodiments, a "complementary" nucleic acid comprises a sequence in which about 70%, about 71%, about 72%, about 73%, about 74%, about 75%, about 76%, about 77%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%, and any range derivable therein, of the nucleobase sequence is capable of base-pairing with a single or double stranded nucleic acid molecule during hybridization. In certain embodiments, the term "complementary" refers to a nucleic acid that may hybridize to another nucleic acid strand or duplex in stringent conditions, as would be understood by one of ordinary skill in the art.

The term "homologous" or "% identity" as used herein means a nucleic acid (or fragment thereof) or a protein (or a fragment thereof) having a degree of homology to the corresponding natural reference nucleic acid or protein that may be in excess of 70%, or in excess of 80%, or in excess of 85%, or in excess of 90%, or in excess of 91%, or in excess of 92%, or in excess of 93%, or in excess of 94%, or in excess of 95%, or in excess of 96%, or in excess of 97%, or in excess of 98%, or in excess of 99%. For example, in regard to peptides or polypeptides, the percentage of homology or identity as described herein is typically calculated as the percentage of amino acid residues found in the smaller of the two sequences which align with identical amino acid residues in the sequence being compared, when four gaps in a length of 100 amino acids may be introduced to assist in that alignment (as set forth by Dayhoff, in Atlas of Protein Sequence and Structure, Vol. 5, p. 124, National Biochemical Research Foundation, Washington, D.C. (1972)). In one embodiment, the percentage homology as described above is calculated as the percentage of the components found in the smaller of the two sequences that may also be found in the larger of the two sequences (with the introduction of gaps), with a component being defined as a sequence of four, contiguous amino acids. Also included as substantially homologous is any protein product which may be isolated by virtue of cross-reactivity with antibodies to the native protein product. Sequence identity or homology can be determined by comparing the sequences when aligned so as to maximize overlap and identity while minimizing sequence gaps. In particular, sequence identity may be determined using any of a number of mathematical algorithms. A non-limiting example of a mathematical algorithm used for comparison of two sequences is the algorithm of Karlin & Altschul, Proc. Natl. Acad. Sci. USA 1990, 87, 2264-2268, modified as in Karlin & Altschul, Proc. Natl. Acad. Sci. USA 1993, 90, 5873-5877.

In one embodiment "% identity" represents the number of amino acids or nucleotides which are identical at corresponding positions in two sequences of a protein or nucleic acids, respectively. For example, two amino acid sequences each having 100 residues will have 95% identity when 95 of the amino acids at corresponding positions are the same. Similarly, two nucleic acid sequences each having 100 bases will have 95% identity when 95 of the bases at corresponding positions are the same.

Another example of a mathematical algorithm used for comparison of sequences is the algorithm of Myers & Miller, CABIOS 1988, 4, 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988, 85, 2444-2448. Another algorithm is the WU-BLAST (Washington University BLAST) version 2.0 software (WU-BLAST version 2.0 executable programs for several UNIX platforms). This program is based on WU-BLAST version 1.4, which in turn is based on the public domain NCBI-BLAST version 1.4 (Altschul & Gish, 1996, Local alignment statistics, Doolittle ed., Methods in Enzymology 266, 460-480; Altschul et al., Journal of Molecular Biology 1990, 215, 403-410; Gish & States, Nature Genetics, 1993, 3: 266-272; Karlin & Altschul, 1993, Proc. Natl. Acad. Sci. USA 90, 5873-5877; all of which are incorporated by reference herein).

In addition to those otherwise mentioned herein, mention is made also of the programs BLAST, gapped BLAST, BLASTN, BLASTP, and PSI-BLAST, provided by the National Center for Biotechnology Information. These programs are widely used in the art for this purpose and can align homologous regions of two amino acid sequences. In all search programs in the suite, the gapped alignment routines are integral to the database search itself. Gapping can be turned off if desired. The default penalty (Q) for a gap of length one is Q=9 for proteins and BLASTP, and Q=10 for BLASTN, but may be changed to any integer. The default per-residue penalty for extending a gap (R) is R=2 for proteins and BLASTP, and R=10 for BLASTN, but may be changed to any integer. Any combination of values for Q and R can be used in order to align sequences so as to maximize overlap and identity while minimizing sequence gaps. The default amino acid comparison matrix is BLOSUM62, but other amino acid comparison matrices such as PAM can be utilized.

Specific amino acids may be referred to herein by the following designations: alanine: ala or A; arginine: arg or R; asparagine: asn or N; aspartic acid: asp or D; cysteine: cys or C; glutamic acid: glu or E; glutamine: gln or Q; glycine: gly or G; histidine: his or H; isoleucine: ile or I; leucine: leu or L; lysine: lys or K; methionine: met or M; phenylalanine: phe or F; proline: pro or P; serine: ser or S; threonine: thr or T; tryptophan: trp or W; tyrosine: tyr or Y; and valine: val or V.

The terms "oligonucleotide", "polynucleotide sequence" or "nucleic acid," as used herein, may include polynucleotide sequences which have particular activity or encode peptides or polypeptides, e.g., proteins, and include polynucleotides in the form of RNA, such as mRNA, or in the form of DNA, including, for instance, cDNA and genomic DNA obtained by cloning or produced by chemical synthetic techniques or by a combination thereof, or a non-coding sequence such as siRNA, shRNA, miRNA, or other such short RNA sequences. The DNA may be double-stranded or single-stranded. Single-stranded DNA may be the coding strand, also known as the sense strand, or it may be the non-coding strand, also referred to as the anti-sense strand.

As noted, the term "antisense" refers to a polynucleotide or oligonucleotide molecule that is substantially complementary or 100% complementary to a particular polynucleotide or oligonucleotide molecule (RNA or DNA), i.e., a "sense" strand, or portion thereof. For example, the antisense molecule may be complementary in whole or in part to a molecule of messenger RNA, miRNA, pRNA, tRNA, rRNA of hnRNA, or a sequence of DNA that is either coding or non-coding.

The term "operably linked" where used herein refers to an association of two chemical moieties linked in such a way so that the function of one is not affected by the other, e.g., an arrangement of elements wherein the components so described are configured so as to perform their usual function. The two moieties may be linked directly, or may be linked indirectly via a linker sequence of molecule.

The term "primer" refers to an oligonucleotide sequence which serves as a starting point for DNA synthesis in the polymerase chain reaction (PCR). A primer generally comprises from about 12 to about 30 nucleotides and hybridizes with a complementary region of a target sequence, for example a microRNA molecule.

The term "probe" refers to an oligonucleotide which is bound to or configured to bind to a target sequence, and includes for example, an antisense nucleic acid sequence which is designed to hybridize by a sequence-specific method with a complementary region of a specific nucleic acid sequence such as a target nucleic acid, such as an miRNA as disclosed herein. An oligonucleotide probe can comprise any number of nucleotides, such as 10 to 25, as long as the oligonucleotide probe comprises a sufficient number of nucleotides to bind to the target nucleic acid with the necessary specificity for the particular use of the probe. For purposes of quantification of the probe-target sequence complex, the probe may further optionally comprise a tag or label operably linked thereto, wherein the tag or label comprises, for example, a fluorescent (e.g., fluorophore), luminescent, or chemiluminescent label or reporter group. Oligonucleotides with binding specificity to the RNAs and cDNAs expressed from the biomarker panel disclosed herein may be referred to as "capture molecules" in the assay systems and methods disclosed herein.

The term "fluorophore" or "fluorochrome" or "fluorescent species" or "fluorescent label" or "fluorescent tag," as used herein indicates a substance which itself fluoresces or can be made to fluoresce. Each term is interchangeable. Fluorophores can be used alone or covalently attached ("operably-linked") or non-covalently linked to another molecule, such as an oligonucleotide primer, probe, or miRNA, such as described herein. The process of covalently attaching a fluorophore to another molecule or compound is referred to as "fluorescent labeling" and may be conducted by, for example, an enzyme effective in forming the covalent bond therebetween.

Examples of fluorophores which may be used in various embodiments of the present disclosure include but are not limited to: hydroxycoumarin, methoxycoumarin, Alexa fluor 345, aminocoumarin, 7-diethylaminocoumarin-3-carboxylic acid, Cy2 (cyanine 2), FAM, Alexa fluor 350, Alexa fluor 405, Alexa fluor 488, Fluorescein (FITC), Alexa fluor 430, Alexa fluor 532, HEX 535, Cy3, Alexa fluor 546, Alexa fluor 555, R-phycoerythrin (PE), tetramethyl rhodamine (TRITC), Rhodamine Red-X, Tamara, Cy3.5, Rox, Alexa fluor 568, Red 613 480, Texas Red 615, Alexa fluor 594, Alexa fluor 633, Allophycocyanin, Alexa fluor 647, Cy5, Alexa fluor 660, Cy5.5, TruRed 490, Alexa fluor 680, Alexa fluor 750, Cy7, DAPI, QSY 7, QSY 33, dabsyl, BODIPY FL, BODIPY630/650, BODIPY 650/665, BODIPY TMR-X, BODIPY TR-X, Hoechst 33258, SYTOX blue, Hoechst 33342, YOYO-1 509, SYTOX green, TOTO1, TO-PRO-1, SYTOX orange, Chromomycin A3, Mithramycin, propidium iodide, ethidium bromide, Pacific Orange, Pacific Green, Pacific Blue, Oregon Green 488, Oregon Green 514, red fluorescent protein (RFP), green fluorescent protein (GFP), and cyan fluorescent protein (CFP).

Certain novel embodiments of the present disclosure, having now been generally described, will be more readily understood by reference to the following examples, which are included merely for purposes of illustration of certain aspects and embodiments of the present disclosure, and are not intended to be limiting. The following examples are to be construed, as noted above, only as illustrative, and not as limiting of the present disclosure in any way whatsoever. Those skilled in the art will promptly recognize appropriate variations from the various compositions, structures, components, procedures and methods.

EXPERIMENTAL

Material and Methods
Cell Culture and Plasmid Constructs

LNCaP, 22Rv1, DU145, RWPE1, PC3 and HEK 293T cell lines were obtained from American Type Culture Collection (ATCC), VCaP cells were obtained from Sigma-Aldrich, Panc-1 cells were obtained from Dr. Priyabrata Mukherjee (Oklahoma University Health Sciences Center), and LentiX-293T cells were obtained from Clonetech. LNCaP and 22Rv1 cells were maintained in RPMI Glutamax growth media (Gibco), DU145, HEK293T, VCaP, PC3 and Panc-1 and LentiX-293T cells were maintained in DMEM growth media (Gibco), and RWPE1 were maintained in KSF media (Gibco). Both RPMI and DMEM media were supplemented with 10% fetal bovine serum (FBS), 100 units/mL penicillin, 100 μg/mL streptomycin, Amphotericin B and 2 mM L-Glutamine. pLKO.1 vector was used for shRNA expression, and plasmids were obtained from Open Biosystems or cloned using pLKO.1-TRC (pLKO.1-TRC cloning vector was a gift from Dr. David Root (Addgene plasmid #10878; http://n2t.net/addgene:10878; RRID:Addgene_10878)) and the pLKO.1-TRC cloning vector protocol obtained from Addgene. shRNA target sequences were as follows (Note: Most shRNAs used in this work (Table 1) come from the RNAi consortium shRNA library, and TRC numbers are provided for these sequences. shTMEFF2-6 and shTMEFF2-9 sequences were generated using the siRNA Wizard online tool by Invitrogen: https://www.invivogen.com/sirnawizard/).

TABLE 1 shRNA sequences and TRC numbers

| shRNA | Sequence | TRC No. | SEQ ID NO |
|---|---|---|---|
| shTMEFF2-1 | CTGGTTATGATGACAGAGAAA | TRCN0000073522 | 1 |
| shTMEFF2-2 | CGTCTGTCAGTTCAAGTGCAA | TRCN0000222559 | 2 |
| shTMEFF2-3 | GCGCTTCTGATGGGAAATCTT | TRCN0000073521 | 3 |
| shTMEFF2-4 | GCAGGTGTGATGCTGGTTATA | TRCN0000073520 | 4 |
| shTMEFF2-5 | CCTTGCATTTGTGGTAATCTA | TRCN0000073518 | 5 |
| shTMEFF2-6 | GGCTCTGGAGAAACTAGTCAA | | 6 |
| shTMEFF2-7 | ATGCAGAGAATGCTAACAAAT | TRCN0000373776 | 7 |
| shTMEFF2-8 | CATACCTTGTCCGGAACATTA | TRCN0000373700 | 8 |
| shTMEFF2-9 | GGCACTACAGTTCAGACAATA | | 9 |
| shScramble | CCTAAGGTTAAGTCGCCCTCG | | 10 |
| shGFP | CGACGTAAACGGCCACAAGTT | | 11 |
| shL3 | ACTGGGCTGTACTTTGTATAT | TRCN0000059000 | 12 |
| shR6 | CCTGAAACAGTGGCAATAAAT | TRCN0000038696 | 13 |

CRISPR Cas9 (pRCCH-CMV-Cas9-2A-Hygro) and doxycycline inducible sgRNA (pRSGT16-U6Tet-(sg)-CMV-TetRep-2A-TagRFP-2A-Puro) plasmids were obtained from Cellecta. Constitutive sgRNA expressing vector, pLX-sgRNA, was a gift from Dr. Eric Lander & Dr. David Sabatini (Addgene plasmid #50662; http://n2t.net/addgene:50662; RRID:Addgene_50662), and sgRNA were cloned using an Addgene protocol. Cloned sgRNA target sequences were: sgGFP (AAGATCGAGTGCCGCATCAC) (SEQ ID NO:14) and sgTMEFF2-3 (CCAGCTGCTGCACTGCCGCG) (SEQ ID NO: 15).

RetroX-ON and RetroX-Tight-Pur vectors transduced sequentially into C4-2B cells, were used for doxycycline inducible TMEFF2 overexpression. LentiX 293T cells (Clonetech) and CalPhos transfection reagents (Clonetech) were used for viral particle packaging. psPAX2 and VSV-G plasmids were used for lentiviral packaging. psPAX2 was a gift from Dr. Didier Trono (Addgene plasmid #12260; http://n2t.net/addgene:12260; RRID:Addgene_12260), and pCMV-VSV-G was a gift from Dr. Robert Weinberg (Addgene plasmid #8454; http://n2t.net/addgene:8454; RRID:Addgene_8454). pCL-10A1 plasmid was used for retroviral packaging. Viral concentrations necessary for approximately 90% or greater survival (for non-toxic constructs) in selection antibiotic were used for transductions. For retroviral and lentiviral transductions, cells were seeded in 6 cm plates at 50% confluency, and viral particle containing supernatant was diluted in 1.5 ml of 8 µg/ml polybrene serum free media and added to cells. After 5 hours, 1.5 ml of 10% FBS growth media was added to transduction media. Growth media refreshed 24 hours after initial viral particle exposure. Transduced cells were stably selected for an average of 10 days using the following selection antibiotic concentrations: Puromycin 1 µg/ml, hygromycin 750 µg/ml, G418 800 ug/ml. Selection antibiotic was not used for short time course experiments (1 week or less) with shRNA constructs when the generation of stable cell lines was not possible.

Antisense Oligo Transfections

FANA antisense oligos (ASOs) were obtained from AUM Biotech. LNCaP cells were transfected with 250 nM ASO (Non-target or pool of 4 targeting TMEFF2) using 0.19% Dharmafect #3 transfection reagent. 48 hours after transfection, cells were treated with 10% CSS RPMI for 24 hours, followed by 24 hours in 10 nM dihydrotestosterone (DHT) or 0.0001% ethanol (EtOH).

RNA Extractions and Lysate Preparations

For experiments measuring gene expression response to DHT, cells were washed with PBS and treated with 10% charcoal stripped serum (CSS) containing growth media for 24 hours for hormone depletion, followed by 24 hours in 10 nM DHT (Sigma Aldrich) or 0.0001% EtOH vehicle in 10% CSS growth media, at which time samples were collected. Cells were maintained in 10% FBS growth media for all experiments not using DHT. RNeasy (Qiagen) with on-column DNAse treatment (Qiagen) was used for RNA extractions. Cell Signaling lysis buffer 9803 was used for whole cell lysates, and NE-PER kit (Thermo) was used for Nuclear/Cytoplasmic protein extractions.

Western Blot Analysis and Antibodies

Proteins were separated via 10% SDS/PAGE using mini-PROTEAN TGX stain free gels (Biorad) and transferred onto 0.2 µm nitrocellulose membranes using the semi-dry turbo transfer system (Biorad). One-hour incubation in 5% NFDM in tris-buffered saline 0.1% tween 20 (TBST) was used for blocking, followed by overnight incubation at 4 degrees Celsius with primary antibody diluted in 5% NFDM TBST. anti-TMEFF2 (Sigma HPA015587) 1:1000, anti-PSA (abcam 76113) 1:1000, anti-FKBP5 (abcam 2901) 1:1000, anti-AR (Cell Signaling D6F11) 1:1000, anti-ERG (abcam 92513), anti-Calnexin (abcam 22595) 1:4000. Goat anti-rabbit HRP conjugated secondary antibody (ThermoFisher 31460) was diluted in 5% NFDM at a concentration of 80 ng/ml. Clarity Western ECL (Biorad) or SuperSignal West Femto (Thermo) were used for chemiluminescent detection Quantitative RT PCR RNA samples were reverse transcribed using iScript reverse transcription supermix (500 ng/rxn) (Biorad). RT qPCR reactions were carried out in 96 well plates (25 ng cDNA/well and 200 nM per primer/well) using Sso Advanced Universal SYBR Green supermix (Biorad) and the Biorad CFX96 touch RTPCR detection system. Each reaction (sample/primer set combination) was run in duplicate and triplicate to ensure accurate loading. Forward and reverse primers used are shown in para. [0104] of U.S. Provisional application Ser. No. 62/935,521. Relative gene expression was calculated via ΔΔCT or pfaffl method, when appropriate, and LinRegPCR software was used to calculate primer amplification efficiency. At least 2-4 housekeeping genes were used for normalization per run, with the geometric mean of CT values being used for normalization of gene expression. Housekeeping genes used for normalization included, CANX, HPRT1, PSMA1, RPL8, RPL38, and PPP2CA. Statistics: Two-tailed T tests were used to calculate significant differential gene expression. P<0.05 was considered to be statistically significant.

RNA Sequencing

Deep paired-end RNA sequencing analysis targeted to the TMEFF2 locus for de novo isoform detection was carried out by Oklahoma Medical Research Foundation's Sequencing Facility. One sample of LNCaP RNA was used for analysis, and over 317 million reads were obtained after decontamination. The genomic region of focus was the TMEFF2 locus −/+ 1Mbp upstream and downstream (chr2: 190949046-193194933). StringTie (v.1.2.3) was used for transcript reconstruction.

For differential gene expression analyses with LNCaP shScramble/shTMEFF2-3−/+DHT, 36 hours post-transduction cells were grown in CSS RPMI for 24 hours, followed by 24 hours in 10 nM DHT or 0.0001% EtOH vehicle control. In both cases RNA samples were prepared as described in the RNA extractions and lysate preparations section of the materials and methods. Three repeats were analyzed for each RNA sequencing analysis. RNA sequencing and initial statistical analyses were carried out by Novogene. RNA integrity was analyzed by Agilent 2100 to ensure sample quality. mRNAs were isolated using polyT magnetic beads, which was followed by fragmentation. Two cDNA libraries were synthesized using random hexamer primers; one with dTTP to dUTP substitutions in the second strand to allow for strand specificity, and one library without substitution. cDNA fragments from both libraries were ligated to NEBNext Adaptor and purified using AMPure XP beads after PCR amplification. A read depth of 20 million reads was used for each sample using an Illumina Next-Generation sequencer. For quality control purposes, error rate distributions and G/C content were analyzed in reads, and low-quality reads containing adapter sequences, >10% unknown nucleotides or low Qscore values were eliminated. STAR was used for mapping clean reads to the human transcriptome and genome, and differential gene expression was determined using the DESeq2 R package. P-values were adjusted using the Benjamini and Hochberbg method. Transcripts with average log 2 fold change >0.5 (n=3) and adjusted p-value <0.05 were considered significantly differentially expressed.

Enrichment Analysis

Essential gene lists were derived from the following publications: Wang et al., 2015 (Wang T, Birsoy K, Hughes N W, Krupczak K M, Post Y, Wei J J, Lander E S, Sabatini D M. *Identification and characterization of essential genes in the human genome*. Science. 2015 Nov. 27; 350(6264): 1096-101) and Fei et al., 2017 (Teng Fei, Yiwen Chen, Tengfei Xiao, Wei Li, Laura Cato, Peng Zhang, Maura B. Cotter, Michaela Bowden, Rosina T. Lis, Shuang G. Zhao, Qiu Wu, Felix Y. Feng, Massimo Loda, Housheng Hansen He, X. Shirley Liu, Myles Brown. *Genome-wide CRISPR screen identifies HNRNPL as a prostate cancer dependency regulating RNA splicing*. Proceedings of the National Academy of Sciences June 2017, 114 (26) E5207-E5215). For the essential gene list derived from Wang et al., 2015, genes with under-represented reads were identified from the sequencing data from the following cell lines: KBM7, K562, Raji, Jiyoye. Only genes that were essential in two or more of the four cell lines were considered essential in our study (1739 total genes, with 1705 genes having consistent RNA seq reads from our RNA seq analysis with LNCaP shScramble/shTMEFF2-3−/+DHT samples). For the Fei et al., 2017 list, all of the top 999 essential LNCaP genes were used for our study. In addition, all 274 AR co-regulators from DePriest, et al., 2016 ((DePriest, A. D., Fiandalo, M. V., Schlanger, S., Heemers, F., Mohler, J. L., Liu, S., & Heemers, H. V. *Regulators of Androgen Action Resource: a one-stop shop for the comprehensive study of androgen receptor action*. Database: the journal of biological databases and curation, 2016, bav125) were used for AR coregulatory gene list. Gene ontology (GO) and Kyoto Encyclopedia of Genes and Genomes (KEGG) lists were also used in enrichment analyses. Where used herein in regard to gene lists, the term "essential" does not imply that it is essential for a particular gene or gene product to be targeted in order for the presently disclosed method be effective.

P-values for enrichment analyses were calculated using the following formula:

$$p = 1 - \sum_{i=0}^{m-1} \frac{\left[\begin{array}{c}M\\i\end{array}\right]\left[\begin{array}{c}N-M\\n-i\end{array}\right]}{\left[\begin{array}{c}N\\n\end{array}\right]}$$

where p=p value, N=total genes, M=genes of pathway/gene list, n=differentially expressed genes, and i=overlap of M and n.

Sylamer Analysis

The following online resource was used for sylamer analyses: http://www.genomique.info/sylamer/. Genes from a given comparison were rank ordered based on fold differential gene expression from most downregulated to most up regulated and submitted to sylamer analysis. Sylamer analysis compares enrichment p values of all possible words of a given length (6,7,8) from sequences of transcript 5'UTR, coding region or 3'UTR, and provides the most enriched words and corresponding enrichment log 10 p values.

shRNA Seed Match Analysis

The following online resource was used to generate strand specific shRNA seed match gene lists: https://dharmacon-.horizondiscovery.com/resources/tools-and-calculators/sirna-seed-locator/. Since the online resource is intended for siRNA with a length of 19 nucleotides, while TRC-shRNAs contain 21 nucleotide target sequences, probable Drosha/Dicer cuts were taken into account when submitting 19 nucleotide sequences. A 2-nucleotide trim was used for the passenger strand and a 3 nucleotide trim was used for the guide strand. As an additional control, a shTMEFF2-3 guide strand sequence with 2 nucleotides trimmed was also used (shTMF2-3 Guide +1, see Table S4. Appendix 1). After seed match lists were generated, genes with multiple seed matches were eliminated from single seed match lists. Single and multiple seed match lists were compared to essential and AR coregulatory gene lists. Statistics: Pearson's Chi-square test of independence was used to identify significant associations between seed match and gene down-regulation or upregulation. Yates correction was used for comparisons that contained values of 10 genes or fewer to limit type 1 error rate associated with small sample size. P<0.05 was considered statistically significant.

Cell Growth and Viability Assays

For growth and viability analyses, LNCaP, 22Rv1, DU145, Panc-1 and HEK293T cell lines were transduced with pLKO.1 shRNA constructs as described in the cell culture and plasmid constructs section of the materials and methods. Cells were trypsinized and seeded in 6 well plates 24 hours post-transduction at the following concentrations: $1\times10^5$ cells/well (HEK293T, DU145, Panc-1), $2\times10^5$ cells/well (LNCaP, 22Rv1). Cells were counted using Nexcelom Auto T4 Cellometer, and trypan blue was used to selectively count live cells and assess viability. Cells were trypsinized and counted using the same method 24 hours after seeding (36 hours after seeding for LNCaP, which require longer time for attachment) for initial cell count. Growth was analyzed by counting cells again at 48 hours after initial cell count, and lastly 72 hours (DU145, Panc-1, HEK293T) or 96 hours after initial cell count (LNCaP, 22Rv1 due to slower growth rate of these cells). Viability was assessed at each time point via trypan blue, and percent viability was averaged for 48 and 72 hour time points (HEK293T, DU145, Panc-1) or 48 and 96 hour time points for slower growing cell lines (22Rv1, LNCaP). Viability of RWPE1 cells transduced with shRNA was determined at 96 hours and 120 hours after transduction. Relative percent viability was then calculated by dividing percent viability of knockdown cell lines by percent viability in shScramble control. Percent growth inhibition was calculated using the following formula:

$$\% \ GI = 1 - \left[ \frac{\left[ \frac{(K_f - K_i)}{K_i} \right]}{\left[ \frac{(S_f - S_i)}{S_i} \right]} \right]$$

where % GI=% Growth Inihibition, $K_f$=Final cell count of knockdown cell line, $K_i$=Initial cell count of knockdown cell line, $S_f$=Final cell count of shScramble cell line, $S_i$=Initial cell count of shScramble cell line. Growth and viability analyses were repeated 3 times for each cell line.

Statistics Significance was calculated using two-tailed T-test. P<0.05 was considered to be statistically significant.

Identification of Toxic Seed Sequences by Large-Scale Screening

A large-scale viability screen was used to identify 6-mer seed RNAi sequences that were most efficient at promoting toxicity in prostate cancer at different stages of the disease. The general strategy, schematically represented in FIG. 5, conducted a viability screen using a pooled shRNA library that represents all possible 6-mer seed sequences during the course of 0-28 days, followed by next generation sequencing (NGS) to quantify shRNA representation. shRNAs that decrease viability (i.e., were toxic) are depleted in the final population. Comparison across cell lines/conditions define the shRNAs that preferentially target the different stages of the disease. shRNAs were synthesized as oligonucleotides differing in a 7-nt seed sequence. Adding a nucleotide to the conventional 6-mer seed accounts for potential Dicer "shifts" resulting in noncanonical cuts. The 16,384 ($4^7$) different 7-nt seed sequences were inserted in a shRNA backbone and cloned into a doxycycline (Dox) inducible PLKO.1 TRC lentiviral cloning vector modified to include primer target sequences for PCR shRNA recovery, and unique barcode sequences to identify the presence of each of the different shRNAs (Cellecta). Only 15,572 were used in the final screen after removal of redundant sequences that could compromise the expression (i.e. TTTTTTT) or that contained restriction sites incompatible with the cloning. The resulting plasmid pool was sequenced to confirm shRNA representation, and then packaged into lentiviral particles, titrated and transduced into the selected cell lines (22Rv1 grown in the presence or absence of dihydrotestosterone, DHT) at a MOI of 0.3-0.5 to avoid multiple infection. After puromycin selection, a portion of cells was collected as day 0 sample. The rest was continuously cultured in the presence of Dox and maintained at an average of 1000-fold shRNA representation for reproducibility. To compute the relative effects of the shRNAs, we determined the average barcode representation from samples collected at 7 and 28 days of growth (corresponding to 2 and 10 population doublings) and compared that with the average initial barcode representations at day 0. Two biological replicates will be used per cell line/condition/time point. shRNAs that are toxic to the cell and are thus depleted at the end of the screen, were considered hits. shRNA hits are selected based on comparison across the cell lines/conditions to identify those that are most toxic to each specific stage of the disease. Selected cell lines/conditions used in this screen represent distinct disease stages: 22Rv1 is a CRPC cell line that constitutively expresses an active AR splice variant, AR-V7, as well as the full-length AR (ARfl), and, as a result, it displays hormone-independent growth representing advanced disease (in -DHT condition), but can also respond to hormonal stimulation (+DHT condition).

Results

Multiple shRNAs Targeting TMEFF2 Inhibit Androgen Signaling

Figure 1B:
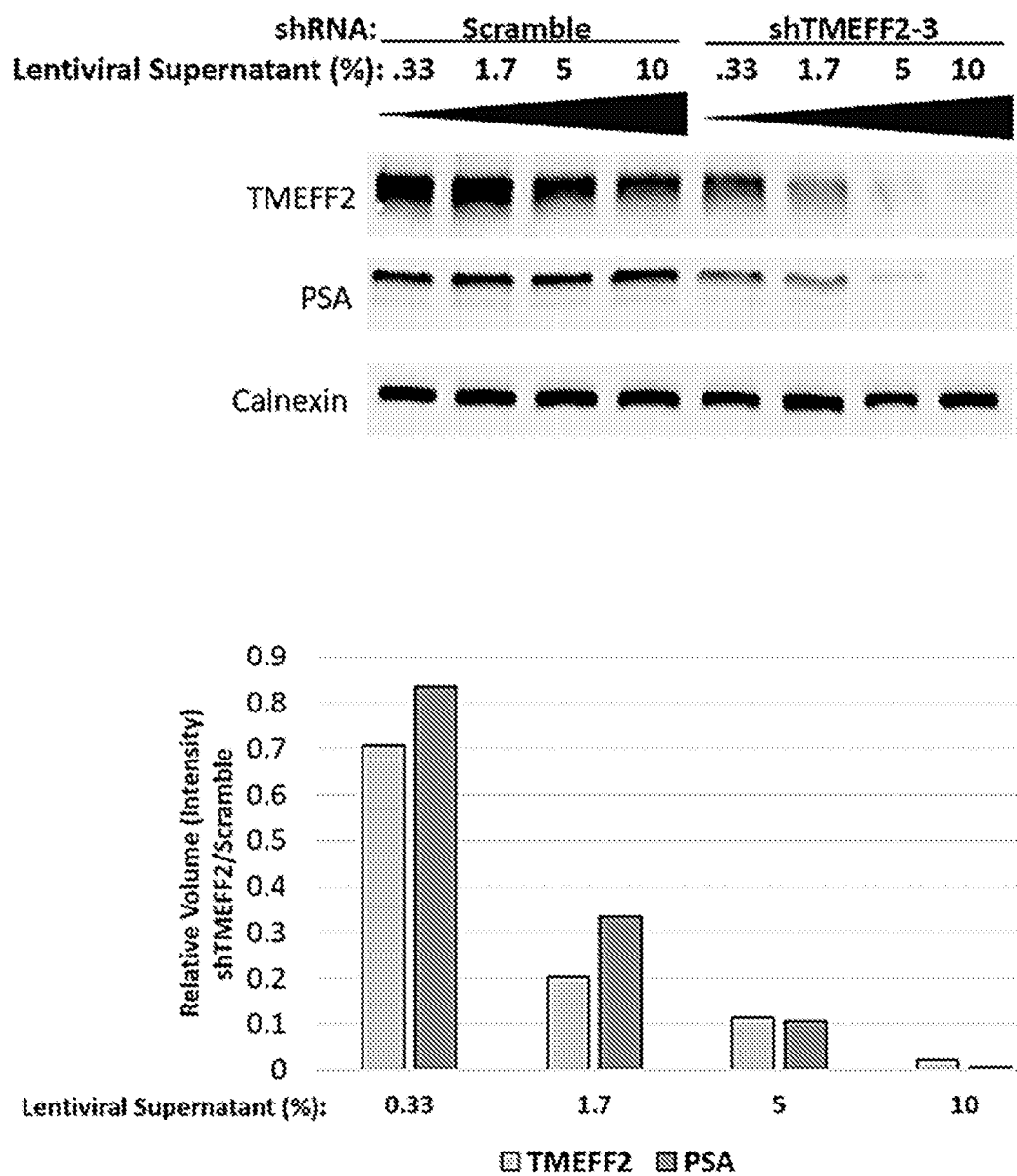
FIG. 1B shows a Western blot analysis of PSA and TMEFF2 protein levels in response to increasing dose of shTMEFF2-3 and shScramble control shRNA in LNCaP cells four days after transduction (upper panel). Dose is presented as percentage of lentiviral supernatant in transduction media. Lower panel is a graphical representation of Calnexin normalized PSA and TMEFF2 levels relative to shScramble control at each dose. Band intensity was quantified using Biorad Image Lab. Multiple shRNAs targeting TMEFF2 reduce AR and androgen responsive protein levels in LNCaP and 22Rv1 PCa cell lines.
Figure 1C:
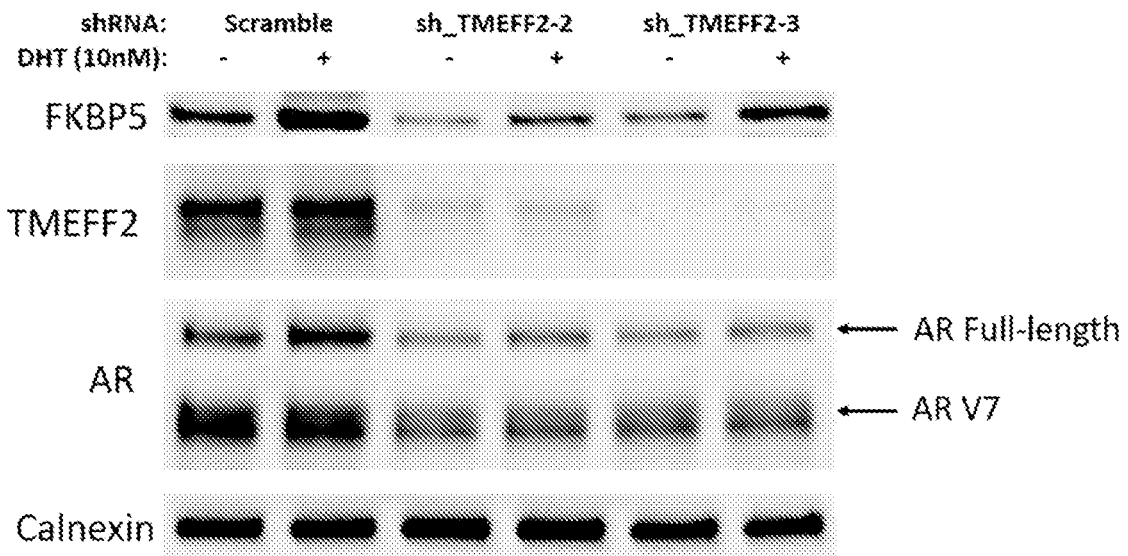
FIG. 1C shows a Western blot analysis in 22Rv1 cells showing protein levels of TMEFF2, AR (including both full length and the constitutively active AR V7 isoform) and FKBP5 in response to two TMEFF2 targeted shRNA (-2 and -3) in the presence and absence of 10 nM DHT. Calnexin was used as a loading control.
Figure 1D:
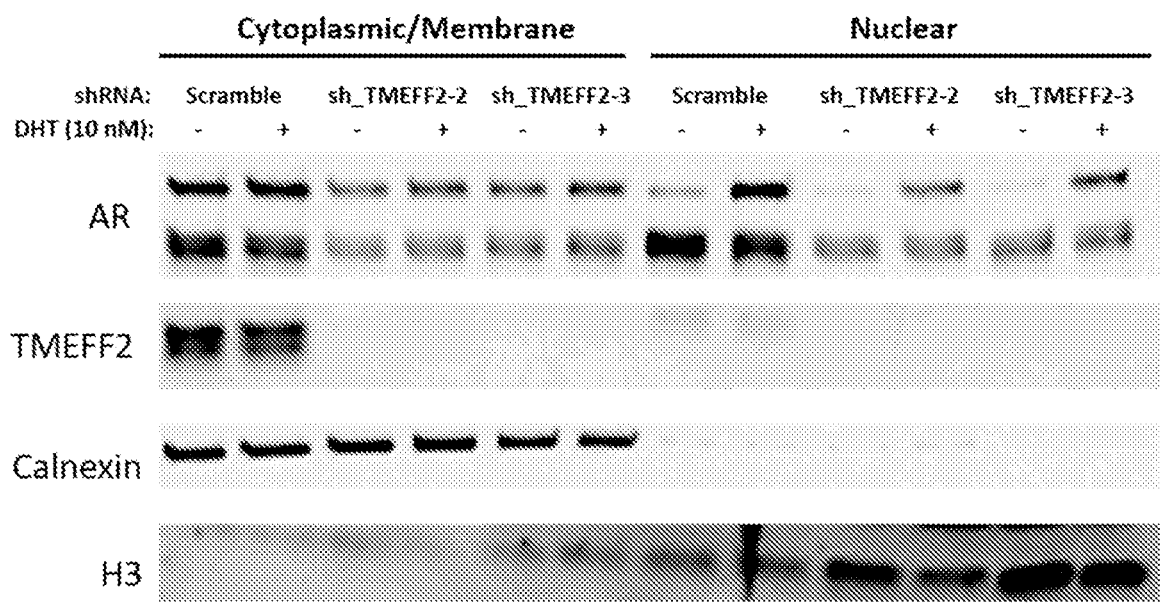
FIG. 1D shows a Western blot analysis of cell fraction lysates shows cytoplasmic and nuclear levels of both AR isoforms in response to shRNAs targeting TMEFF2 in 22Rv1 cells. Calnexin, an ER protein, was used as a loading and fractionation control for cytoplasmic/membrane lysates, and H3 was used as a loading and fractionation control for nuclear lysates.

Western blot analysis was used to determine relative TMEFF2 and AR protein expression in three benign prostate epithelial, three ADPC and four CRPC cell lines. We found a strong coincidence of TMEFF2, PSA and AR expression, and noticed a trend toward higher TMEFF2 levels in ADPC cell lines (see FIG. S1A of U.S. Provisional application Ser. No. 62/935,521), correlating with a previous finding that TMEFF2 mRNA levels are higher in primary PCa compared to benign prostate and CRPC. In order to test our hypothesis that TMEFF2 functions as a regulator of androgen signaling in PCa, we used shRNA to knockdown TMEFF2 in four TMEFF2+/AR+ PCa cell lines, including two ADPC cell lines (LNCaP and VCaP), and two CRPC cell lines, (22Rv1 and C4-2B), and measured androgen responsive protein levels in presence and absence of DHT via western blot analyses. In LNCaP cells, transductions with nine independent shRNAs (shTMEFF2-1 thru shTMEFF2-9), targeting eight of the ten exons and 3'UTR of the TMEFF2 transcript, resulted in lower protein expression of two androgen responsive genes (PSA and FKBP5) and AR compared to cells transduced with scramble control shRNA (shScramble) (FIG. 1A). Furthermore, lentiviral dose response experiments with two TMEFF2-targeted shRNAs demonstrated that TMEFF2 and PSA reductions tightly correlate with one another, even at low lentiviral dose (FIG. 1B herein, FIG. S1B of U.S. Provisional application Ser. No. 62/935,521). TMEFF2 was knocked-down with two shRNAs in 22Rv1, C4-2B and VCaP cell lines, resulting in reductions in AR targets in all cases (FIG. 1C herein, FIG. S1C of U.S. Provisional application Ser. No. 62/935,521). TMEFF2-targeted shRNAs resulted in reductions in total and nuclear levels of full length AR isoform 1 and the constitutively active AR-V7 in 22Rv1 cells (FIGS. 1C-D), suggesting that the effect on androgen signaling is not dependent on the AR ligand binding domain. RT qPCR analysis of 53 genes commonly upregulated by the AR showed down regulation in 88% of genes (47 of 53; median log 2 fold change: −0.7212) in shTMEFF2-2 vs shScramble control expressing 22Rv1 cells (FIG. S1D of U.S. Provisional application Ser. No. 62/935,521), further supporting androgen signaling inhibition in response TMEFF2-targeted shRNA. In correlation with reduced androgen signaling, we observed a high amount of toxicity and difficulty generating cell lines with stable TMEFF2 knockdown. In LNCaP shTMEFF2-3 cells, TMEFF2 mRNA levels recovered after approximately 6 days in culture, while reductions in KLK3 (PSA transcript) remained for more than two weeks after transduction (FIG. S1E of U.S. Provisional application Ser. No. 62/935,521).

The Inhibition of Androgen Signaling by TMEFF2 shRNA is not a Consequence of low TMEFF2

Figure 2A:
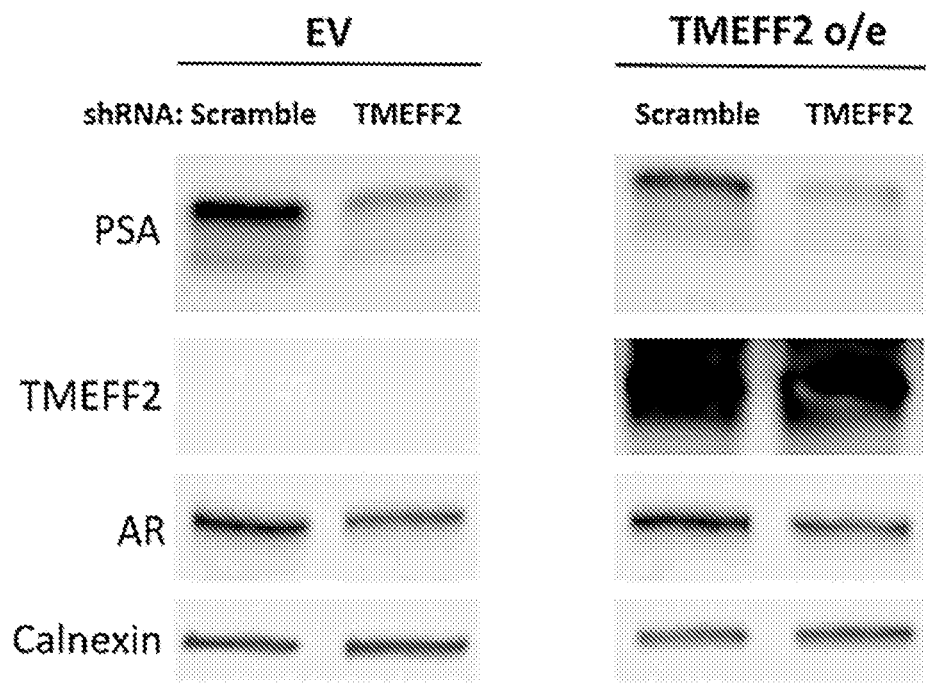
FIG. 2A shows a Western blot analysis of TMEFF2, PSA and AR levels in C4-2B cells transfected with an empty vector (EV) or an overexpressing doxycycline-inducible recombinant TMEFF2 vector (TMEFF2o/e) and transduced with either shTMEFF2-3 or shScramble shRNA. 250 ng/ml doxycycline was used to induce TMEFF2 overexpression for 2 days prior and three days after shRNA transductions. Calnexin was used as a loading control.
Figure 2B:
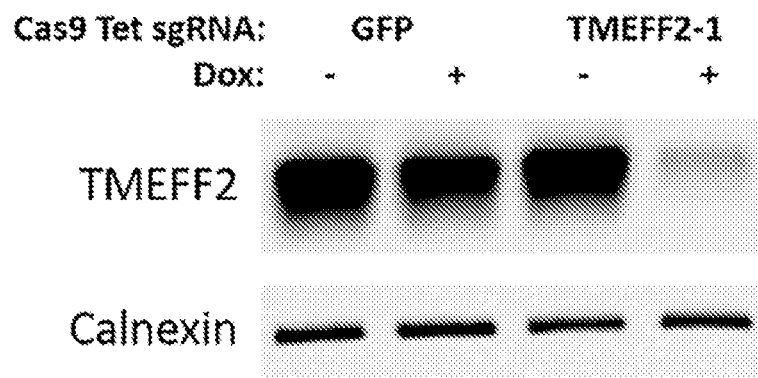
FIG. 2B shows a Western blot analysis showing TMEFF2 protein levels in LNCaP cells expressing doxycycline inducible sgRNA (sgTMEFF2-1 and sgGFP) after 6 days in the presence or absence of 500 ng/ml doxycycline. Calnexin was used as a loading control.
Figure 2C:
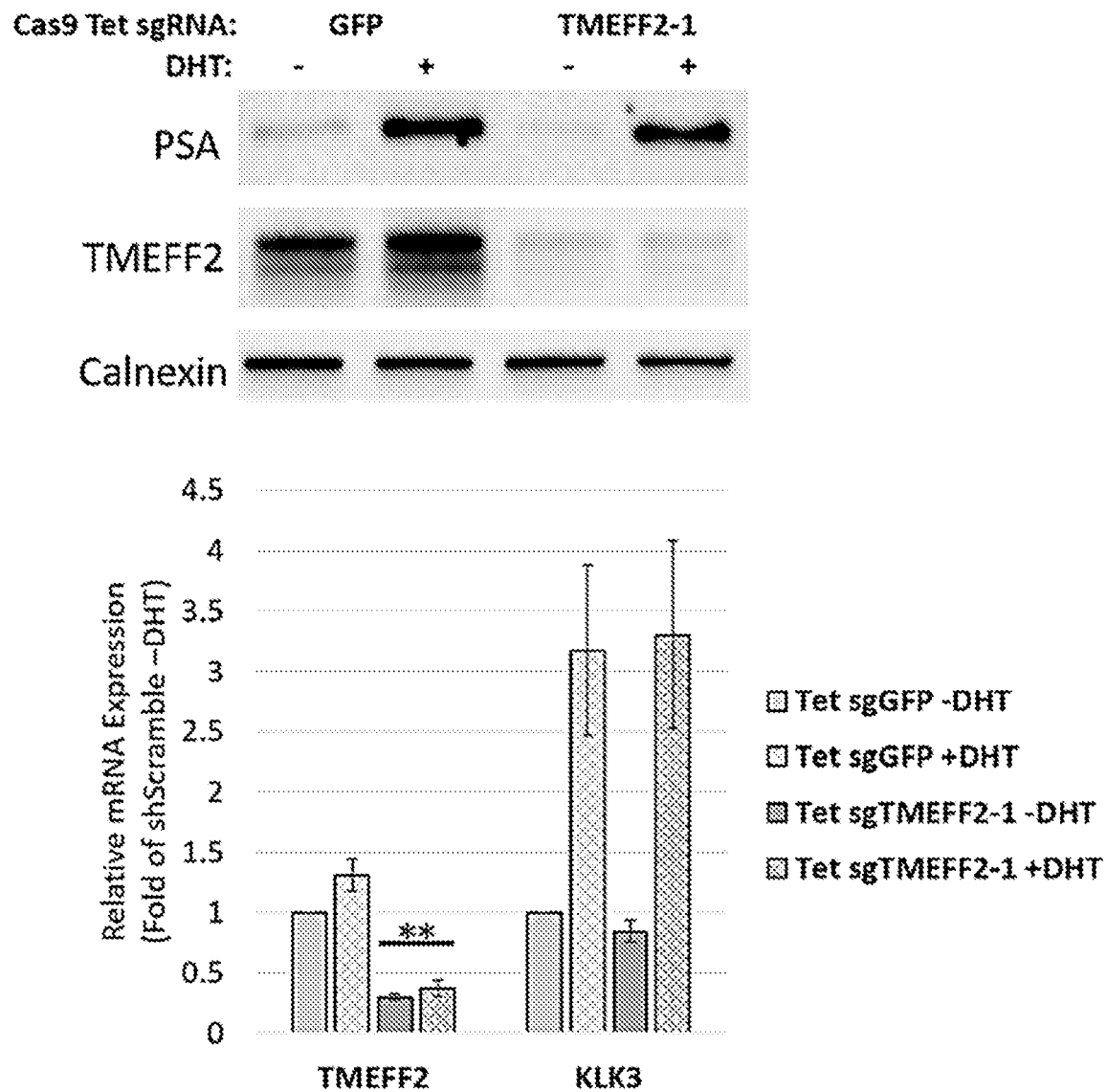
FIG. 2C shows Western blot and RT qPCR analyses. TMEFF2 and PSA protein levels (upper panel), and TMEFF2 and KLK3 (PSA transcript) mRNA levels (lower panel), were measured by western blot and RT qPCR analysis in sgTMEFF2-1 knockdown and sgGFP control LNCaP Cas9 cells grown in the presence and absence of DHT. Calnexin was used as a loading control in western blot analysis. CANX and HPRT1 mRNA levels were used for normalization in RT qPCR analysis, and relative gene expression was normalized to the sgGFP control grown in the absence of DHT (-DHT) sample. N=3, error bars ±SD, *p<0.05.

To further confirm that the androgen signaling phenotype was on-target, we overexpressed recombinant TMEFF2 isoform 1 in C4-2B cells using a doxycycline (Dox) inducible vector (FIG. S2A of U.S. Provisional application Ser. No. 62/935,521), and determined TMEFF2 overexpression resulted in negligible changes in PSA expression (FIG. S2A of U.S. Provisional application Ser. No. 62/935,521), and was also insufficient to rescue the reduction of PSA or AR protein levels by TMEFF2 targeted shRNA (FIG. 2A). One potential explanation for this discrepancy is that TMEFF2 has multiple isoforms; therefore, targeting of other isoforms could be responsible for the effect on androgen signaling seen with shRNA-mediated knockdown. To determine whether this is the case, we used a Dox inducible CRISPR Cas9 system in LNCaP cells to knockdown TMEFF2 protein expression via induced frameshift mutations in exon 1 of TMEFF2. Of note, all known TMEFF2 isoforms contain exon 1 in their open reading frame (ORF). Using this method, TMEFF2 protein expression was knocked-down>90% with the addition of Dox in LNCaP cells expressing the TMEFF2 targeted sgRNA (sgTMEFF2-1) compared to the control sgRNA targeting GFP (sgGFP) (FIG. 2B). Significant reductions in TMEFF2 mRNA were also noticed, presumably due to nonsense mediated decay of the transcript; however, PSA levels were not affected by CRISPR Cas9 mediated TMEFF2 knockdown (FIG. 2C), nor was toxicity evident in these cells (data not shown). In order to detect potentially unknown isoforms lacking the canonical AUG or exon 1 in ORFs, or long non-coding RNAs (lncRNAs) potentially targeted by TMEFF2 shRNAs, we conducted a deep paired-end RNA-seq analysis of the TMEFF2 locus in LNCaP cells for de novo isoform detection. Only transcript isoform 1 (ENST00000272771.9) contains all nine of the TMEFF2 shRNA target sequences, while isoform 2 (ENST00000392314.5) contains eight of nine target sequences (Table S1 and Appendix 1 of U.S. Provisional application Ser. No. 62/935,521), and both contain exon 1 and the canonical AUG. All other transcripts detected contain two or fewer TMEFF2 shRNA target sequences. Therefore, sequencing analyses suggest that it is highly improbable for the nine TMEFF2 shRNAs to be targeting an isoform from the TMEFF2 locus not targeted by CRISPR Cas9.

Figure 2D:
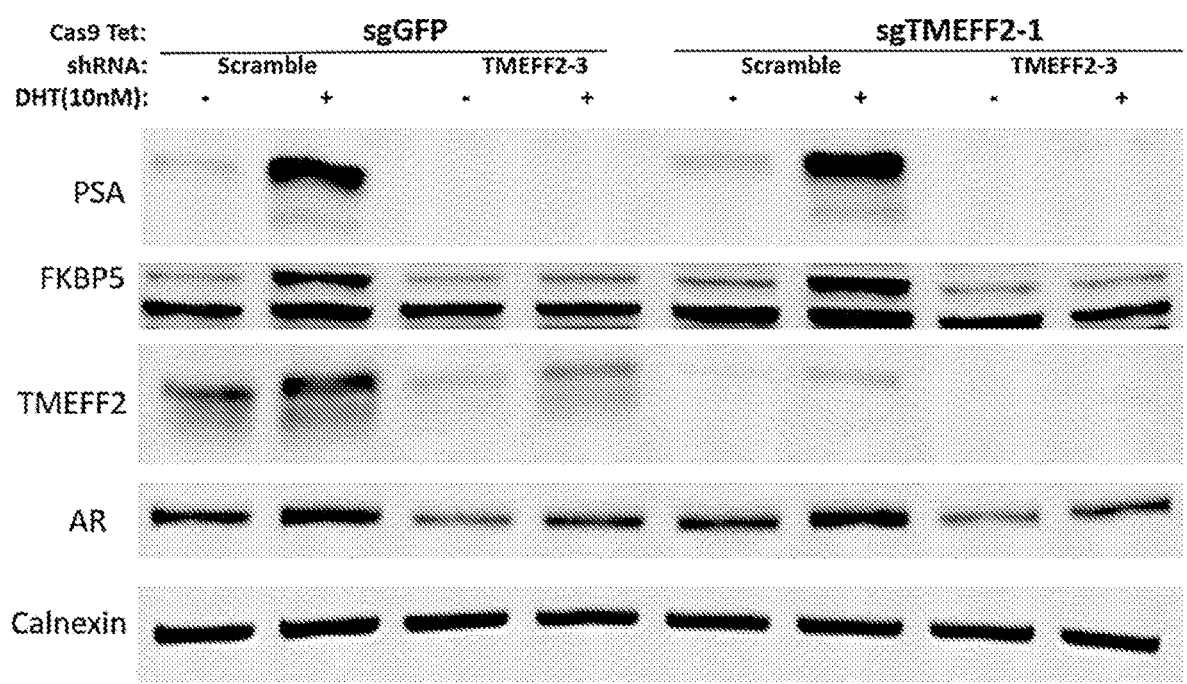
FIG. 2D shows Western blot analysis showing TMEFF2, PSA, FKBP5 and AR protein levels in LNCaP Cas9 sgGFP control and sgTMEFF2-1 knockdown cell lines, which were transduced with shScramble or shTMEFF2-3 shRNA and grown in the presence or absence of 10 nM DHT. Calnexin was used as a loading control. LNCaP Cas9 sgGFP and sgTMEFF2-1 cells were incubated in 500 ng/ml doxycycline for 2 weeks to induce TMEFF2 knockdown. Doxycycline was then removed from culture media for 2 weeks, at which time cells were transduced with shScramble or shTMEFF2 shRNA.

The divergent androgen signaling phenotypes in shRNA and CRISPR Cas9 mediated TMEFF2 knockdown could have been the result of OTEs, CRISPR Cas9 mediated concealment of low androgen signaling phenotype, or low TMEFF2 levels could have been interacting with shRNA-induced cell stress to elicit the low androgen signaling phenotype. To test these possibilities, CRISPR Cas9 sgGFP and sgTMEFF2 LNCaP cells were Dox treated to induce knockdown, followed by transductions with either shTMEFF2-3 or shScramble shRNA. In both CRISPR Cas9 LNCaP cell lines (sgGFP and sgTMEFF2), TMEFF2 targeted shRNA led to a reduction in PSA, FKPB5 and AR protein levels, while the levels of these proteins remained unaffected in shScramble control cells (FIG. 2D). Similar results were also obtained using a different sgRNA targeting TMEFF2 (sgTMEFF2-3) expressed from a constitutive expression vector (pLX-sgRNA) in LNCaP cells (FIG. S2B of U.S. Provisional application Ser. No. 62/935,521).

Figure 3:
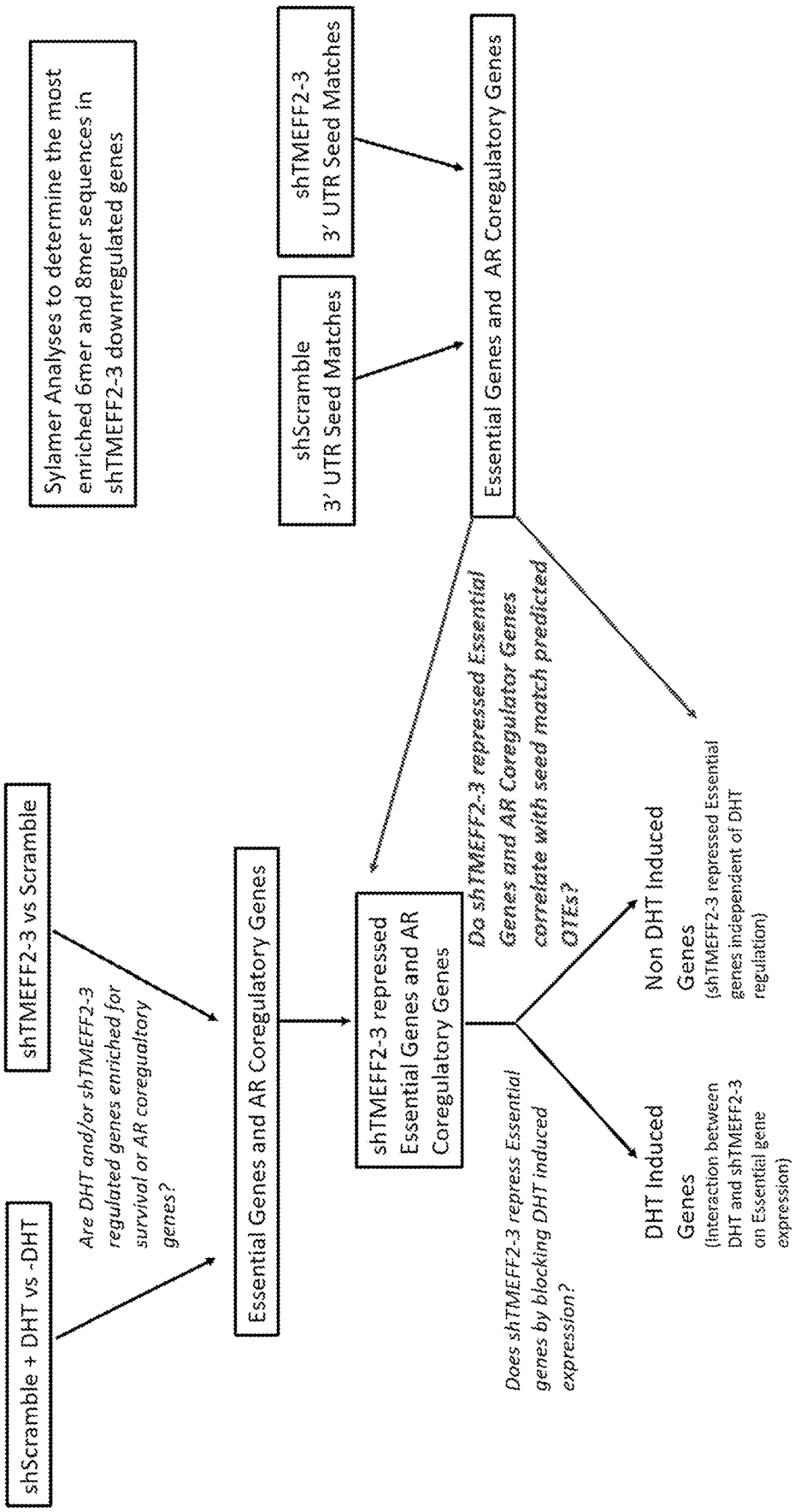
FIG. 3 is a flow chart illustrating workflow for determining whether shTMEFF2-3 works in a DISE-like mechanism, downregulating essential and AR coregulatory genes through shRNA seed matches to the 3'UTR.

In addition to CRISPR Cas9, pooled FANA antisense oligos (ASOs), which work via nuclear RNaseH mediated transcript degradation, were also used to knockdown TMEFF2 in LNCaP cells. Similar to CRISPR Cas9 mediated knockdown, no reductions in PSA or AR protein levels were evident using ASO mediated TMEFF2 knockdown (FIG. S2C of U.S. Provisional application Ser. No. 62/935,521). Together, these data suggest that while the low androgen signaling phenotype is consistent using multiple independent TMEFF2-targeting shRNAs and several PCa cell lines, it was not the result of low TMEFF2 expression, but likely the result of OTEs.

shRNA Targeting TMEFF2 Downregulates Essential and AR Coregulator Gene Expression and Inhibits Global Androgen Transcriptional Response In order to delineate target genes responsible for the low androgen signaling phenotype induced by TMEFF2 targeted shRNA, we conducted RNA seq analyses from LNCaP shTMEFF2-3 and shScramble cells grown in the presence and absence of DHT. RNA was extracted three days after shRNA transductions in order to ensure adequate expression of TMEFF2 targeted shRNA at the time of analysis. Log 2 fold change>0.5 and adj p-value<0.05 were used to define significant differential gene expression. Differential gene expression was determined between TMEFF2 knockdown and control cells and in response to DHT treatment in both cell lines. A near total inhibition of androgen transcriptional response was evident in LNCaP shTMEFF2-3 cells, in which 13 genes were differentially expressed with DHT treatment, compared to 1,423 genes in shScramble control LNCaP cells (data shown in FIG. 3A of U.S. Provisional application Ser. No. 62/935,521). Furthermore, of the genes differentially expressed with DHT treatment in LNCaP shScramble cells, a majority (867 of 1423 genes) were also differentially expressed between LNCaP shTMEFF2-3 and shScramble cells in the presence or absence of DHT (data shown in FIG. 3A of U.S. Provisional application Ser. No. 62/935,521). Gene ontology (GO) and Kyoto Encyclopedia of Genes and Genomes (KEGG) enrichment analyses indicate that many of the gene sets and pathways enriched among DHT induced genes in LNCaP shScramble control cells, such as, cell division and DNA replication, are also enriched among genes downregulated by shTMEFF2-3 in the presence of DHT (data shown in FIG. 3B of U.S. Provisional application Ser. No. 62/935,521), suggesting inhibition of androgen signaling is a strong contributor to the transcriptomic landscape and phenotype of shTMEFF2-3 expressing LNCaP cells. Genes within the p53 signaling pathway were enriched among genes elevated in LNCaP shTMEFF2-3 cells compared to shScramble in the presence of DHT (data shown in FIG. 3B of U.S. Provisional application Ser. No. 62/935,521), consistent with toxicity noticed in LNCaP shTMEFF2-3 cells. In effort to delineate the mechanism through which shTMEFF2-3 inhibits androgen signaling, we utilized Qiagen's Ingenuity Pathway Analysis (IPA) to identify potential causal networks and master regulators affected by shTMEF2-3. AR and multiple AR coregulators were among the master regulators identified (data shown in FIG. 3C of U.S. Provisional application Ser. No. 62/935,521), and of those, AR, TAF1 and USP12 were also significantly downregulated by shTMEFF2-3 (data shown in FIGS. 3C and S3A-B of U.S. Provisional application Ser. No. 62/935,521). In order to determine whether the downregulation of AR coregulators is a broader effect in LNCaP shTMEFF2-3 cells, we utilized a published list of AR coregulators (DePriest et al., 2016) and found that a significant number (38 out of 274, $p<7\times10^{-6}$) were downregulated by shMTEFF2-3 in the presence or absence of DHT, while similar significance levels were not found among differentially expressed genes in other comparisons (data shown in FIGS. 3C and S2A of U.S. Provisional application Ser. No. 62/935,521). These data indicate that shTMEFF2-3 inhibits androgen signaling in LNCaP cells, at least partly, through the depletion of AR and AR coregulators.

To confirm the effect of shRNA to TMEFF2 on AR and AR-coregulators, we conducted RNA-Seq analysis in LNCaP cells expressing 3 different shRNAs to TMEFF2, shTMEFF2-3, -4, and -9, and with shL3, a shRNA that targets CD45L and is known to promote DISE. For these experiments, cells were grown in complete media and RNA was extracted 55 hours after transfection with the shRNAs to circumvent potential changes in AR targets secondary to loss of viability, which we observe only after 72 hrs after transfection. Differential gene expression (DGE) was determined comparing cells expressing the different shRNAs to those expressing the shScramble control, followed by Metascape Enrichment Analysis of the down- and up-regulated gene lists. Enriched terms for downregulated genes common to all shRNAs were related to androgen response and endocrine therapy resistance (top 3 categories); these were not represented in the top GO terms enriched for upregulated genes (data shown in FIGS. 3D-F of U.S. Provisional application Ser. No. 62/935,521). These results indicate that shRNA to TMEFF2 promotes global downregulation of the AR transcriptional response in PCa cells. Importantly, shL3 also promoted downregulation of the AR transcriptional response in LNCaP cells, suggesting that DISE in PCa cells involves AR signaling, perhaps anticipated based on the essential role of AR signaling in survival of PCa cells. In addition, using the published list of AR coregulators (DePriest et al., 2016), we observed that the downregulated genes in the LNCaP cells transfected with for each of the shRNAs were significantly enriched in AR coregulators (data shown in FIG. 3B of U.S. Provisional application Ser. No. 62/935,521).

We hypothesized that the toxicity induced by TMEFF2 targeted shRNA was similar to the previously described RNAi-mediated cell death mechanism, DISE, which is the result of OTEs that involve si/shRNA seed interactions with the 3' UTR of multiple essential survival genes, and is characterized, in part, by transcriptomic effects that include the downregulation of essential survival and histone transcripts. Using essential gene lists generated from two independent studies of CRISPR Cas9 lethality screens, which used leukemia and lymphoma cell lines (Wang et al., 2015), or LNCaP cell line (Fei et al, 2107), we found significant enrichments for both essential gene lists in the set of genes downregulated in LNCaP shTMEFF2-3 cells ($p<5\times10^{-15}$, $p<2\times10^{-10}$) (data shown in FIG. 3G, Table S2B and Appendix 1 of U.S. Provisional application Ser. No. 62/935,521). We also detected an enrichment of essential genes induced by DHT in LNCaP shScramble cells ($p<4\times10$-65, $p<4\times10.10$) as expected, due to the androgen dependent nature of LNCaP cells. Given the impact of shTMEFF2-3 on androgen signaling, it seemed plausible that androgen signaling inhibition was a major contribution of essential gene downregulation by shTMEFF2-3. Indeed, a significant overlap of common targets was evident between essential genes induced by DHT in LNCaP shScramble cells and those downregulated by shTMEFF2-3 for both essential gene lists ($p<4\times10^{-59}$, $p<2\times10^{-13}$) (data shown in FIG. 3G, Table S2C and Appendix 1 of U.S. Provisional application Ser. No. 62/935,521). In addition to essential survival genes, histone transcripts, while not significantly modulated by DHT in LNCaP shScramble cells, were also significantly enriched among genes downregulated by shTMEFF2-3 (23 of 87 histone genes, $p<3.8\times10^{-9}$) (data shown in FIG. 3G, Table S2D and Appendix 1 of U.S. Provisional application Ser. No. 62/935,521), resembling the described DISE transcriptomic phenotype.

The shTMEFF2-3 Guide Strand Seed Region Targets the 3'UTR of Essential and AR Coregulatory Genes, Leading to Downregulation In order to determine whether shTMEFF2-3 may downregulate essential and AR coregulatory genes in LNCaP cells through an off-target DISE-like mechanism (see FIG. 3 for workflow), we utilized Sylamer analysis (https://genomique.info/sylamer/) to determine significantly enriched 6mer and 8mer sequences associated with LNCaP shTMEFF2-3 downregulated genes in rank ordered gene expression lists. Sylamer analysis is a useful tool for miRNA discovery and delineating RNAi OTEs. The 6mer 3'UTR sequence (GGGAAA), complementary to a seed sequence on the shTMEFF2-3 guide strand (UUUCCC), was found to be the most significantly enriched 6mer sequence associated with total, as well as essential and AR coregulator, gene downregulation in LNCaP shTMEFF2-3 cells in the presence and absence of DHT (data shown in FIGS. 5A, S4A, S4B, Table S3 and Appendix 1 of U.S. Provisional application Ser. No. 62/935,521). shTMEFF2-3 seed matched sequences were significantly enriched in coding region of shTMEFF2-3 total downregulated genes in LNCaP cells (data shown in FIG. S4C and Table S3 of U.S. Provisional application Ser. No. 62/935,521), although to a lesser extent, but not in the coding region of downregulated essential and AR coregulatory genes (data shown in Table S3 of U.S. Provisional application Ser. No. 62/935,521). shTMEFF2-3 seed matched sequences were also significantly enriched among 8mer 3'UTR sequences (data shown in Table S3 of U.S. Provisional application Ser. No. 62/935,521). These analyses indicate that shTMEFF2-3 guide strand seed-mediated OTEs significantly influence gene expression mainly through binding to complementary 3'UTR sequences in LNCaP cells expressing shTMEFF2-3.

To confirm the association between 3'UTR seed matches and shTMEFF2-3 downregulated essential and AR coregulatory genes, we used Dharmacon seed locator software (https://dharmacon.horizondiscovery.com/resources/tools-and-calculators/sirna-seed-locator/) to find genes with single and multiple 3'UTR seed matches to the shTMEFF2-3 and shScramble shRNA passenger and guide strands. We then tested for associations between essential and AR coregulatory genes containing seed matches and shTMEFF2-3 downregulated genes in LNCaP cells; shTMEFF2-3 upregulated and genes induced by DHT in LNCaP shScramble cells served as control comparisons. The shTMEFF2-3 guide strand seed was significantly associated with LNCaP shTMEFF2-3 downregulated essential (Wang et al., 2015, $p=5.1 \times 10^{-7}$; Fei et al., 2017, $p=8.4 \times 10^{-5}$) and AR coregulatory genes ($p=0.006$) (data shown in FIG. 5B, Table S4 of U.S. Provisional application Ser. No. 62/935,521), further supporting the results obtained by Sylamer analyses. While associations are much weaker compared to the shTMEFF2-3 guide strand, some off target activity from the passenger strand cannot be ruled out. Together these data suggest that shTMEFF2-3 shRNA leads to the downregulation of essential and AR coregulatory genes through guide strand seed complementarity to the 3'UTR of said genes.

Next, because a significant number of androgen induced essential genes are downregulated by shTMEFF2-3 (data shown in FIG. 3G of U.S. Provisional application Ser. No. 62/935,521), we repeated the association analyses after separating essential genes into androgen induced and non-androgen induced categories. The significance of the association between shTMEFF2-3 guide strand seed match and LNCaP shTMEFF2-3 downregulated genes increased for non-androgen induced essential genes (Wang et al., 2015, essential genes: $p=5.2 \times 10^{-17}$, Fei et al., 2017, essential genes: $p=5.2 \times 10^{-7}$, FIG. 5C of U.S. Provisional application Ser. No. 62/935,521), compared to all essential genes (Wang et al., 2015, essential genes: $p=5.1 \times 10^{-7}$, Fei et al., 2017, essential genes: $p=8.4 \times 10^{-5}$, FIG. 5B of U.S. Provisional application Ser. No. 62/935,521); however, associations with downregulated androgen induced essential genes were not significant (data shown in FIG. 5C of U.S. Provisional application Ser. No. 62/935,521). 86% and 74% of essential genes downregulated by shTMEFF2-3 in LNCaP cells either contained seed matches, were androgen responsive or both in Wang et al., 2015 and Fei et al., 2017 lists, respectively (data shown in FIG. S5 of U.S. Provisional application Ser. No. 62/935,521). These data indicate that androgen induced essential gene downregulation in shTMEFF2-3 cells is a consequence of androgen signaling inhibition, and likely the result of the seed-mediated downregulation of androgen signaling regulatory genes. Among those genes, the 3'UTR of AR was found to have four seed matches to the shTMEFF2-3 guide strand. A significant negative correlation was evident between AR mRNA expression and the number of guide strand seed matches to the AR 3'UTR when multiple TMEFF2-targeted shRNAs were compared to shScramble in LNCaP cells (data shown in FIG. 5D of U.S. Provisional application Ser. No. 62/935,521). One other TMEFF2 shRNA, shTMEFF2-9, was found to have four seed matches to the AR 3'UTR and significantly lower AR mRNA expression in LNCaP cells as well. Therefore, AR mRNA, in addition to numerous AR coregulatory genes, is a likely target of the shTMEFF2-3 seed, resulting in a strong repression of androgen signaling and the downregulation of androgen-induced essential genes.

Furthermore, Sylamer analysis identified miR-4446-5p as having an identical seed sequence to the shTMEFF2-3 guide strand. Using an online miRNA database) (https://www.mirbase.org/), we found that miR-4446-5p predicted targets were significantly enriched with LNCaP shTMEFF2-3 downregulated genes, as well as, essential genes in particular (data shown in FIG. 5E of U.S. Provisional application Ser. No. 62/935,521). Additionally, shTMEFF2-3 downregulated genes in LNCaP cells had a significantly higher miR-4446-5p miRDB target score compared to other predicted targets (data shown in FIG. 5E of U.S. Provisional application Ser. No. 62/935,521), and miRDB target score negatively correlated with fold change gene expression in LNCaP shTMEFF2-3 cells, with the absence of DHT being more significant than in the presence of DHT (data shown in FIGS. S6A-B of U.S. Provisional application Ser. No. 62/935,521). Genes involved in cell proliferation were also found to be enriched among the 1148 predicted miR-4446-5p targets (FIG. 4C); these proliferative gene included genes downregulated by shTMEFF2-3 in LNCaP cells, such as RAD21, CENPA and CDK7. Since miR-4446-5p has an identical 6mer seed to shTMEFF2-3, and little sequence similarity outside the seed region (data shown in FIG. 5E of U.S. Provisional application Ser. No. 62/935,521), this correlative relationship between predicted targets and shTMEFF2-3 downregulated genes in LNCaP cells suggests a tumor suppressive function for miR-4446-5p.

Sylamer followed by seed match analyses were also conducted with downregulated genes from LNCaP cells expressing shTMEFF2-3, -4, -9, or shL3 and grown in complete media. Confirming the data presented above, we observed that for these shRNAs, downregulation of AR-coregulators is also significantly associated with shRNA seed matches (data shown in FIGS. 5F,G,H of U.S. Provisional application Ser. No. 62/935,521). Importantly, using the miRNA database we found that miR-634 predicted targets were significantly enriched with LNCaP shTMEFF2-4 downregulated genes, and miRDB target score negatively correlated with fold change gene expression in LNCaP shTMEFF2-4 cells (data shown in FIG. 5I of U.S. Provisional application Ser. No. 62/935,521).

Figure 4A:
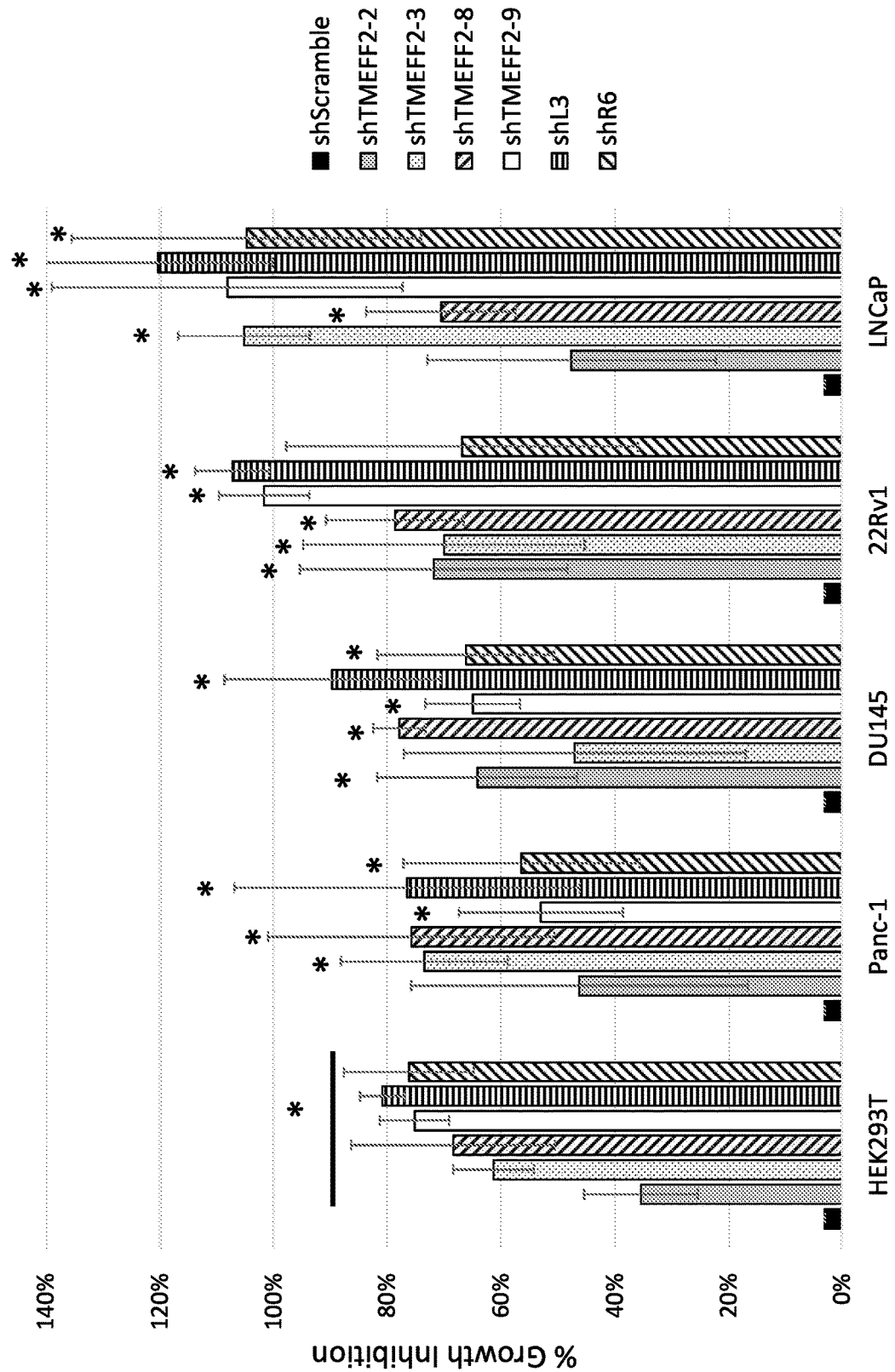
FIG. 4A is a bar graph showing percent growth inhibition of targeted shRNAs relative to shScramble control in HEK293T, Panc-1, DU145, 22Rv1 and LNCaP cell lines. N=3, error bars±SD, *p<0.05, as calculated by two tailed T-test. TMEFF-targeted shRNA are toxic to transformed cells, and toxicity correlates with reduced expression of androgen responsive genes in LNCaP cells.
Figure 4B:
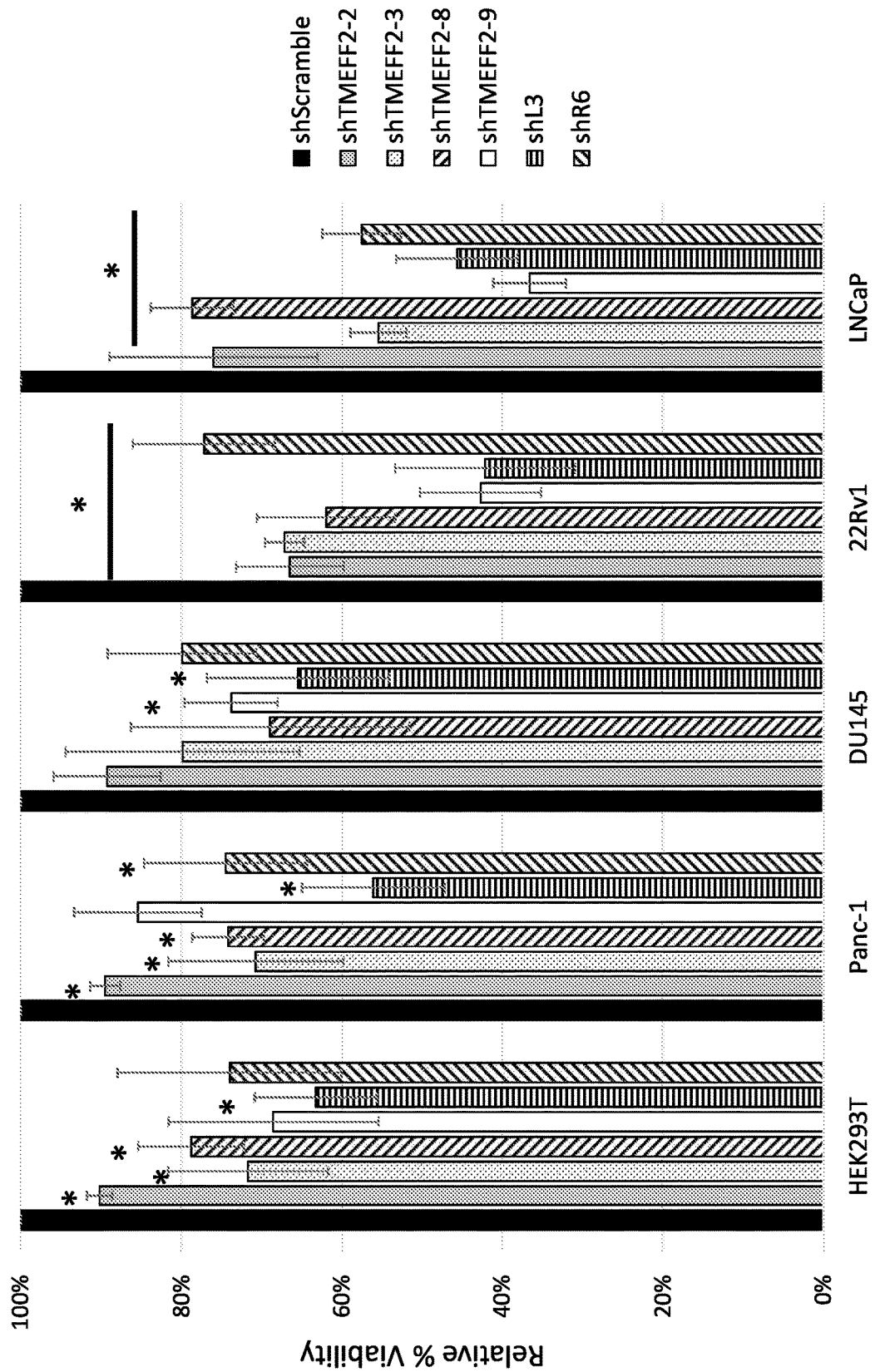
FIG. 4B is a bar graph showing percent viability of targeted shRNA relative to shScramble control in HEK293T, Panc-1, DU145, 22Rv1 and LNCaP cell lines. N=3, error bars±SD, *p<0.05, as calculated by two tailed T-test. TMEFF2-targeted shRNA are toxic to transformed cells, and toxicity correlates with reduced expression of androgen responsive genes in LNCaP cells.
Figure 4C:
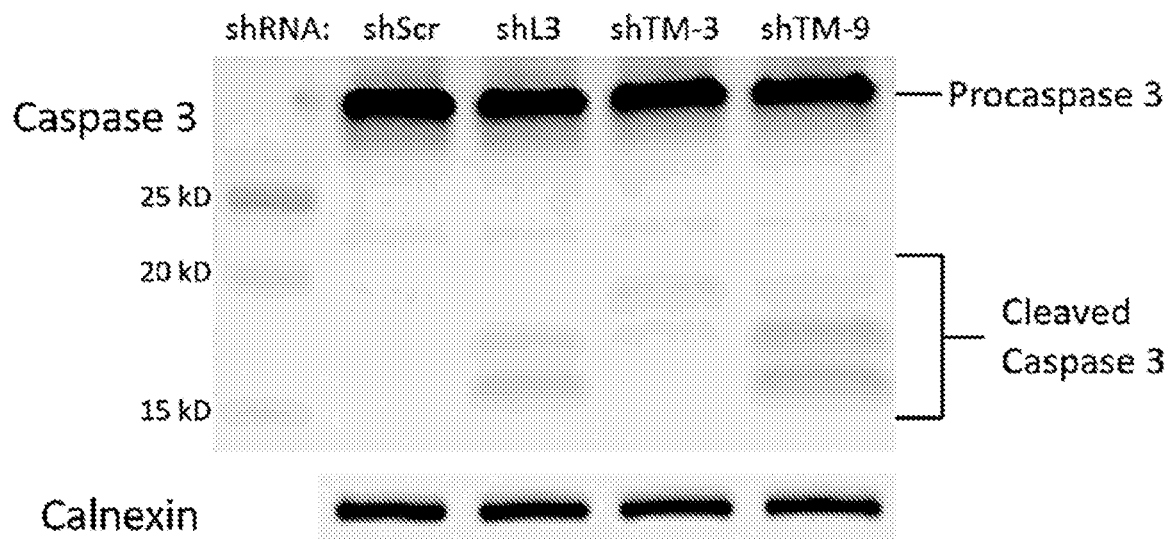
FIG. 4C depicts a Western blot analysis showing pro-caspase 3 and cleaved caspase 3 levels in response to shRNA 4 days after transductions in LNCaP cells (upper panel), and a graph showing that relative % Caspase 3 cleavage (cleaved caspase 3/procaspase 3), as determined using Biorad Image Lab, correlates with relative viability detected for shRNA expressing LNCaP cell lines (lower panel).
Figure 4C:
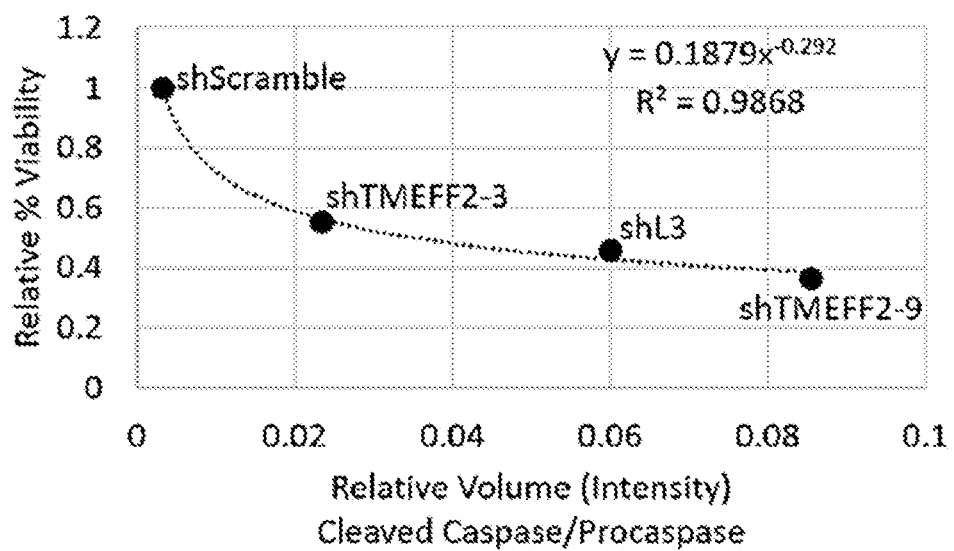
Figure 4D:
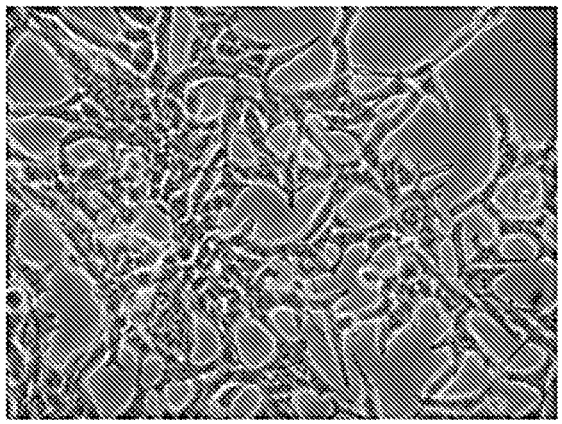
FIG. 4D shows representative micrograph images demonstrating cell morphology in four LNCaP shRNA cell lines 4 days after transductions.
Figure 4D:
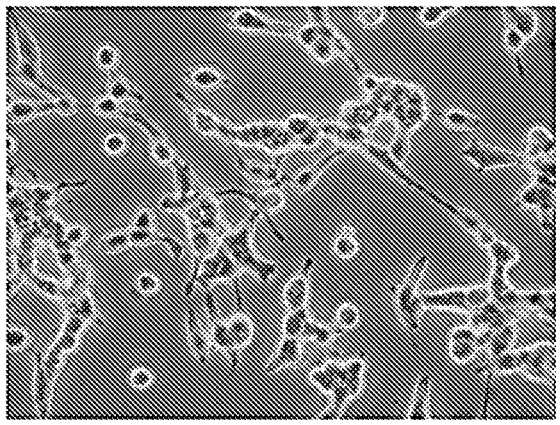
Figure 4D:
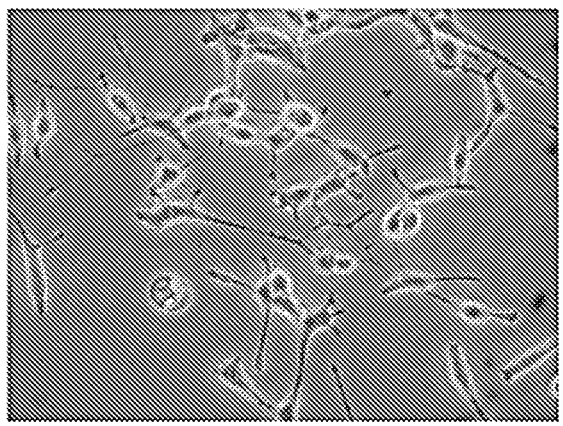
Figure 4D:
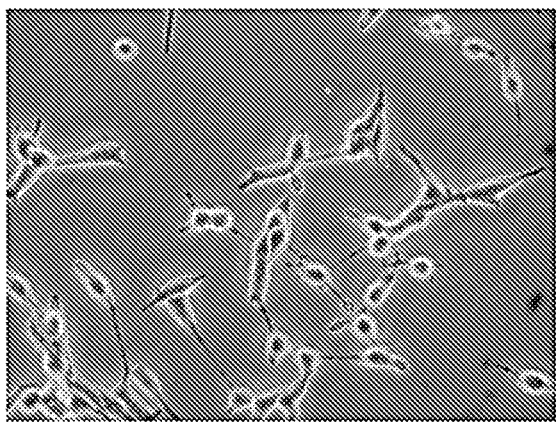

TMEFF2 shRNAs are Toxic to Transformed Cells and Sensitivity in LNCaP Cells Correlates With Lower Expression of AR Regulated Genes To further characterize the toxicity elicited by TMEFF2-targeted shRNA, we analyzed the growth and viability of multiple transformed cell lines in response to four TMEFF2-targeted shRNAs (shTMEFF2-2, shTMEFF2-3, shTMEFF2-8 and shTMEFF2-9) and two shRNAs previously shown to induce DISE (shL3 targeting CD95L and shR6 targeting CD95), in comparison to shScramble control. For these experiments, we selected two AR positive PCa cell lines, 22Rv1 (CRPC) and LNCaP (ADPC), and three transformed cell lines of different origin, HEK293T (transformed embryonic kidney), Panc-1 (pancreatic carcinoma) and DU145 (AR negative CRPC). Of note, DU145 and Panc-1 cell lines express little to no TMEFF2 (data shown in FIG. S1A of U.S. Provisional application Ser. No. 62/935,521). All of the targeted shRNAs tested significantly reduced the growth and viability of transformed cells, with few exceptions, when compared to shScramble control cells (data shown in FIGS. 4A-B herein, and in S7A of U.S. Provisional application Ser. No. 62/935,521), which maintained high viability percentage in all cell lines tested (70%-86%) (data shown in FIG. S7B of U.S. Provisional application Ser. No. 62/935,521); however, two of the most toxic TMEFF2-targeted shRNAs in LNCaP cells did not significantly affect the viability of RWPE1 cells, a benign prostate epithelial cell line, while shL3 resulted in only a 15% reduction in viability compared to RWPE1 shScramble cells (data shown in FIG. S7C of U.S. Provisional application Ser. No. 62/935,521), in agreement to previous reports that DISE inducing shRNAs are non-toxic to normal cells. Using LNCaP cells expressing shL3, shTMEFF2-3 and shTMEFF2-9 as examples, toxic shRNAs induced a similar rounded cell morphology with long thin extensions (FIG. 4D), as well as, Caspase-3 cleavage as measured by western blot, indicative of cell stress and apoptosis activation; furthermore, the level of Caspase-3 cleavage correlated with reduction in measured viability in LNCaP cells (FIG. 4C).

Since multiple shRNAs targeting TMEFF2 inhibited androgen signaling and induced similar toxicity to DISE-inducing shRNAs, we investigated whether all nine TMEFF2-targeted shRNAs contain seed sequences with predicted toxicity using an in silico scoring system generated by Putzbach et al., 2017 (Putzbach, W., Gao. Q Q., Pate, I M., van Dongen, S., Haluck-Kangas, A., Sarshad, A. A., Bartom, E. T., Kim, K. A., Scholten, s D. M., Hafner, M., Zhao, J. C., Murmann, A E., Peter, M. E. *Many si/shRNAs can kill cancer cells by targeting multiple survival genes through an off-target mechanism*. Elife. 2017; 6. Epub 2017/10/25) based on seed complementarity to the 3' UTR of essential genes vs nonessential genes, and using an in vitro seed toxicity screen data from Gao et al., 2018 (Gao Q Q, Putzbach W E, Murmann A E, Chen S, Sarshad A A, Peter J M, Bartom E T, Hafner M, Peter M E. *6mer seed toxicity in tumor suppressive microRNAs*. Nat Commun. 2018 Oct. 29; 9(1):4504). All possible 6mer seed sequences were analyzed in both sequence-based and viability analyses, and all possible 8mer seed sequences were also analyzed in sequence-based analyses. All seeds were rank ordered for the number of complementary sequences in essential survival gene 3' UTRs, toxicity index (normalized # of sequences in essential genes divided normalized # of sequences in a list of non-essential genes) and percent viability. TMEFF2-targeted shRNA seed sequences within the passenger and guide strands were consistently high percentile for the number of complementary sequences to essential genes (median percentile rank: 77.5, $3^{rd}$ quartile rank: 91) (data shown in Table S5A and Appendix 1 of U.S. Provisional application Ser. No. 62/935,521), while 6mer toxic seeds, as predicted from the viability screen, were mostly located in the guide strand (median percentile rank: 69, $3^{rd}$ quartile rank: 90) (data shown in Table S5B and Appendix 1 of U.S. Provisional application Ser. No. 62/935, 521). While the viability screens did not include PCa cells, these data support our findings that TMEFF2 targeted shRNAs contain toxic seed sequences that induce DISE in transformed cells.

When comparing viability effects of the six toxic shRNAs across cell lines, we noticed a trend of higher toxicity in the two AR+PCa compared to the three other transformed cell lines, with shTMEFF2-9 demonstrating the most dramatic difference (data shown in FIG. S7D of U.S. Provisional application Ser. No. 62/935,521). Since shRNAs targeting TMEFF2 inhibit androgen signaling, a critical survival pathway in these cells, we next determined the effect of the four shTMEFF2 and shL3/shR6 shRNAs on androgen responsive gene expression in LNCaP cells. All six shRNAs, with few exceptions, significantly reduced the expression of four androgen responsive transcripts often used as surrogates for AR activity, KLK3, KLK2, NKX3-1 and TMPRSS2, when compared to shScramble control LNCaP cells 48 hours to 72 hours after shRNA transductions (data shown in FIG. 6D of U.S. Provisional application Ser. No. 62/935,521). Both shTMEFF2-3 and shTMEFF2-9, two of the more toxic shRNAs in LNCaP cells, demonstrated significantly more potent reductions in androgen responsive gene expression when compared to shTMEFF2-2, shTMEFF2-8 and shL3 (data shown in FIG. 6D of U.S. Provisional application Ser. No. 62/935,521). Additionally, the level of androgen responsive gene reduction for each shRNA significantly correlated with relative viability reduction in LNCaP cells compared to the three AR-independent transformed cell lines tested (HEK293T, Panc-1 and DU145) (data shown in FIG. 6E of U.S. Provisional application Ser. No. 62/935,521). These data demonstrate a relationship between the effect of toxic shRNA-mediated androgen signaling inhibition, likely through the depletion of AR and/or AR coregulators as demonstrated with shTMEFF2-3, and toxicity in AR+PCa cells.

Identification of AR Coregulators by Complementarity to the shRNA

The following procedure can be carried out to identify AR coregulators whose expression is affected by shRNAs or have one or more sequences in the 3'-UTR that can be target by the shRNA: (1) Cells are transfected with each one of the shRNAs to be tested and with a control; (2) RNA-Seq is carried out to determine which genes are affected by each of the tested shRNAs (mRNA level increase or decrease with respect to the control); (3) The genes that are affected by each specific shRNA are identified and compared to a list of AR-coregulators; (4) Also, the 3'-UTR of all of the AR-coregulator mRNAs are searched (independently of whether their expression is changed or not based on the RNA-Seq data) for sequences that are complementary to the seed sequence of the tested shRNAs. If those sequences are present in any or more of the AR-coregulator's 3'-UTR, that would suggest that those specific AR-coregulators are targets for that particular shRNA; (5) Genes that are downregulated and contain one or more sequences complementary to the seed sequence of the specific shRNA would be bona fide targets.

In each of Tables 2, 3 and 4, (shTMEFF2-3, shTMEFF2-4 and shTMEFF2-9), there are 3 columns. The righthand column lists AR-coregulators that are definitely targets of the specific shRNA. The lefthand column lists AR-coregulators whose expression is not affected by the shRNA as seen in the RNA-Seq results, but which have one sequence in its 3'-UTR that can be target by the tested shRNA. The center column lists AR-coregulators whose expression is not affected by the shRNA as seen in the RNA-Seq results, but which have more than one sequence in their 3'-UTR that can be targeted by the tested shRNA.

TABLE 2

AR coregulators downregulated by or having binding sites (single or multiple) to shTMEFF2-3

| Single | Multiple | Downregulated |
| --- | --- | --- |
| AKT1 | ACTN2 | ADAM10 |
| ARID5A | ARHGDIA | APPBP2 |
| ATXN7L3 | ARID1A | CCND3 |
| BRCA2 | ARRB2 | CDK7 |
| CDC25A | BRCA1 | CTDSP2 |
| CDC25B | CBX1 | FKBP5 |
| CDK6 | CCND1 | HELZ2 |
| DDC | CREBBP | MED1 |
| DYRK1A | DDX17 | PER1 |
| EGFR | FKBP4 | PIAS1 |
| ENY2 | HDAC3 | PIK3CB |
| FHL2 | HDAC4 | RANBP10 |
| GSK3B | IL6ST | TAF1 |
| GSN | KAT2B | TPD52 |
| HEY1 | MAGEA11 | YWHAH |
| HIP1 | NCOA3 | |
| HSP90AA1 | NCOA6 | |
| HSPA4 | NRIP1 | |
| HTATIP2 | NSD1 | |
| IDE | PATZ1 | |
| IRS1 | PIAS2 | |
| JMJD1C | PPARGC1A | |
| KAT7 | PSPC1 | |
| KDM4C | RBAK | |

TABLE 2-continued

AR coregulators downregulated by or having binding sites (single or multiple) to shTMEFF2-3

| Single | Multiple | Downregulated |
|---|---|---|
| KDM5B | RBM14 | |
| KHDRBS1 | RCHY1 | |
| KIF1A | RNF4 | |
| MAK | SENP1 | |
| MAPK1 | SMAD3 | |
| MED24 | SMAD4 | |
| MYO6 | SMARCC1 | |
| NCOA1 | STAT5B | |
| NCOA2 | TCF4 | |
| NCOA4 | WDR77 | |
| NCOR1 | | |
| NONO | | |
| PRKD1 | | |
| PRMT2 | | |
| PSMC3IP | | |
| PXN | | |
| RPS6KA3 | | |
| SFN | | |
| SFPQ | | |
| SMAD1 | | |
| SOD2 | | |
| SORBS3 | | |
| SRA1 | | |
| SRC | | |
| SRCAP | | |
| SUMO2 | | |
| SUMO3 | | |
| SVIL | | |
| TDG | | |
| TOB2 | | |
| TRIM68 | | |
| UBE2I | | |
| UBE2L3 | | |
| UBE3A | | |
| VAV3 | | |
| ZMIZ1 | | |
| ZNF318 | | |
| ZNF451 | | |

TABLE 3

AR coregulators downregulated by or having binding sites (single or multiple) to shTMEFF2-4

| Single | Multiple | Downregulated |
|---|---|---|
| RCHY1 | CREBBP | FKBP5 |
| TPD52 | PXN | CTDSP2 |
| HEY1 | ATXN7L3 | RANBP10 |
| HAP1 | MAK | BRCA1 |
| VAV3 | KIF1A | CALM1 |
| CASP8 | PMEPA1 | CALR |
| TCF4 | PIK3CB | CCND1 |
| DDX17 | ZNF451 | CDC25A |
| CCND3 | DYRK1A | CTNNB1 |
| SMAD3 | MDM2 | EHMT2 |
| GSK3B | STAT3 | FKBP4 |
| CHD8 | SMAD4 | IDE |
| BAG1 | IRS1 | KAT2B |
| KAT7 | AATF | MAPK1 |
| KAT5 | USP22 | PIK3R1 |
| PRMT2 | ZMIZ1 | PSMC3IP |
| HIP1 | CCAR2 | RPS6KA1 |
| UBE2L3 | ARRB2 | RPS6KA3 |
| CDK9 | | SMAD1 |
| EP300 | | |
| PPP1CC | | |
| UBE2I | | |
| KMT2D | | |
| NRIP1 | | |
| TRIM24 | | |
| MED17 | | |

TABLE 3-continued

AR coregulators downregulated by or having binding sites (single or multiple) to shTMEFF2-4

| Single | Multiple | Downregulated |
|---|---|---|
| MED1 | | |
| SFPQ | | |
| USP10 | | |
| EGFR | | |
| STUB1 | | |
| HDAC4 | | |
| DNAJB1 | | |
| POU4F1 | | |
| ANP32A | | |
| CDC37 | | |
| LATS2 | | |
| KDM4A | | |
| TRIM68 | | |
| PAK6 | | |
| KAT2A | | |
| NSD1 | | |
| CALCOCO1 | | |
| PRMT1 | | |
| PPP2R1A | | |
| PSPC1 | | |
| SENP1 | | |

TABLE 4

AR coregulators downregulated by or having binding sites (single or multiple) to shTMEFF2-9

| Single site | Multiple sites | Downregulated |
|---|---|---|
| HSP90AA1 | SMAD1 | ADAM10 |
| SRA1 | HDAC7 | APPBP2 |
| HAP1 | SMARCA4 | BAG1 |
| TCF4 | SMAD3 | CALM1 |
| DDX17 | ENY2 | CDK2AP1 |
| ATXN7L3 | KMT2D | FKBP5 |
| SIRT1 | NRIP1 | GSK3B |
| KDM4C | SMAD4 | HIP1 |
| NCOA3 | CTDSP2 | HIPK3 |
| KMT2A | HDAC4 | IL6ST |
| RBM14 | PIAS2 | KAT2B |
| KAT5 | PSPC1 | MAPK1 |
| PIK3R1 | BRCA1 | MED1 |
| PPP1CC | SENP1 | MED21 |
| ZNF451 | | MKRN1 |
| CDK9 | | NCOA2 |
| DYRK1A | | PMEPA1 |
| FKBP4 | | PRMT2 |
| MDM2 | | RANBP9 |
| NPM1 | | RPS6KA3 |
| SFRP1 | | SMARCD1 |
| TDG | | UBE2L3 |
| TGIF1 | | ZMIZ1 |
| UBE2I | | |
| NCOA1 | | |
| UXT | | |
| MED14 | | |
| MYO6 | | |
| DNAJB1 | | |
| KHDRBS1 | | |
| TMF1 | | |
| STAT5B | | |
| PATZ1 | | |
| PSIP1 | | |
| CCAR2 | | |

Identification of AR Coregulators by Analysis of Copy Number Alterations (CNA)

Androgen receptor (AR)-mediated transcription is dependent on the recruitment of AR coregulators, which modulate its transcriptional response. Expression of AR coregulators is usually de-regulated in prostate cancer (PCa), and generally increased expression correlate with aggressive disease and poor clinical outcome. Studies on AR signaling during PCa progression have indicated that: 1) aberrant expression of coregulators is one of the mechanisms that leads to therapeutic resistance; 2) specific coregulators control the expression of subsets of AR target genes, and 3) the AR drives a distinct transcriptional program in advanced CRPC. Accordingly, some coregulators promote AR signaling in low androgen conditions, such as under androgen-deprivation therapy (ADT), or in CRPC. We subjected a list of 274 AR coregulators (reported to modulate AR transcriptional output) to analysis of copy number alterations (CNA) in multiple clinical cohorts of metastatic prostate cancer (PCa) extracted from cBioportal for cancer genomics. The analysis was carried out in three different cohorts, and specific coregulators were selected if their copy number was increased in at least 10% of the patients. We observed 21, 14 and 8 genes with high copy number in the Fred Hutchinson CRC dataset (Kumar, A., Coleman, I., Morrissey, C., Zhang, X., True, L. D., Gulati, R., Etzioni, R., Bolouri, H., Montgomery, B., White, T., et al., 2016, Substantial interindividual and limited intraindividual genomic diversity among tumors from men with metastatic prostate cancer. Nat. Med. 22, 369-378), the SU2/PCF Dream Team dataset (Abida, W., Cyrta, J., Heller, G., Prandi, D., Armenia, J., Coleman, I., . . . Sawyers, C. L., 2019, Genomic correlates of clinical outcome in advanced prostate cancer. *Proceedings of the National Academy of Sciences of the United States of America*, 116(23), 11428-11436. doi:10.1073/pnas.1902651116); and the University of Michigan dataset (Grasso, C. S., Wu, Y. M., Robinson, D. R., Cao, X., Dhanasekaran, S. M., Khan, A. P., Tomlins, S. A., 2012, The mutational landscape of lethal castration-resistant prostate cancer. Nature, 487(7406), 239-243. doi:10.1038/nature11125). Twelve of the genes were in common for the first two datasets and those included the 8 amplified in the University of Michigan dataset. These results indicate that these 12 genes have a role in advanced disease: ATAD2, CCND1, COPS5, ENY2, HEY1, MAPK15, NCOA2, PQBP1, PRKDC, RPS6KA3, TPD52, UXT.

Seed Sequences of Interfering RNAs

Examples of RNA oligomers that can be used in accordance with the present disclosure to treat prostate cancer include, but are not limited to, RNAs such as the 5'-3' sequences in Tables 5 and 8 below, which comprise 6-mer "seed" sequences that bind to target AR coregulator nucleic acids. The RNAs may be single-stranded or may be double stranded and include the complementary strand. The 6-mer seed sequence portions of the sequences that are underlined in Table 5 are specifically shown in Table 6. DNA equivalents of the sequences in Table 6 below (i.e., where U is replaced with T) may also be used in certain embodiments of the present disclosure, for example as shown in Table 9.

TABLE 5

| Interfering RNA sequences* | | |
|---|---|---|
| siTMEFF2-1 | CUCUGUCAUC AUAACCAGA | SEQ ID NO: 16 |
| siTMEFF2-2 | CACUUGAACU GACAGACGC | SEQ ID NO: 17 |
| siTMEFF2-3 | AUUUCCCAUC AGAAGCGCA | SEQ ID NO: 18 |
| siTMEFF2-4 | AACCAGCAUC ACACCUGCA | SEQ ID NO: 19 |

TABLE 5-continued

| Interfering RNA sequences* | | |
|---|---|---|
| siTMEFF2-5 | AUUACCACAA AUGCAAGGC | SEQ ID NO: 20 |
| siTMEFF2-6 | ACUAGUUUCU CCAGAGCCU | SEQ ID NO: 21 |
| siTMEFF2-7 | UGUUAGCAUU CUCUGCAUA | SEQ ID NO: 22 |
| siTMEFF2-8 | UGUUCCGGAC AAGGUAUGU | SEQ ID NO: 23 |
| siTMEFF2-9 | UGUCUGAACU GUAGUGCCC | SEQ ID NO: 24 |
| miR-634 | AACCAGCACC CCAACUUUGG AC | SEQ ID NO: 25 |
| miR-4446-5p | AUUUCCCUGC CAUUCCCUUG GC | SEQ ID NO: 26 |
| miR-6888-3p | AUCUGUCUCG AUUGUUUCCA G | SEQ ID NO: 27 |

*6-mer seed sequence portions of the sequences are underlined

TABLE 6

| 6-mer seed sequences of source siRNA sequences of Table 5 | |
|---|---|
| siTMEFF2-1 | UCUGUC |
| siTMEFF2-2 | ACUUGA |
| siTMEFF2-3 | UUUCCC |
| siTMEFF2-4 | ACCAGC |
| siTMEFF2-5 | UUACCA |
| siTMEFF2-6 | CUAGUU |
| siTMEFF2-7 | GUUAGC |
| siTMEFF2-8 | GUUCCG |
| siTMEFF2-9 | GUCUGA |
| miR-634 | ACCAGC |
| miR-4446-5p | UUUCCC |
| miR-6888-3p | UCUGUC |

Figure 5:
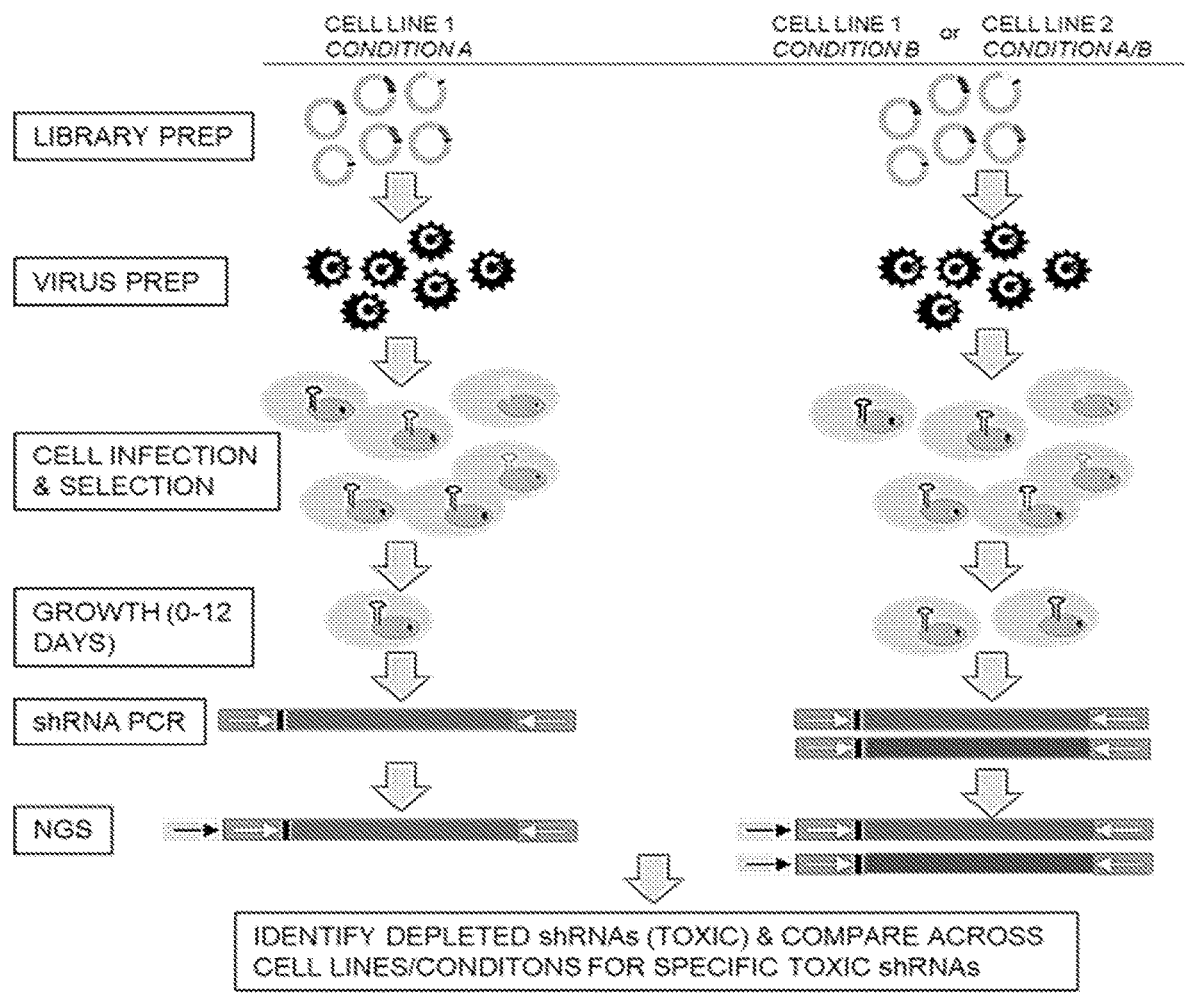
FIG. 5 is a schematic showing a strategy for a negative selection screen with pooled shRNAs to validate and optimize identification of toxic seed sequences.

Table 7 shows generic 10-mer sequences which contain, after a first generic nucleotide, a 6-mer seed sequences for RNA or DNA oligonucleotides, where X=U or T or other pyrimidine nucleobases as described elsewhere herein, followed by 3 additional generic nucleotides. The 10-mer sequence can comprise portions of larger oligonucleotides (e.g., 12-50 nucleotides) in the therapeutic nucleic acid compounds of the present disclosure. Also included are complementary sequences. Generic, RNA, and DNA versions of toxic seed sequences identified through the large-scale viability screening procedure shown in FIG. 5 are included in Tables 7, 8 and 9, respectively.

TABLE 7

Generic oligonucleotides with 6-mer seed sequences *

| Sequence | SEQ ID NO: | Nucleobase Alternatives |
|---|---|---|
| $X_1\underline{X_2CX_3GX_4C}X_5X_6X_7$ | SEQ ID NO: 28 | $X_1$, $X_5$, $X_6$, $X_7$ = C, G, U, A or T ** <br> $X_2$–$X_4$ = U or T*** |
| $X_1\underline{ACX_2X_3GA}X_4X_5X_6$ | SEQ ID NO: 29 | $X_1$, $X_4$, $X_5$, $X_6$ = C, G, U, A or T ** <br> $X_2$–$X_3$ = U or T*** |
| $X_1\underline{X_2X_3X_4CCC}X_5X_6X_7$ | SEQ ID NO: 30 | $X_1$, $X_5$, $X_6$, $X_7$ = C, G, U, A or T ** <br> $X_2$–$X_4$ = U or T*** |
| $X_1\underline{ACCAGC}X_2X_3X_4$ | SEQ ID NO: 31 | C, G, U, A or T ** |
| $X_1\underline{X_2X_3ACCA}X_4X_5X_6$ | SEQ ID NO: 32 | $X_1$, $X_4$, $X_5$, $X_6$ = C, G, U, A or T ** <br> $X_2$–$X_3$ = U or T*** |
| $X_1\underline{CX_2AGX_3}X_4X_5X_6X_7$ | SEQ ID NO: 33 | $X_1$, $X_5$, $X_6$, $X_7$ = C, G, U, A or T ** <br> $X_2$–$X_4$ = U or T*** |
| $X_1\underline{GX_2X_3AGC}X_4X_5X_6$ | SEQ ID NO: 34 | $X_1$, $X_4$, $X_5$, $X_6$ = C, G, U, A or T ** <br> $X_2$–$X_3$ = U or T*** |
| $X_1\underline{GX_2X_3CCG}X_4X_5X_6$ | SEQ ID NO: 35 | $X_1$, $X_4$, $X_5$, $X_6$ = C, G, U, A or T ** <br> $X_2$–$X_3$ = U or T*** |
| $X_1\underline{GX_2CX_3GA}X_4X_5X_6$ | SEQ ID NO: 36 | $X_1$, $X_4$, $X_5$, $X_6$ = C, G, U, A or T ** <br> $X_2$–$X_3$ = U or T*** |
| $X_1\underline{X_2CCX_3GX_4}X_5X_6X_7$ | SEQ ID NO: 37 | $X_1$, $X_5$, $X_6$, $X_7$ = C, G, U, A or T ** <br> $X_2$–$X_4$ = U or T*** |
| $X_1\underline{X_2ACX_3GG}X_4X_5X_6$ | SEQ ID NO: 38 | $X_1$, $X_4$, $X_5$, $X_6$ = C, G, U, A or T ** <br> $X_2$–$X_3$ = U or T*** |
| $X_1\underline{AX_2CX_3GX_4}X_5X_6X_7$ | SEQ ID NO: 39 | $X_1$, $X_5$, $X_6$, $X_7$ = C, G, U, A or T ** <br> $X_2$–$X_4$ = U or T*** |
| $X_1\underline{X_2X_3GCAG}X_4X_5X_6$ | SEQ ID NO: 40 | $X_1$, $X_4$, $X_5$, $X_6$ = C, G, U, A or T ** <br> $X_2$–$X_3$ = U or T*** |
| $X_1\underline{X_2CCX_3GG}X_4X_5X_6$ | SEQ ID NO: 41 | $X_1$, $X_4$, $X_5$, $X_6$ = C, G, U, A or T ** <br> $X_2$–$X_3$ = U or T*** |
| $X_1\underline{ACX_2GAC}X_3X_4X_5$ | SEQ ID NO: 42 | $X_1$, $X_3X_4$, $X_5$ = C, G, U, A or T ** <br> $X_2$ = U or T*** |
| $X_1\underline{CCAGCC}X_2X_3X_4$ | SEQ ID NO: 43 | $X_1$–$X_4$ = C, G, U, A or T ** |
| $X_1\underline{X_2ACACC}X_3X_4X_5$ | SEQ ID NO: 44 | $X_1$, $X_3X_4$, $X_5$ = C, G, U, A or T ** <br> $X_2$ = U or T*** |
| $X_1\underline{AAGX_2AC}X_3X_4X_5$ | SEQ ID NO: 45 | $X_1$, $X_3X_4$, $X_5$ = C, G, U, A or T ** <br> $X_2$ = U or T*** |
| $X_1\underline{X_2AAGX_3A}X_4X_5X_6$ | SEQ ID NO: 46 | $X_1$, $X_4$, $X_5$, $X_6$ = C, G, U, A or T ** <br> $X_2$–$X_3$ = U or T*** |
| $X_1\underline{CCX_2GGC}X_3X_4X_5$ | SEQ ID NO: 47 | $X_1$, $X_3X_4$, $X_5$ = C, G, U, A or T ** <br> $X_2$ = U or T*** |
| $X_1\underline{ACCX_2GG}X_3X_4X_5$ | SEQ ID NO: 48 | $X_1$, $X_3X_4$, $X_5$ = C, G, U, A or T ** <br> $X_2$ = U or T*** |
| $X_1\underline{GCAGGX_2}X_3X_4X_5$ | SEQ ID NO: 49 | $X_1$, $X_3X_4$, $X_5$ = C, G, U, A or T ** <br> $X_2$ = U or T*** |
| $X_1\underline{X_2GCAGG}X_3X_4X_5$ | SEQ ID NO: 50 | $X_1$, $X_3X_4$, $X_5$ = C, G, U, A or T ** <br> $X_2$ = U or T*** |
| $X_1\underline{GACX_2X_3G}X_4X_5X_6$ | SEQ ID NO: 51 | $X_1$, $X_4$, $X_5$, $X_6$ = C, G, U, A or T ** <br> $X_2$–$X_3$ = U or T*** |
| $X_1\underline{GAX_2GCC}X_3X_4X_5$ | SEQ ID NO: 52 | $X_1$, $X_3X_4$, $X_5$ = C, G, U, A or T ** <br> $X_2$ = U or T*** |
| $X_1\underline{X_2AAGGC}X_3X_4X_5$ | SEQ ID NO: 53 | $X_1$, $X_3X_4$, $X_5$ = C, G, U, A or T ** <br> $X_2$ = U or T*** |

TABLE 7-continued

Generic oligonucleotides with 6-mer seed sequences *

| Sequence | SEQ ID NO: | Nucleobase Alternatives |
|---|---|---|
| X$_1$X$_2$GAX$_3$AGX$_4$X$_5$X$_6$ | SEQ ID NO: 54 | X$_1$, X$_4$, X$_5$, X$_6$ = C, G, U, A or T <br>X$_2$-X$_3$ = U or T* |
| X$_1$X$_2$X$_3$AGCCX$_4$X$_5$X$_6$ | SEQ ID NO: 55 | X$_1$, X$_4$, X$_5$, X$_6$ = C, G, U, A or T <br>X$_2$-X$_3$ = U or T* |
| X$_1$X$_2$GX$_3$X$_4$X$_5$AX$_6$X$_7$X$_8$ | SEQ ID NO: 56 | X$_1$, X$_6$X$_7$, X$_8$ = C, G, U, A or T <br>X$_2$-X$_5$ = U or T* |
| X$_1$X$_2$X$_3$CGGCX$_4$X$_5$X$_6$ | SEQ ID NO: 57 | X$_1$, X$_4$, X$_5$, X$_6$ = C, G, U, A or T <br>X$_2$-X$_3$ = U or T* |
| X$_1$X$_2$ACX$_3$GX$_4$X$_5$X$_6$X$_7$ | SEQ ID NO: 58 | X$_1$, X$_5$, X$_6$, X$_7$ = C, G, U, A or T <br>X$_2$-X$_4$ = U or T* |
| X$_1$X$_2$ACX$_3$GAX$_4$X$_5$X$_6$ | SEQ ID NO: 59 | X$_1$, X$_4$, X$_5$, X$_6$ = C, G, U, A or T <br>X$_2$-X$_3$ = U or T* |
| X$_1$GX$_2$GX$_3$GX$_4$X$_5$X$_6$X$_7$ | SEQ ID NO: 60 | X$_1$, X$_5$, X$_6$, X$_7$ = C, G, U, A or T <br>X$_2$-X$_4$ = U or T* |
| X$_1$AX$_2$GX$_3$ACX$_4$X$_5$X$_6$ | SEQ ID NO: 61 | X$_1$, X$_4$, X$_5$, X$_6$ = C, G, U, A or T <br>X$_2$-X$_3$ = U or T* |
| X$_1$X$_2$AX$_3$CAX$_4$X$_5$X$_6$X$_7$ | SEQ ID NO: 62 | X$_1$, X$_5$, X$_6$, X$_7$ = C, G, U, A or T <br>X$_2$-X$_4$ = U or T* |
| X$_1$GAX$_2$AGAX$_3$X$_4$X$_5$ | SEQ ID NO: 63 | X$_1$, X$_3$X$_4$, X$_5$ = C, G, U, A or T <br>X$_2$ = U or T* |

* 6-mer seed sequences are underlined
** or other modified nucleobases as described elsewhere herein
***or other pyrimidine nucleobases as described elsewhere herein.

Shown in Table 8 are examples of generic RNA oligonucleotides, comprising RNA versions of the generic 6-mer seed sequences of Table 7, for use in therapeutic treatments of the present disclosure. The RNA oligonucleotides represented may be single-stranded or may be a single strand of a double-stranded oligonucleotide. Also included are complementary sequences.

TABLE 8

Generic RNA oligonucleotide sequences with 6-mer seed sequences

| Sequence | SEQ ID NO: |
|---|---|
| xUCUGUCxxxxxxxxxxxxx | SEQ ID NO: 64 |
| xACUUGAxxxxxxxxxxxxx | SEQ ID NO: 65 |
| xUUUCCCxxxxxxxxxxxxx | SEQ ID NO: 66 |
| xACCAGCxxxxxxxxxxxxx | SEQ ID NO: 67 |
| xUUACCAxxxxxxxxxxxxx | SEQ ID NO: 68 |
| xCUAGUUxxxxxxxxxxxxx | SEQ ID NO: 69 |
| xGUUAGCxxxxxxxxxxxxx | SEQ ID NO: 70 |
| xGUUCCGxxxxxxxxxxxxx | SEQ ID NO: 71 |
| xGUCUGAxxxxxxxxxxxxx | SEQ ID NO: 72 |
| xUCCUGUxxxxxxxxxxxxx | SEQ ID NO: 73 |
| xUACUGGxxxxxxxxxxxxx | SEQ ID NO: 74 |
| xAUCUGUxxxxxxxxxxxxx | SEQ ID NO: 75 |
| xUUGCAGxxxxxxxxxxxxx | SEQ ID NO: 76 |
| xUCCUGGxxxxxxxxxxxxx | SEQ ID NO: 77 |
| xACUGACxxxxxxxxxxxxx | SEQ ID NO: 78 |
| xCCAGCCxxxxxxxxxxxxx | SEQ ID NO: 79 |
| xUACACCxxxxxxxxxxxxx | SEQ ID NO: 80 |
| xAAGUACxxxxxxxxxxxxx | SEQ ID NO: 81 |
| xUAAGUAxxxxxxxxxxxxx | SEQ ID NO: 82 |
| xCCUGGCxxxxxxxxxxxxx | SEQ ID NO: 83 |
| xACCUGGxxxxxxxxxxxxx | SEQ ID NO: 84 |
| xGCAGGUxxxxxxxxxxxxx | SEQ ID NO: 85 |
| xUGCAGGxxxxxxxxxxxxx | SEQ ID NO: 86 |
| xGACUUGxxxxxxxxxxxxx | SEQ ID NO: 87 |
| xGAUGCCxxxxxxxxxxxxx | SEQ ID NO: 88 |
| xUAAGGCxxxxxxxxxxxxx | SEQ ID NO: 89 |
| xUGAUAGxxxxxxxxxxxxx | SEQ ID NO: 90 |
| xUUAGCCxxxxxxxxxxxxx | SEQ ID NO: 91 |
| xUGUUUAxxxxxxxxxxxxx | SEQ ID NO: 92 |
| xUUCGGCxxxxxxxxxxxxx | SEQ ID NO: 93 |
| xUACUGUxxxxxxxxxxxxx | SEQ ID NO: 94 |

TABLE 8-continued

Generic RNA oligonucleotide sequences with 6-mer seed sequences

| | |
|---|---|
| xUACUGAxxxxxxxxxxxxx | SEQ ID NO: 95 |
| xGUGUGUxxxxxxxxxxxxx | SEQ ID NO: 96 |
| xAUGUACxxxxxxxxxxxxx | SEQ ID NO: 97 |
| xUAUCAUxxxxxxxxxxxxx | SEQ ID NO: 98 |
| xGAUAGAxxxxxxxxxxxxx | SEQ ID NO: 99 | x = C, G, U, or A, or other modified nucleobases as described elsewhere herein.

Shown in Table 9 are examples of generic DNA oligonucleotides, comprising DNA versions of the generic 6-mer seed sequences of Table 7, for use in therapeutic treatments of the present disclosure. The sequences comprise a strand of a double-stranded DNA oligonucleotide. Also included are complementary sequences.

TABLE 9

Generic DNA oligonucleotides with 6-mer seed sequences

| | |
|---|---|
| xTCTGTCxxxxxxxxxxxxx | SEQ ID NO: 100 |
| xACTTGAxxxxxxxxxxxxx | SEQ ID NO: 101 |
| xTTTCCCxxxxxxxxxxxxx | SEQ ID NO: 102 |
| xACCAGCxxxxxxxxxxxxx | SEQ ID NO: 67 |
| xTTACCAxxxxxxxxxxxxx | SEQ ID NO: 103 |
| xCTAGTTxxxxxxxxxxxxx | SEQ ID NO: 104 |
| xGTTAGCxxxxxxxxxxxxx | SEQ ID NO: 105 |
| xGTTCCGxxxxxxxxxxxxx | SEQ ID NO: 106 |
| xGTCTGAxxxxxxxxxxxxx | SEQ ID NO: 107 |
| xTCCTGTxxxxxxxxxxxxx | SEQ ID NO: 108 |
| xTACTGGxxxxxxxxxxxxx | SEQ ID NO: 109 |
| xATCTGTxxxxxxxxxxxxx | SEQ ID NO: 110 |
| xTTGCAGxxxxxxxxxxxxx | SEQ ID NO: 111 |
| xTCCTGGxxxxxxxxxxxxx | SEQ ID NO: 112 |
| xACTGACxxxxxxxxxxxxx | SEQ ID NO: 113 |
| xCCAGCCxxxxxxxxxxxxx | SEQ ID NO: 114 |
| xTACACCxxxxxxxxxxxxx | SEQ ID NO: 115 |
| xAAGTACxxxxxxxxxxxxx | SEQ ID NO: 116 |
| xTAAGTAxxxxxxxxxxxxx | SEQ ID NO: 117 |
| xCCTGGCxxxxxxxxxxxxx | SEQ ID NO: 118 |
| xACCTGGxxxxxxxxxxxxx | SEQ ID NO: 119 |
| xGCAGGTxxxxxxxxxxxxx | SEQ ID NO: 120 |
| xTGCAGGxxxxxxxxxxxxx | SEQ ID NO: 121 |
| xGACTTGxxxxxxxxxxxxx | SEQ ID NO: 122 |
| xGATGCCxxxxxxxxxxxxx | SEQ ID NO: 123 |

TABLE 9-continued

Generic DNA oligonucleotides with 6-mer seed sequences

| | |
|---|---|
| xTAAGGCxxxxxxxxxxxxx | SEQ ID NO: 124 |
| xTGATAGxxxxxxxxxxxxx | SEQ ID NO: 125 |
| xTTAGCCxxxxxxxxxxxxx | SEQ ID NO: 126 |
| xTGTTTAxxxxxxxxxxxxx | SEQ ID NO: 127 |
| xTTCGGCxxxxxxxxxxxxx | SEQ ID NO: 128 |
| xTACTGTxxxxxxxxxxxxx | SEQ ID NO: 129 |
| xTACTGAxxxxxxxxxxxxx | SEQ ID NO: 130 |
| xGTGTGTxxxxxxxxxxxxx | SEQ ID NO: 131 |
| xATGTACxxxxxxxxxxxxx | SEQ ID NO: 132 |
| xTATCATxxxxxxxxxxxxx | SEQ ID NO: 133 |
| xGATAGAxxxxxxxxxxxxx | SEQ ID NO: 134 | x = C, G, T, or A, or other modified nucleobases as described elsewhere herein.

Discussion

As is the case for many malignancies, therapy resistance is a major cause of PCa-related morbidities and mortalities. Androgen deprivation therapy often gives rise to AR positive or AR negative CRPC, which represent two subclasses of resistant disease in which genetic, epigenetic, RNA splicing and other molecular aberrations contribute to either sustained androgen signaling or complete independence from the AR. These adaptive resistance mechanisms pose grave challenges to the effective treatment and management of this disease, underscoring the importance for the development of novel therapeutic agents and strategies.

Figure 6:
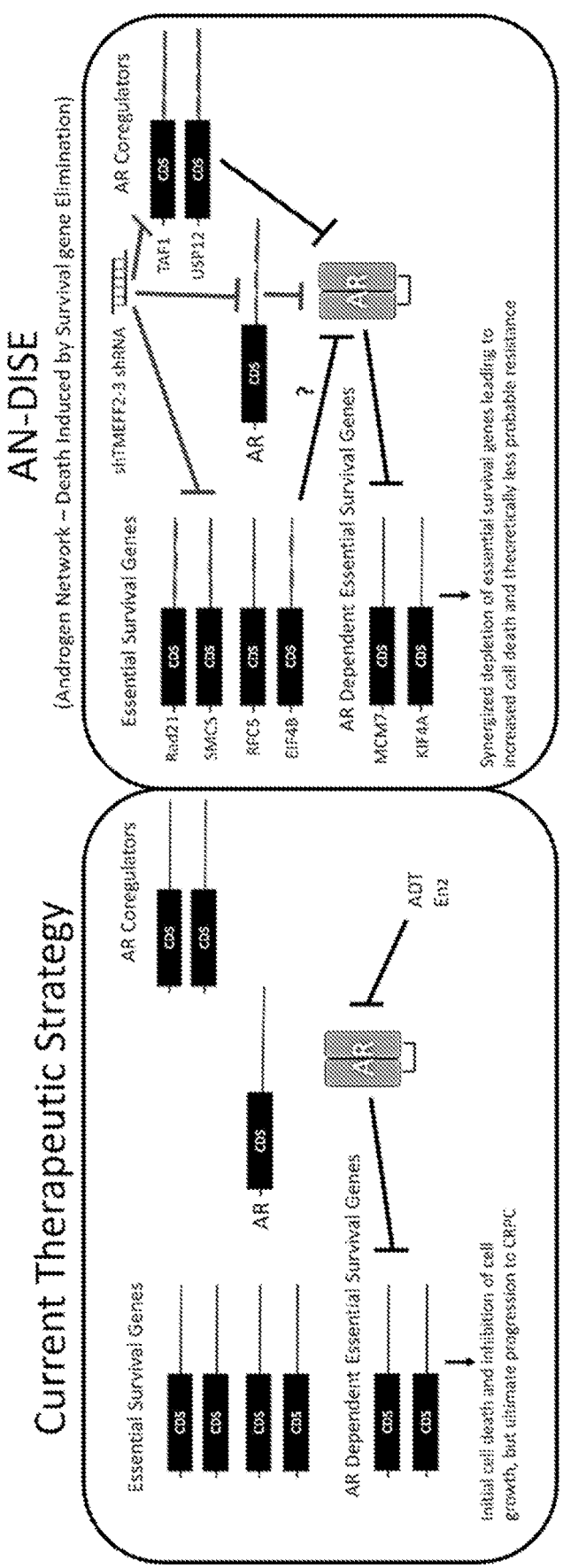
FIG. 6 is a schematic showing a comparison of the conventional AR-inhibitory therapeutic strategy with the Androgen Network-Death Induced by Survival gene Elimination (AN-DISE) strategy disclosed herein. Left panel: Current FDA approved therapeutic approaches in prostate cancer target androgen signaling either by inhibiting global androgen production (androgen deprivation therapy, ADT) or by direct AR inhibition (i.e. enzalutamide, Enz), resulting in the depletion of androgen regulated essential survival genes in PCa cells, and initial beneficial clinical response. However, most patients eventually develop resistance, and present with either AR+ or AR- CRPC. Right Panel: Using shTMEFF2-3 as an example, AN-DISE, directly reduces the expression of non-androgen regulated essential survival genes, as well as, androgen signaling regulatory genes, such as, AR, TAF1 and USP12, through shRNA seed complementarity to the 3'UTR. Resultant inhibition of androgen signaling leads to the reduction of androgen regulated essential survival genes, and increased PCa cell death. The global nature of the DISE mechanism, and the sensitivity of both AR+ and AR- CRPC cells, indicate resistance may be less probable compared to standard androgen signaling targeted therapies.

Herein it is demonstrated that shRNAs targeting TMEFF2 inhibited androgen signaling in AR+ PCa cell lines (both ADPC and CRPC) and elicited toxicity in transformed cells. RNA seq analysis with representative TMEFF2-targeted shRNAs suggests these phenotypes are induced by reduced essential gene expression via off target shRNA seed/3' UTR interactions, resembling a previously described process, Death Induced by Survival gene Elimination (DISE). Unique to this work, we showed that the 3' UTR of AR and AR coregulatory genes are also targets of TMEFF2 targeted shRNA seed interactions, leading to androgen signaling inhibition and further essential gene downregulation. Consequently, the inhibition of androgen signaling by DISE-inducing shRNAs correlated with toxicity in LNCaP cells compared to cells that do not depend on AR activity for growth and survival. We term this DISE-subtype, in which essential genes are eliminated in AR+PCa cells through direct off-target seed interactions and the depletion of the AR and androgen signaling coregulatory genes, androgen network DISE (AN-DISE) (FIG. 6). Unlike androgen deprivation therapy or other AR targeted therapies, AN-DISE, in addition to inhibiting androgen signaling, directly downregulates numerous non-androgen regulated essential genes, making developed resistance less likely. In support of this concept, DU145, an AR negative CPRC cell line, like other transformed cells, are also sensitive to DISE-inducing shRNAs. In addition to AN-DISE in PCa cells, other cancer cell types that are largely dependent on a single pathway for the expression of essential survival genes, such as estrogen receptor positive breast cancer, may also show increased sensitivity to the DISE mechanism if the central survival pathway is also compromised. Previous reports and our viability experiments with normal prostate epithelial cell line, RWPE1, suggest that DISE preferentially occurs in transformed cells, further supporting therapeutic potential. Importantly, DISE-inducing siRNAs have already been shown to be effective in reducing tumor growth in vivo using an ovarian cancer mouse model, with little to no evident systemic toxicity.

Herein, also identified were at least three miRNAs, miR-4446-5p, miR-634 and miR6888-3p, that have identical seed sequence and many common predicted targets to three of the TMEFF2 shRNAs described herein These data indicate that miR-4446-5p, miR-634, and miR6888-3p, have an effect on tumor suppressive miRNAs, especially in PCa.

In summary, in addition to corroborating previous studies describing DISE induction through shRNA seed-mediated off target effects, data from this work indicate that DISE-inducing shRNAs that inhibit AR transcriptional activity through the depletion of androgen signaling regulatory genes are particularly toxic to AR positive PCa cells via subsequent elimination of additional survival genes, demonstrating therapeutic use of these RNAi seeds in treatment of PCa.

Thus, in accordance with the present disclosure, there have been provided compositions, as well as methods of producing and using same, which fully satisfy the objectives and advantages set forth hereinabove. Although the present disclosure has been described in conjunction with specific formulas, compositions, and methods set forth hereinabove, it is evident that many alternatives, modifications, and variations will be apparent to those skilled in the art. Accordingly, it is intended to embrace all such alternatives, modifications, and variations that fall within the spirit and broad scope of the present disclosure.

In at least certain embodiments, the present disclosure is directed to the following non-limiting clauses.

Clause 1. A nucleic acid compound, comprising an oligonucleotide selected from the group consisting of short interfering RNA (siRNA), short hairpin RNA (shRNA), antisense RNA, antisense DNA, Chimeric Antisense DNA/RNA, and microRNA (miRNA), wherein the oligonucleotide has a 6-mer seed sequence that is complementary to a sequence of either a gene or an mRNA encoding an androgen receptor (AR) coregulator or a fragment thereof having AR coregulator activity; wherein the oligonucleotide comprises a nucleic acid sequence selected from the group consisting of SEQ ID NO:36, SEQ ID NO:31, SEQ ID NO:35, SEQ ID NO:60, SEQ ID NO:51, SEQ ID NO:54, SEQ ID NO:44, SEQ ID NO:38, SEQ ID NO:37, SEQ ID NO:52, SEQ ID NO:50, SEQ ID NO:43, SEQ ID NO:49, SEQ ID NO:42, SEQ ID NO:40, SEQ ID NO:47, SEQ ID NO:39, SEQ ID NO:55, SEQ ID NO:56, SEQ ID NOS:28-30, SEQ ID NOS:32-34, SEQ ID NO:41, SEQ ID NO:45, SEQ ID NO:46, SEQ ID NO:48, SEQ ID NO:53, SEQ ID NOS:57-59, SEQ ID NOS:61-63, and nucleic acid sequences complementary to each of said sequences; and wherein the nucleic acid compound comprises at least one of (1) a non-natural modification in the oligonucleotide, and (2) an organic moiety conjugated to the oligonucleotide; and wherein the nucleic acid compound has inhibitory activity against the expression or biological activity of the AR coregulator or biologically active fragment thereof.

Clause 2. The nucleic acid compound of clause 1, wherein the oligonucleotide has a strand length in a range of 12 to 50 nucleotides.

Clause 3. The nucleic acid compound of clause 1 or 2, wherein the at least one non-natural modification in the oligonucleotide is selected from the group consisting of a modified nucleoside sugar, a modified internucleoside linkage, and a modified nucleobase.

Clause 4. The nucleic acid compound of clause 3, wherein the modified nucleoside sugar comprises a 2'-modified sugar.

Clause 5. The nucleic acid compound of clause 4, wherein the 2'-modified sugar is selected from the group consisting of 2'-O-methyl-, 2'-deoxy-, 2'-deoxy-2'-fluoro-, 2'-O-methoxyethyl-(2'-O-MOE)-, 2'-O-aminopropyl-(2'-O-AP)-, 2'-O-dimethylaminoethyl-(2'-O-DMAOE)-, 2'-O-dimethylaminopropyl-(2'-O-DMAP)-, 2'-O-dimethylaminoethyloxyethyl-(2'-O-DMAEOE)-, and 2'-O—N-methylacetamido-(2'-O-NMA)-modified sugars.

Clause 6. The nucleic acid compound of any one of clauses 3-5, wherein the modified internucleoside linkage is selected from the group consisting of phosphorothioate, phosphorodithioate, phosphoramidite, phosphorodiamidate, morpholino, phosphotriester, aminoalkylphosphotriester, phosphonate, alkyl phosphonate, 3'-alkylene phosphonate, 5'-alkylene phosphonate, chiral phosphonate, and phosphinate linkages.

Clause 7. The nucleic acid compound of any one of clauses 3-6, wherein the modified internucleoside linkage comprises at least the first, second, or third internucleoside linkage at the 5' and/or 3' end of the oligonucleotide.

Clause 8. The nucleic acid compound of any one of clauses 3-7, wherein the modified nucleobase is selected from the group consisting of 5-uracil (pseudouridine), dihydrouracil, inosine, ribothymine, 5-me-C, 7-methylguanine, hypoxanthine, xanthine, 5-hydroxymethyl cytosine, 2-aminoadenine, 2-methyladenine, 6-methyladenine, 2-propyladenine, N6-adenine, N6-isopentenyladenine, 2-methylthio-N6-isopentenyladenine, 2-methylguanine, 6-methylguanine, 2-propylguanine, 1-methylguanine, 7-methylguanine, 2,2-dimethylguanine, 2-thiouracil, 2-thiothymine, 2-thiocytosine, 5-fluorouracil, 5-bromouracil, 5-chlorouracil, 5-iodouracil, dihydrouracil, 5-methyl-2-thiouracil, 2-thiouracil, 4-thiouracil, 5-methyluracil, uracil-5-oxyacetic acid methylester, uracil-5-oxyacetic acid, 5-carboxymethylaminomethyl-2-thiouracil, hypoxanthine, xanthine, 4-acetylcytosine, 5-(carboxyhydroxylmethyl) uracil, 5-methoxycarboxymethyluracil, 5-methoxyuracil, 5-methyl-2-thiouracil, 3-(3-amino-3-N-2-carboxypropyl) uracil, 5-carboxymethylaminomethyluracil, 5-methylaminomethyluracil, 5-methoxyaminomethyl-2-thiouracil, alkynyl derivatives of pyrimidine bases including 5-propynyl uracil, and 5-propynyl cytosine, 6-azo uracil, 6-azo cytosine, 6-azo thymine, 4-thiouracil, 8-halo-adenines, 8-amino adenine, 8-thiol adenine, 8-thioalkyl adenine, 8-hydroxyl adenine, 5-trifluoromethyl uracil, 3-methylcytosine, 5-methylcytosine, 5-trifluoromethyl cytosine, 7-methylguanine,7-methyladenine, 2-F-adenine, 2-amino-adenine, 8-azaguanine and 8-azaadenine, 7-deazaguanine, 8-halo-guanines, 8-amino guanine, 8-thiol guanine, 8-thioalkyl guanine, 8-hydroxyl guanine, 7-deazaadenine, 3-deazaguanine, 3-deazaadenine, beta-D-galactosylqueosine, beta-D-mannosylqueosine, 1-methylinosine, 2,6-diaminopurine, queosine, tricyclic pyrimidines, phenoxazine cytidine (1H-pyrimido [5,4-b][1,4]benzoxazin-2(3H)-one), and phenothiazine cytidine (1H-pyrimido[5,4-b][1,4]benzothiazin-2(3H)-one.

Clause 9. The nucleic acid compound of any one of clauses 3-8, wherein the organic moiety is selected from the group consisting of lipids, peptides, receptor-specific ligands, aptamers, antibodies or antibody fragments, CpG-containing oligonucleotides, polyamines, polymers, dendrimers, saccharides, polysaccharides, and cyclodextrins.

Clause 10. The nucleic acid compound of any one of clauses 3-9, wherein the AR coregulator is selected from the group consisting of ADAM10, APPBP2, ATAD2, BAG1, BRCA1, CALM1, CALR, CCND1, CCND3, CDC25A, CDK2AP1, CTNNB1, CDK7, CTDSP2, COPS5, CTDSP2, ENY2, EHMT2, FKBP4, FKBP5, GSK3B, HELZ2, HEY1, HIP1, HIPK3, IDE, IL6ST, KAT2B, MAPK1, MAPK15, MED1, MED21, MKRN1, NCOA2, PER1, PIAS1, PIK3CB, PIK3R1, PMEPA1, PRMT2, PSMC3IP, PQBP1, PRKDC, RANBP9, RANBP10, RPS6KA1, RPS6KA3, SMAD1, SMARCD1, TAF1, TPD52, UBE2L3, UXT, YWHAH, and ZMIZ1.

Clause 11. The nucleic acid compound of any one of clauses 3-10, wherein the AR coregulator is an AR coregulator of an aggressive prostate cancer.

Clause 12. An expression vector comprising the oligonucleotide of any one of clauses 3-11.

Clause 13. A composition, comprising at least one nucleic acid compound of any one of clauses 3-12, and a pharmaceutically-acceptable carrier.

Clause 14. The composition of clause 13, comprising a nanoparticle.

Clause 15. A method for treating prostate cancer in a subject in need of such treatment, comprising: administering to the subject a therapeutically effective amount of an oligonucleotide selected from the group consisting of short interfering RNA (siRNA), short hairpin RNA (shRNA), antisense RNA, antisense DNA, Chimeric Antisense DNA/RNA, and microRNA (miRNA), wherein the oligonucleotide has a 6-mer seed sequence that is complementary to a sequence of either a gene or an mRNA encoding an androgen receptor (AR) coregulator or a fragment thereof having AR coregulator activity; wherein the oligonucleotide comprises a nucleic acid sequence selected from the group consisting of SEQ ID NO:36, SEQ ID NO:31, SEQ ID NO:35, SEQ ID NO:60, SEQ ID NO:51, SEQ ID NO:54, SEQ ID NO:44, SEQ ID NO:38, SEQ ID NO:37, SEQ ID NO:52, SEQ ID NO:50, SEQ ID NO:43, SEQ ID NO:49, SEQ ID NO:42, SEQ ID NO:40, SEQ ID NO:47, SEQ ID NO:39, SEQ ID NO:55, SEQ ID NO:56, SEQ ID NOS:28-30, SEQ ID NOS:32-34, SEQ ID NO:41, SEQ ID NO:45, SEQ ID NO:46, SEQ ID NO:48, SEQ ID NO:53, SEQ ID NOS:57-59, SEQ ID NOS:61-63, and nucleic acid sequences complementary to each of said sequences; and wherein the oligonucleotide has inhibitory activity against the expression or biological activity of the AR coregulator or biologically active fragment thereof.

Clause 16. The method of clause 15, wherein the prostate cancer is aggressive prostate cancer.

Clause 17. The method of clause 15 or 16, wherein the oligonucleotide comprises a portion of a nucleic acid compound or nucleic acid composition.

Clause 18. The method of any one of clauses 15-17, wherein the oligonucleotide comprises at least one of (1) a non-natural modification in the oligonucleotide, and (2) an organic moiety conjugated to the oligonucleotide.

Clause 19. The method of clause 18, wherein the at least one non-natural modification in the oligonucleotide is selected from the group consisting of a modified nucleoside sugar, a modified internucleoside linkage, and a modified nucleobase.

Clause 20. The method of clause 19, wherein the modified nucleoside sugar comprises a 2'-modified sugar.

Clause 21. The method of clause 20, wherein the 2'-modified sugar is selected from the group consisting of 2'-O-methyl-, 2'-deoxy-, 2'-deoxy-2'-fluoro-, 2'-O-methoxyethyl-(2'-O-MOE)-, 2'-O-aminopropyl-(2'-O-AP)-, 2'-O-dimethylaminoethyl-(2'-O-DMAOE)-, 2'-O-dimethylaminopropyl-(2'-O-DMAP)-, 2'-O-dimethylaminoethyloxyethyl-(2'-O-DMAEOE)-, and 2'-O—N-methylacetamido-(2'-O-NMA)-modified sugars.

Clause 22. The method of any one of clauses 19-21, wherein the modified internucleoside linkage is selected from the group consisting of phosphorothioate, phosphorodithioate, phosphoramidite, phosphorodiamidate, morpholino, phosphotriester, aminoalkylphosphotriester, phosphonate, alkyl phosphonate, 3'-alkylene phosphonate, 5'-alkylene phosphonate, chiral phosphonate, and phosphinate linkages.

Clause 23. The method of any one of clauses 19-22, wherein the modified internucleoside linkage comprises at least the first, second, or third internucleoside linkage at the 5' and/or 3' end of the oligonucleotide.

Clause 24. The method of any one of clauses 19-23, wherein the modified nucleobase is selected from the group consisting of 5-uracil (pseudouridine), dihydrouracil, inosine, ribothymine, 5-me-C, 7-methylguanine, hypoxanthine, xanthine, 5-hydroxymethyl cytosine, 2-aminoadenine, 2-methyladenine, 6-methyladenine, 2-propyladenine, N6-adenine, N6-isopentenyladenine, 2-methylthio-N6-isopentenyladenine, 2-methylguanine, 6-methylguanine, 2-propylguanine, 1-methylguanine, 7-methylguanine, 2,2-dimethylguanine, 2-thiouracil, 2-thiothymine, 2-thiocytosine, 5-fluorouracil, 5-bromouracil, 5-chlorouracil, 5-iodouracil, dihydrouracil, 5-methyl-2-thiouracil, 2-thiouracil, 4-thiouracil, 5-methyluracil, uracil-5-oxyacetic acid methylester, uracil-5-oxyacetic acid, 5-carboxymethylaminomethyl-2-thiouracil, hypoxanthine, xanthine, 4-acetylcytosine, 5-(carboxyhydroxylmethyl) uracil, 5-methoxycarboxymethyluracil, 5-methoxyuracil, 5-methyl-2-thiouracil, 3-(3-amino-3-N-2-carboxypropyl) uracil, 5-carboxymethylaminomethyluracil, 5-methylaminomethyluracil, 5-methoxyaminomethyl-2-thiouracil, alkynyl derivatives of pyrimidine bases including 5-propynyl uracil, and 5-propynyl cytosine, 6-azo uracil, 6-azo cytosine, 6-azo thymine, 4-thiouracil, 8-haloadenines, 8-amino adenine, 8-thiol adenine, 8-thioalkyl adenine, 8-hydroxyl adenine, 5-trifluoromethyl uracil, 3-methylcytosine, 5-methylcytosine, 5-trifluoromethyl cytosine, 7-methylguanine, 7-methyladenine, 2-F-adenine, 2-amino-adenine, 8-azaguanine and 8-azaadenine, 7-deazaguanine, 8-halo-guanines, 8-amino guanine, 8-thiol guanine, 8-thioalkyl guanine, 8-hydroxyl guanine, 7-deazaadenine, 3-deazaguanine, 3-deazaadenine, beta-D-galactosylqueosine, beta-D-mannosylqueosine, 1-methylinosine, 2,6-diaminopurine, queosine, tricyclic pyrimidines, phenoxazine cytidine(1H-pyrimido[5,4-b][1,4] benzoxazin-2(3H)-one), and phenothiazine cytidine (1H-pyrimido[5,4-b][1,4]benzothiazin-2(3H)-one.

Clause 25. The method of any one of clauses 18-24, wherein the organic moiety is selected from the group consisting of lipids, peptides, receptor-specific ligands, aptamers, antibodies or antibody fragments, CpG-containing oligonucleotides, polyamines, polymers, dendrimers, saccharides, polysaccharides, and cyclodextrins.

Clause 26. The method of any one of clauses 19-25, wherein the AR coregulator is selected from the group consisting of ADAM10, APPBP2, ATAD2, BAG1, BRCA1, CALM1, CALR, CCND1, CCND3, CDC25A, CDK2AP1, CTNNB1, CDK7, CTDSP2, COPS5, CTDSP2, ENY2, EHMT2, FKBP4, FKBP5, GSK3B, HELZ2, HEY1, HIP1, HIPK3, IDE, IL6ST, KAT2B, MAPK1, MAPK15, MED1, MED21, MKRN1, NCOA2, PER1, PIAS1, PIK3CB, PIK3R1, PMEPA1, PRMT2, PSMC3IP, PQBP1, PRKDC, RANBP9, RANBP10, RPS6KA1, RPS6KA3, SMAD1, SMARCD1, TAF1, TPD52, UBE2L3, UXT, YWHAH, and ZMIZ1.

Clause 27. The method of any one of clauses 19-26, wherein the AR coregulator is an AR coregulator of an aggressive prostate cancer.

What is claimed is:

1. A nucleic acid compound, comprising
an oligonucleotide selected from the group consisting of short interfering RNA (siRNA), short hairpin RNA (shRNA), antisense RNA, antisense DNA, Chimeric Antisense DNA/RNA, and microRNA (miRNA), wherein the oligonucleotide comprises the nucleic acid sequence SEQ ID NO:60, and nucleic acid sequences complementary to said sequence; and
wherein the nucleic acid compound comprises at least one of (1) a non-natural modification in the oligonucleotide, and (2) an organic moiety conjugated to the oligonucleotide, with the proviso that $X_2$, $X_3$, and $X_4$ of SEQ ID NO:60 are selected from uracil and a modified uracil nucleobase, with the proviso that the modified uracil nucleobase is not a thymine; and wherein the nucleic acid compound has inhibitory activity against the expression or biological activity of an androgen receptor (AR) coregulator or biologically active fragment thereof.

2. The nucleic acid compound of claim 1, wherein the oligonucleotide has a strand length in a range of 12 to 50 nucleotides.

3. The nucleic acid compound of claim 1, wherein the at least one non-natural modification in the oligonucleotide is selected from the group consisting of a modified nucleoside sugar, a modified internucleoside linkage, and a modified nucleobase.

4. The nucleic acid compound of claim 3, wherein the modified nucleoside sugar comprises a 2'-modified sugar.

5. The nucleic acid compound of claim 4, wherein the 2'-modified sugar is selected from the group consisting of 2'-O-methyl-, 2'-deoxy-, 2'-deoxy-2'-fluoro-, 2'-O-methoxyethyl-(2'-O-MOE)-, 2'-O-aminopropyl-(2'-O-AP)-, 2'-O-dimethylaminoethyl-(2'-O-DMAOE)-, 2'-O-dimethylaminopropyl-(2'-O-DMAP)-, 2'-O-dimethylaminoethyloxyethyl-(2'-O-DMAEOE)-, and 2'-O—N-methylacetamido-(2'-O-NMA)-modified sugars.

6. The nucleic acid compound of claim 3, wherein the modified internucleoside linkage is selected from the group consisting of phosphorothioate, phosphorodithioate, phosphoramidite, phosphorodiamidate, morpholino, phosphotriester, aminoalkylphosphotriester, phosphonate, alkyl phosphonate, 3'-alkylene phosphonate, 5'-alkylene phosphonate, chiral phosphonate, and phosphinate linkages.

7. The nucleic acid compound of claim 3, wherein the modified internucleoside linkage comprises at least the first, second, or third internucleoside linkage at the 5' and/or 3' end of the oligonucleotide.

8. The nucleic acid compound of claim 3, wherein the modified nucleobase is selected from the group consisting of 5-uracil (pseudouridine), inosine, ribothymine, 7-methylguanine, hypoxanthine, xanthine, 5-hydroxymethyl cytosine, 2-aminoadenine, 2-methyladenine, 6-methyladenine, 2-propyladenine, N6-adenine, N6-isopentenyladenine, 2-methylthio-N6-isopentenyladenine, 2-methylguanine, 6-methylguanine, 2-propylguanine, 1-methylguanine, 7-methylguanine, 2,2-dimethylguanine, 2-thiouracil, 2-thiothymine, 2-thiocytosine, 5-fluorouracil, 5-bromouracil, 5-chlorouracil, 5-iodouracil, dihydrouracil, 5-methyl-2-thiouracil, 4-thiouracil, 5-methyluracil, uracil-5-oxyacetic acid methylester, uracil-5-oxyacetic acid, 5-carboxymethylaminomethyl-2-thiouracil, 4-acetylcytosine, 5-(carboxyhydroxylmethyl) uracil, 5-methoxycarboxymethyluracil, 5-methoxyuracil, 5-methyl-2-thiouracil, 3-(3-amino-3-N-2-carboxypropyl) uracil, 5-carboxymethylaminomethyluracil, 5-methylaminomethyluracil, 5-methoxyaminomethyl-2-thiouracil, alkynyl derivatives of pyrimidine bases including 5-propynyl uracil, and 5-propynyl cytosine, 6-azo uracil, 6-azo cytosine, 6-azo thymine, 8-halo-adenines, 8-amino adenine, 8-thiol adenine, 8-thioalkyl adenine, 8-hydroxyl adenine, 5-trifluoromethyl uracil, 3-methylcytosine, 5-methylcytosine, 5-trifluoromethyl cytosine, 7-methyladenine, 2-F-adenine, 8-azaguanine and 8-azaadenine, 7-deazaguanine, 8-halo-guanines, 8-amino guanine, 8-thiol guanine, 8-thioalkyl guanine, 8-hydroxyl guanine, 7-deazaadenine, 3-deazaguanine, 3-deazaadenine, beta-D-galactosylqueosine, beta-D-mannosylqueosine, 1-methylinosine, 2,6-diaminopurine, queosine, tricyclic pyrimidines, phenoxazine cytidine (1H-pyrimido[5,4-b][1,4]benzoxazin-2(3H)-one), and phenothiazine cytidine (1H-pyrimido [5,4-b][1,4]benzothiazin-2(3H)-one.

9. The nucleic acid compound of claim 1, wherein the organic moiety is selected from the group consisting of lipids, peptides, receptor-specific ligands, aptamers, antibodies or antibody fragments, CpG-containing oligonucleotides, polyamines, polymers, dendrimers, saccharides, polysaccharides, and cyclodextrins.

10. The nucleic acid compound of claim 1, wherein the AR coregulator is CCND1.

11. The nucleic acid compound of claim 1, wherein the AR coregulator is an AR coregulator of an aggressive prostate cancer.

12. A composition, comprising at least one nucleic acid compound of claim 1, and a pharmaceutically-acceptable carrier.

13. The composition of claim 12, comprising a nanoparticle.

14. A nucleic acid compound, comprising
an oligonucleotide selected from the group consisting of short interfering RNA (siRNA), short hairpin RNA (shRNA), antisense RNA, antisense DNA, Chimeric Antisense DNA/RNA, and microRNA (miRNA), wherein the oligonucleotide;
comprises the nucleic acid sequence SEQ ID NO:60, and nucleic acid sequences complementary to said sequence; and wherein the nucleic acid compound comprises at least one of (1) a non-natural modification in the oligonucleotide, and (2) an organic moiety conjugated to the oligonucleotide, with the proviso that $X_2$, $X_3$, and $X_4$ of SEQ ID NO:60 are selected from uracil and modified uracil nucleobases, wherein the modified uracil nucleobases are selected from the group consisting of dihydrouracil, 2-thiouracil, 4-thiouracil, 5-fluorouracil, 5-bromouracil, 5-chlorouracil, 5-iodouracil, 5-methyluracil, 5-trifluoromethyl uracil, 5-methoxyuracil, 5-methyl-2-thiouracil, uracil-5-oxyacetic acid methylester, uracil-5-oxy acetic acid, 5-carboxymethylaminomethyl-2-thiouracil, 5-(carboxyhydroxylmethyl) uracil, 5-methoxycarboxymethyluracil, 5-methyl-2-thiouracil, 3-(3-amino-3-N-2-carboxypropyl) uracil, 5-carboxymethylaminomethyluracil, 5-methylaminomethyluracil, 5-methoxyaminomethyl-2-thiouracil, alkynyl derivatives of uracil, 5-propynyl uracil, and 6-azo uracil; and
wherein the nucleic acid compound has inhibitory activity against the expression or biological activity of an androgen receptor (AR) coregulator or biologically active fragment thereof.

15. The nucleic acid compound of claim 14, wherein the oligonucleotide has a strand length in a range of 12 to 50 nucleotides.

16. The nucleic acid compound of claim 14, wherein the at least one non-natural modification in the oligonucleotide is selected from the group consisting of a modified nucleoside sugar, a modified internucleoside linkage, and a modified nucleobase.

17. The nucleic acid compound of claim 16, wherein the modified nucleoside sugar comprises a 2'-modified sugar.

18. The nucleic acid compound of claim 17, wherein the 2'-modified sugar is selected from the group consisting of 2'-O-methyl-, 2'-deoxy-, 2'-deoxy-2'-fluoro-, 2'-O-methoxyethyl-(2'-O-MOE)-, 2'-O-aminopropyl-(2'-O-AP)-, 2'-O-dimethylaminoethyl-(2'-O-DMAOE)-, 2'-O-dimethylaminopropyl-(2'-O-DMAP)-, 2'-O-dimethylaminoethyloxyethyl-(2'-O-DMAEOE)-, and 2'-O—N-methylacetamido-(2'-O-NMA)-modified sugars.

19. The nucleic acid compound of claim 16, wherein the modified internucleoside linkage comprises at least the first, second, or third internucleoside linkage at the 5' and/or 3' end of the oligonucleotide.

20. The nucleic acid compound of claim 16, wherein the modified nucleobase is selected from the group consisting of 5-uracil (pseudouridine), inosine, ribothymine, 7-methylguanine, hypoxanthine, xanthine, 5-hydroxymethyl cytosine, 2-aminoadenine, 2-methyladenine, 6-methyladenine, 2-propyladenine, N6-adenine, N6-isopentenyladenine, 2-methylthio-N6-isopentenyladenine, 2-methylguanine, 6-methylguanine, 2-propylguanine, 1-methylguanine, 7-methylguanine, 2,2-dimethylguanine, 2-thiouracil, 4-thiouracil, 2-thiothymine, 2-thiocytosine, 5-fluorouracil, 5-bromouracil, 5-chlorouracil, 5-iodouracil, dihydrouracil, 5-methyl-2-thiouracil, 5-methyluracil, uracil-5-oxyacetic acid methylester, uracil-5-oxyacetic acid, 5-carboxymethylaminomethyl-2-thiouracil, 4-acetylcytosine, 5-(carboxyhydroxylmethyl) uracil, 5-methoxycarboxymethyluracil, 5-methoxyuracil, 5-methyl-2-thiouracil, 3-(3-amino-3-N-2-carboxypropyl) uracil, 5-carboxymethylaminomethyluracil, 5-methylaminomethyluracil, 5-methoxyaminomethyl-2-thiouracil, alkynyl derivatives of pyrimidine bases including 5-propynyl uracil, and 5-propynyl cytosine, 6-azo uracil, 6-azo cytosine, 6-azo thymine, 8-halo-adenines, 8-amino adenine, 8-thiol adenine, 8-thioalkyl adenine, 8-hydroxyl adenine, 5-trifluoromethyl uracil, 3-methylcytosine, 5-methylcytosine, 5-trifluoromethyl cytosine, 7-methyladenine, 2-F-adenine, 8-azaguanine and 8-azaadenine, 7-deazaguanine, 8-halo-guanines, 8-amino guanine, 8-thiol guanine, 8-thioalkyl guanine, 8-hydroxyl guanine, 7-deazaadenine, 3-deazaguanine, 3-deazaadenine, beta-D-galactosylqueosine, beta-D-mannosylqueosine, 1-methylinosine, 2,6-diaminopurine, queosine, tricyclic pyrimidines, phenoxazine cytidine(1H-pyrimido[5,4-b][1,4]benzoxazin-2(3H)-one), and phenothiazine cytidine (1H-pyrimido [5,4-b][1,4]benzothiazin-2(3H)-one.

21. The nucleic acid compound of claim 14, wherein the organic moiety is selected from the group consisting of lipids, peptides, receptor-specific ligands, aptamers, antibodies or antibody fragments, CpG-containing oligonucleotides, polyamines, polymers, dendrimers, saccharides, polysaccharides, and cyclodextrins.

22. The nucleic acid compound of claim 14, wherein the AR coregulator is CCND1.

23. The nucleic acid compound of claim 14, wherein the AR coregulator is an AR coregulator of an aggressive prostate cancer.

24. A composition, comprising at least one nucleic acid compound of claim 14, and a pharmaceutically-acceptable carrier.

25. The composition of claim 24, comprising a nanoparticle.

26. The nucleic acid compound of claim 16, wherein the modified internucleoside linkage is selected from the group consisting of phosphorothioate, phosphorodithioate, phosphoramidite, phosphorodiamidate, morpholino, phosphotriester, aminoalkylphosphotriester, phosphonate, alkyl phosphonate, 3'-alkylene phosphonate, 5'-alkylene phosphonate, chiral phosphonate, and phosphinate linkages.

* * * * *

```
                          SEQUENCE LISTING

<160> NUMBER OF SEQ ID NOS: 134

<210> SEQ ID NO 1
<211> LENGTH: 21
<212> TYPE: DNA
<213> ORGANISM: Artificial Sequence
<220> FEATURE:
<223> OTHER INFORMATION: Completely synthesized in the lab.

<400> SEQUENCE: 1
ctggttatga tgacagagaa a                                              21

<210> SEQ ID NO 2
<211> LENGTH: 21
<212> TYPE: DNA
<213> ORGANISM: Artificial Sequence
<220> FEATURE:
<223> OTHER INFORMATION: Completely synthesized in the lab.

<400> SEQUENCE: 2
cgtctgtcag ttcaagtgca a                                              21

<210> SEQ ID NO 3
<211> LENGTH: 21
<212> TYPE: DNA
<213> ORGANISM: Artificial Sequence
<220> FEATURE:
<223> OTHER INFORMATION: Completely synthesized in the lab.

<400> SEQUENCE: 3
gcgcttctga tgggaaatct t                                              21

<210> SEQ ID NO 4
<211> LENGTH: 21
<212> TYPE: DNA
<213> ORGANISM: Artificial Sequence
<220> FEATURE:
<223> OTHER INFORMATION: Completely synthesized in the lab.

<400> SEQUENCE: 4
gcaggtgtga tgctggttat a                                              21

<210> SEQ ID NO 5
<211> LENGTH: 21
<212> TYPE: DNA
<213> ORGANISM: Artificial Sequence
<220> FEATURE:
<223> OTHER INFORMATION: Completely synthesized in the lab.

<400> SEQUENCE: 5
ccttgcattt gtggtaatct a                                              21

<210> SEQ ID NO 6
<211> LENGTH: 21
<212> TYPE: DNA
<213> ORGANISM: Artificial Sequence
<220> FEATURE:
<223> OTHER INFORMATION: Completely synthesized in the lab.

<400> SEQUENCE: 6
ggctctggag aaactagtca a                                              21
```

<210> SEQ ID NO 7
<211> LENGTH: 21
<212> TYPE: DNA
<213> ORGANISM: Artificial Sequence
<220> FEATURE:
<223> OTHER INFORMATION: Completely synthesized in the lab.

<400> SEQUENCE: 7
atgcagagaa tgctaacaaa t                                              21

<210> SEQ ID NO 8
<211> LENGTH: 21
<212> TYPE: DNA
<213> ORGANISM: Artificial Sequence
<220> FEATURE:
<223> OTHER INFORMATION: Completely synthesized in the lab.

<400> SEQUENCE: 8
cataccttgt ccggaacatt a                                              21

<210> SEQ ID NO 9
<211> LENGTH: 21
<212> TYPE: DNA
<213> ORGANISM: Artificial Sequence
<220> FEATURE:
<223> OTHER INFORMATION: Completely synthesized in the lab.

<400> SEQUENCE: 9
ggcactacag ttcagacaat a                                              21

<210> SEQ ID NO 10
<211> LENGTH: 21
<212> TYPE: DNA
<213> ORGANISM: Artificial Sequence
<220> FEATURE:
<223> OTHER INFORMATION: Completely synthesized in the lab.

<400> SEQUENCE: 10
cctaaggtta agtcgccctc g                                              21

<210> SEQ ID NO 11
<211> LENGTH: 21
<212> TYPE: DNA
<213> ORGANISM: Artificial Sequence
<220> FEATURE:
<223> OTHER INFORMATION: Completely synthesized in the lab.

<400> SEQUENCE: 11
cgacgtaaac ggccacaagt t                                              21

<210> SEQ ID NO 12
<211> LENGTH: 21
<212> TYPE: DNA
<213> ORGANISM: Artificial Sequence
<220> FEATURE:
<223> OTHER INFORMATION: Completely synthesized in the lab.

<400> SEQUENCE: 12
actgggctgt actttgtata t                                              21

<210> SEQ ID NO 13
<211> LENGTH: 21
<212> TYPE: DNA
<213> ORGANISM: Artificial Sequence
<220> FEATURE:
<223> OTHER INFORMATION: Completely synthesized in the lab.

```
<400> SEQUENCE: 13
cctgaaacag tggcaataaa t                                              21

<210> SEQ ID NO 14
<211> LENGTH: 20
<212> TYPE: DNA
<213> ORGANISM: Artificial Sequence
<220> FEATURE:
<223> OTHER INFORMATION: Completely synthesized in the lab.

<400> SEQUENCE: 14
aagatcgagt gccgcatcac                                                20

<210> SEQ ID NO 15
<211> LENGTH: 20
<212> TYPE: DNA
<213> ORGANISM: Artificial Sequence
<220> FEATURE:
<223> OTHER INFORMATION: Completely synthesized in the lab.

<400> SEQUENCE: 15
ccagctgctg cactgccgcg                                                20

<210> SEQ ID NO 16
<211> LENGTH: 19
<212> TYPE: RNA
<213> ORGANISM: Artificial Sequence
<220> FEATURE:
<223> OTHER INFORMATION: Completely synthesized in the lab.

<400> SEQUENCE: 16
cucugucauc auaaccaga                                                 19

<210> SEQ ID NO 17
<211> LENGTH: 19
<212> TYPE: RNA
<213> ORGANISM: Artificial Sequence
<220> FEATURE:
<223> OTHER INFORMATION: Completely synthesized in the lab.

<400> SEQUENCE: 17
cacuugaacu gacagacgc                                                 19

<210> SEQ ID NO 18
<211> LENGTH: 19
<212> TYPE: RNA
<213> ORGANISM: Artificial Sequence
<220> FEATURE:
<223> OTHER INFORMATION: Completely synthesized in the lab.

<400> SEQUENCE: 18
auuucccauc agaagcgca                                                 19

<210> SEQ ID NO 19
<211> LENGTH: 19
<212> TYPE: RNA
<213> ORGANISM: Artificial Sequence
<220> FEATURE:
<223> OTHER INFORMATION: Completely synthesized in the lab.

<400> SEQUENCE: 19
aaccagcauc acaccugca                                                 19

<210> SEQ ID NO 20
```

```
<211> LENGTH: 19
<212> TYPE: RNA
<213> ORGANISM: Artificial Sequence
<220> FEATURE:
<223> OTHER INFORMATION: Completely synthesized in the lab.

<400> SEQUENCE: 20
auuaccacaa augcaaggc                                              19

<210> SEQ ID NO 21
<211> LENGTH: 19
<212> TYPE: RNA
<213> ORGANISM: Artificial Sequence
<220> FEATURE:
<223> OTHER INFORMATION: Completely synthesized in the lab.

<400> SEQUENCE: 21
acuaguuucu ccagagccu                                              19

<210> SEQ ID NO 22
<211> LENGTH: 19
<212> TYPE: RNA
<213> ORGANISM: Artificial Sequence
<220> FEATURE:
<223> OTHER INFORMATION: Completely synthesized in the lab.

<400> SEQUENCE: 22
uguuagcauu cucugcaua                                              19

<210> SEQ ID NO 23
<211> LENGTH: 19
<212> TYPE: RNA
<213> ORGANISM: Artificial Sequence
<220> FEATURE:
<223> OTHER INFORMATION: Completely synthesized in the lab.

<400> SEQUENCE: 23
uguuccggac aagguaugu                                              19

<210> SEQ ID NO 24
<211> LENGTH: 19
<212> TYPE: RNA
<213> ORGANISM: Artificial Sequence
<220> FEATURE:
<223> OTHER INFORMATION: Completely synthesized in the lab.

<400> SEQUENCE: 24
ugucugaacu guagugccc                                              19

<210> SEQ ID NO 25
<211> LENGTH: 22
<212> TYPE: RNA
<213> ORGANISM: Artificial Sequence
<220> FEATURE:
<223> OTHER INFORMATION: Completely synthesized in the lab.

<400> SEQUENCE: 25
aaccagcacc ccaacuuugg ac                                          22

<210> SEQ ID NO 26
<211> LENGTH: 22
<212> TYPE: RNA
<213> ORGANISM: Artificial Sequence
<220> FEATURE:
<223> OTHER INFORMATION: Completely synthesized in the lab.

<400> SEQUENCE: 26
```

-continued auuucccugc cauucccuug gc                                          22

<210> SEQ ID NO 27
<211> LENGTH: 21
<212> TYPE: RNA
<213> ORGANISM: Artificial Sequence
<220> FEATURE:
<223> OTHER INFORMATION: Completely synthesized in the lab.

<400> SEQUENCE: 27
aucugucucg auuguuucca g                                           21

<210> SEQ ID NO 28
<211> LENGTH: 10
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(2)
<223> OTHER INFORMATION: n1 is c, g, u, a or t; n2 is u or t
<220> FEATURE:
<221> NAME/KEY: misc_feature
<222> LOCATION: (4)..(4)
<223> OTHER INFORMATION: n is u or t
<220> FEATURE:
<221> NAME/KEY: misc_feature
<222> LOCATION: (6)..(6)
<223> OTHER INFORMATION: n is u or t
<220> FEATURE:
<221> NAME/KEY: misc_feature
<222> LOCATION: (8)..(10)
<223> OTHER INFORMATION: n is c, g, u, a or t

<400> SEQUENCE: 28 nncngncnnn                                                        10

<210> SEQ ID NO 29
<211> LENGTH: 10
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, t or u
<220> FEATURE:
<221> NAME/KEY: misc_feature
<222> LOCATION: (4)..(5)
<223> OTHER INFORMATION: n is t or u
<220> FEATURE:
<221> NAME/KEY: misc_feature
<222> LOCATION: (8)..(10)
<223> OTHER INFORMATION: n is a, c, g, t or u

<400> SEQUENCE: 29 nacnngannn                                                        10

<210> SEQ ID NO 30
<211> LENGTH: 10
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(4)
<223> OTHER INFORMATION: n1 is a, c, g, t or u; n2, n3, n4 is u or t
<220> FEATURE:

```
<221> NAME/KEY: misc_feature
<222> LOCATION: (8)..(10)
<223> OTHER INFORMATION: n is a, c, g, t or u

<400> SEQUENCE: 30 nnnnccnnn                                                                 10

<210> SEQ ID NO 31
<211> LENGTH: 10
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, t or u
<220> FEATURE:
<221> NAME/KEY: misc_feature
<222> LOCATION: (8)..(10)
<223> OTHER INFORMATION: n is a, c, g, t or u

<400> SEQUENCE: 31 naccagcnnn                                                                10

<210> SEQ ID NO 32
<211> LENGTH: 10
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(3)
<223> OTHER INFORMATION: n1 is a, c, g, t or u; n2, n3 is u or t
<220> FEATURE:
<221> NAME/KEY: misc_feature
<222> LOCATION: (8)..(10)
<223> OTHER INFORMATION: n is a, c, g, t or u

<400> SEQUENCE: 32 nnnaccannn                                                                10

<210> SEQ ID NO 33
<211> LENGTH: 10
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, t or u
<220> FEATURE:
<221> NAME/KEY: misc_feature
<222> LOCATION: (3)..(3)
<223> OTHER INFORMATION: n is t or u
<220> FEATURE:
<221> NAME/KEY: misc_feature
<222> LOCATION: (6)..(10)
<223> OTHER INFORMATION: n3, n4 is t or u; n5-n7 is a, c, g, t or u

<400> SEQUENCE: 33 ncnagnnnnn                                                                10

<210> SEQ ID NO 34
<211> LENGTH: 10
<212> TYPE: DNA
<213> ORGANISM: Artificial Sequence
<220> FEATURE:
<223> OTHER INFORMATION: Completely synthesized in the lab.
```

```
<220> FEATURE:
<221> NAME/KEY: misc_feature
<222> LOCATION: (1)..(1)
<223> OTHER INFORMATION: n is a, c, g, t or u
<220> FEATURE:
<221> NAME/KEY: misc_feature
<222> LOCATION: (3)..(4)
<223> OTHER INFORMATION: n is t or u
<220> FEATURE:
<221> NAME/KEY: misc_feature
<222> LOCATION: (8)..(10)
<223> OTHER INFORMATION: n is a, c, g, t or u

<400> SEQUENCE: 34 ngnnagcnnn                                                              10

<210> SEQ ID NO 35
<211> LENGTH: 10
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, t or u
<220> FEATURE:
<221> NAME/KEY: misc_feature
<222> LOCATION: (3)..(4)
<223> OTHER INFORMATION: n is t or u
<220> FEATURE:
<221> NAME/KEY: misc_feature
<222> LOCATION: (8)..(10)
<223> OTHER INFORMATION: n is a, c, g, t or u

<400> SEQUENCE: 35 ngnnccgnnn                                                              10

<210> SEQ ID NO 36
<211> LENGTH: 10
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, t or u
<220> FEATURE:
<221> NAME/KEY: misc_feature
<222> LOCATION: (3)..(3)
<223> OTHER INFORMATION: n is t or u
<220> FEATURE:
<221> NAME/KEY: misc_feature
<222> LOCATION: (5)..(5)
<223> OTHER INFORMATION: n is t or u
<220> FEATURE:
<221> NAME/KEY: misc_feature
<222> LOCATION: (8)..(10)
<223> OTHER INFORMATION: n is a, c, g, t or u

<400> SEQUENCE: 36 ngncngannn                                                              10

<210> SEQ ID NO 37
<211> LENGTH: 10
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(2)
```

<223> OTHER INFORMATION: n1 is a, c, g, t or u; n2 is t or u
<220> FEATURE:
<221> NAME/KEY: misc_feature
<222> LOCATION: (5)..(5)
<223> OTHER INFORMATION: n is t or u
<220> FEATURE:
<221> NAME/KEY: misc_feature
<222> LOCATION: (7)..(10)
<223> OTHER INFORMATION: n4 is t or u; n5-n7 is a, c, g, t or u

<400> SEQUENCE: 37 nnccngnnnn                                                          10

<210> SEQ ID NO 38
<211> LENGTH: 10
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(2)
<223> OTHER INFORMATION: n1 is a, c, g, t or u; n2 is t or u
<220> FEATURE:
<221> NAME/KEY: misc_feature
<222> LOCATION: (5)..(5)
<223> OTHER INFORMATION: n is t or u
<220> FEATURE:
<221> NAME/KEY: misc_feature
<222> LOCATION: (8)..(10)
<223> OTHER INFORMATION: n is a, c, g, t or u

<400> SEQUENCE: 38 nnacngnnn                                                           10

<210> SEQ ID NO 39
<211> LENGTH: 10
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, t or u
<220> FEATURE:
<221> NAME/KEY: misc_feature
<222> LOCATION: (3)..(3)
<223> OTHER INFORMATION: n is t or u
<220> FEATURE:
<221> NAME/KEY: misc_feature
<222> LOCATION: (5)..(5)
<223> OTHER INFORMATION: n is t or u
<220> FEATURE:
<221> NAME/KEY: misc_feature
<222> LOCATION: (7)..(10)
<223> OTHER INFORMATION: n4 is t or u; n5-n7 is a, c, g, t or u

<400> SEQUENCE: 39 nancngnnnn                                                          10

<210> SEQ ID NO 40
<211> LENGTH: 10
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(3)
<223> OTHER INFORMATION: n1 is a, c, g, t or u; n2-n3 is t or u
<220> FEATURE:
<221> NAME/KEY: misc_feature
<222> LOCATION: (8)..(10)
<223> OTHER INFORMATION: n is a, c, g, t or u

<400> SEQUENCE: 40 nnngcagnnn                                                                  10

<210> SEQ ID NO 41
<211> LENGTH: 10
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(2)
<223> OTHER INFORMATION: n1 is a, c, g, t or u; n2 is t or u
<220> FEATURE:
<221> NAME/KEY: misc_feature
<222> LOCATION: (5)..(5)
<223> OTHER INFORMATION: n is t or u
<220> FEATURE:
<221> NAME/KEY: misc_feature
<222> LOCATION: (8)..(10)
<223> OTHER INFORMATION: n is a, c, g, t or u

<400> SEQUENCE: 41 nnccnggnnn                                                                  10

<210> SEQ ID NO 42
<211> LENGTH: 10
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, t or u
<220> FEATURE:
<221> NAME/KEY: misc_feature
<222> LOCATION: (4)..(4)
<223> OTHER INFORMATION: n is t or u
<220> FEATURE:
<221> NAME/KEY: misc_feature
<222> LOCATION: (8)..(10)
<223> OTHER INFORMATION: n is a, c, g, t or u

<400> SEQUENCE: 42 nacngacnnn                                                                  10

<210> SEQ ID NO 43
<211> LENGTH: 10
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, t or u
<220> FEATURE:
<221> NAME/KEY: misc_feature
<222> LOCATION: (8)..(10)
<223> OTHER INFORMATION: n is a, c, g, t or u

<400> SEQUENCE: 43 nccagccnnn                                                                  10

<210> SEQ ID NO 44
<211> LENGTH: 10
<212> TYPE: DNA

```
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(2)
<223> OTHER INFORMATION: n1 is a, c, g, t or u; n2 is t or u
<220> FEATURE:
<221> NAME/KEY: misc_feature
<222> LOCATION: (8)..(10)
<223> OTHER INFORMATION: n is a, c, g, t or u

<400> SEQUENCE: 44 nnacaccnnn                                                              10

<210> SEQ ID NO 45
<211> LENGTH: 10
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, t or u
<220> FEATURE:
<221> NAME/KEY: misc_feature
<222> LOCATION: (5)..(5)
<223> OTHER INFORMATION: n is t or u
<220> FEATURE:
<221> NAME/KEY: misc_feature
<222> LOCATION: (8)..(10)
<223> OTHER INFORMATION: n is a, c, g, t or u

<400> SEQUENCE: 45 naagnacnnn                                                              10

<210> SEQ ID NO 46
<211> LENGTH: 10
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(2)
<223> OTHER INFORMATION: n1 is a, c, g, t or u; n2 is t or u
<220> FEATURE:
<221> NAME/KEY: misc_feature
<222> LOCATION: (6)..(6)
<223> OTHER INFORMATION: n is t or u
<220> FEATURE:
<221> NAME/KEY: misc_feature
<222> LOCATION: (8)..(10)
<223> OTHER INFORMATION: n is a, c, g, t or u

<400> SEQUENCE: 46 nnaagnannn                                                              10

<210> SEQ ID NO 47
<211> LENGTH: 10
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, t or u
<220> FEATURE:
<221> NAME/KEY: misc_feature
<222> LOCATION: (4)..(4)
<223> OTHER INFORMATION: n is t or u
```

```
<220> FEATURE:
<221> NAME/KEY: misc_feature
<222> LOCATION: (8)..(10)
<223> OTHER INFORMATION: n is a, c, g, t or u

<400> SEQUENCE: 47 nccnggcnnn                                                                10

<210> SEQ ID NO 48
<211> LENGTH: 10
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, t or u
<220> FEATURE:
<221> NAME/KEY: misc_feature
<222> LOCATION: (5)..(5)
<223> OTHER INFORMATION: n is t or u
<220> FEATURE:
<221> NAME/KEY: misc_feature
<222> LOCATION: (8)..(10)
<223> OTHER INFORMATION: n is a, c, g, t or u

<400> SEQUENCE: 48 naccnggnnn                                                                10

<210> SEQ ID NO 49
<211> LENGTH: 10
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, t or u
<220> FEATURE:
<221> NAME/KEY: misc_feature
<222> LOCATION: (7)..(10)
<223> OTHER INFORMATION: n2 is u or t; n3-n5 is a, c, g, t or u

<400> SEQUENCE: 49 ngcaggnnnn                                                                10

<210> SEQ ID NO 50
<211> LENGTH: 10
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(2)
<223> OTHER INFORMATION: n1 is a, c, g, t or u; n2 is t or u
<220> FEATURE:
<221> NAME/KEY: misc_feature
<222> LOCATION: (8)..(10)
<223> OTHER INFORMATION: n is a, c, g, t or u

<400> SEQUENCE: 50 nngcaggnnn                                                                10

<210> SEQ ID NO 51
<211> LENGTH: 10
<212> TYPE: DNA
<213> ORGANISM: Artificial Sequence
<220> FEATURE:
```

```
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, t or u
<220> FEATURE:
<221> NAME/KEY: misc_feature
<222> LOCATION: (5)..(6)
<223> OTHER INFORMATION: n is t or u
<220> FEATURE:
<221> NAME/KEY: misc_feature
<222> LOCATION: (8)..(10)
<223> OTHER INFORMATION: n is a, c, g, t or u

<400> SEQUENCE: 51 ngacnngnnn                                                              10

<210> SEQ ID NO 52
<211> LENGTH: 10
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, t or u
<220> FEATURE:
<221> NAME/KEY: misc_feature
<222> LOCATION: (4)..(4)
<223> OTHER INFORMATION: n is t or u
<220> FEATURE:
<221> NAME/KEY: misc_feature
<222> LOCATION: (8)..(10)
<223> OTHER INFORMATION: n is a, c, g, t or u

<400> SEQUENCE: 52 ngangccnnn                                                              10

<210> SEQ ID NO 53
<211> LENGTH: 10
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(2)
<223> OTHER INFORMATION: n1 is a, c, g, t or u; n2 is t or u
<220> FEATURE:
<221> NAME/KEY: misc_feature
<222> LOCATION: (8)..(10)
<223> OTHER INFORMATION: n is a, c, g, t or u

<400> SEQUENCE: 53 nnaaggcnnn                                                              10

<210> SEQ ID NO 54
<211> LENGTH: 10
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(2)
<223> OTHER INFORMATION: n1 is a, c, g, t or u; n2 is t or u
<220> FEATURE:
<221> NAME/KEY: misc_feature
<222> LOCATION: (5)..(5)
<223> OTHER INFORMATION: n is t or u
<220> FEATURE:
<221> NAME/KEY: misc_feature
```

```
<222> LOCATION: (8)..(10)
<223> OTHER INFORMATION: n is a, c, g, t or u

<400> SEQUENCE: 54 nnganagnnn                                                              10

<210> SEQ ID NO 55
<211> LENGTH: 10
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(3)
<223> OTHER INFORMATION: n1 is a, c, g, t or u; n2-n3 is t or u
<220> FEATURE:
<221> NAME/KEY: misc_feature
<222> LOCATION: (8)..(10)
<223> OTHER INFORMATION: n is a, c, g, t or u

<400> SEQUENCE: 55 nnnagccnnn                                                              10

<210> SEQ ID NO 56
<211> LENGTH: 10
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(2)
<223> OTHER INFORMATION: n1 is a, c, g, t or u; n2 is t or u
<220> FEATURE:
<221> NAME/KEY: misc_feature
<222> LOCATION: (4)..(6)
<223> OTHER INFORMATION: n is t or u
<220> FEATURE:
<221> NAME/KEY: misc_feature
<222> LOCATION: (8)..(10)
<223> OTHER INFORMATION: n is a, c, g, t or u

<400> SEQUENCE: 56 nngnnnannn                                                              10

<210> SEQ ID NO 57
<211> LENGTH: 10
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(3)
<223> OTHER INFORMATION: n1 is a, c, g, t or u; n2-n3 is t or u
<220> FEATURE:
<221> NAME/KEY: misc_feature
<222> LOCATION: (8)..(10)
<223> OTHER INFORMATION: n is a, c, g, t or u

<400> SEQUENCE: 57 nnncggcnnn                                                              10

<210> SEQ ID NO 58
<211> LENGTH: 10
<212> TYPE: DNA
<213> ORGANISM: Artificial Sequence
<220> FEATURE:
<223> OTHER INFORMATION: Completely synthesized in the lab.
<220> FEATURE:
```

```
<221> NAME/KEY: misc_feature
<222> LOCATION: (1)..(2)
<223> OTHER INFORMATION: n1 is a, c, g, t or u; n2 is t or u
<220> FEATURE:
<221> NAME/KEY: misc_feature
<222> LOCATION: (5)..(5)
<223> OTHER INFORMATION: n is t or u
<220> FEATURE:
<221> NAME/KEY: misc_feature
<222> LOCATION: (7)..(10)
<223> OTHER INFORMATION: n4 is t or u; n5-n7 is a, c, g, t or u

<400> SEQUENCE: 58 nnacngnnnn                                                          10

<210> SEQ ID NO 59
<211> LENGTH: 10
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(2)
<223> OTHER INFORMATION: n1 is a, c, g, t or u; n2 is t or u
<220> FEATURE:
<221> NAME/KEY: misc_feature
<222> LOCATION: (5)..(5)
<223> OTHER INFORMATION: n is t or u
<220> FEATURE:
<221> NAME/KEY: misc_feature
<222> LOCATION: (8)..(10)
<223> OTHER INFORMATION: n is a, c, g, t or u

<400> SEQUENCE: 59 nnacngannn                                                          10

<210> SEQ ID NO 60
<211> LENGTH: 10
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, t or u
<220> FEATURE:
<221> NAME/KEY: misc_feature
<222> LOCATION: (3)..(3)
<223> OTHER INFORMATION: n is t or u
<220> FEATURE:
<221> NAME/KEY: misc_feature
<222> LOCATION: (5)..(5)
<223> OTHER INFORMATION: n is t or u
<220> FEATURE:
<221> NAME/KEY: misc_feature
<222> LOCATION: (7)..(10)
<223> OTHER INFORMATION: n4 is t or u; n5-n7 is a, c, g, t or u

<400> SEQUENCE: 60 ngngngnnnn                                                          10

<210> SEQ ID NO 61
<211> LENGTH: 10
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, t or u
```

```
<220> FEATURE:
<221> NAME/KEY: misc_feature
<222> LOCATION: (3)..(3)
<223> OTHER INFORMATION: n is t or u
<220> FEATURE:
<221> NAME/KEY: misc_feature
<222> LOCATION: (5)..(5)
<223> OTHER INFORMATION: n is t or u
<220> FEATURE:
<221> NAME/KEY: misc_feature
<222> LOCATION: (8)..(10)
<223> OTHER INFORMATION: n is a, c, g, t or u

<400> SEQUENCE: 61 nangnacnnn                                                            10

<210> SEQ ID NO 62
<211> LENGTH: 10
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(2)
<223> OTHER INFORMATION: n is a, c, g, t or u
<220> FEATURE:
<221> NAME/KEY: misc_feature
<222> LOCATION: (4)..(4)
<223> OTHER INFORMATION: n is t or u
<220> FEATURE:
<221> NAME/KEY: misc_feature
<222> LOCATION: (7)..(10)
<223> OTHER INFORMATION: n4 is t or u; n5-n7 is a, c, g, t or u

<400> SEQUENCE: 62 nnancannnn                                                            10

<210> SEQ ID NO 63
<211> LENGTH: 10
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, t or u
<220> FEATURE:
<221> NAME/KEY: misc_feature
<222> LOCATION: (4)..(4)
<223> OTHER INFORMATION: n is t or u
<220> FEATURE:
<221> NAME/KEY: misc_feature
<222> LOCATION: (8)..(10)
<223> OTHER INFORMATION: n is a, c, g, t or u

<400> SEQUENCE: 63 nganagannn                                                            10

<210> SEQ ID NO 64
<211> LENGTH: 19
<212> TYPE: RNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (8)..(19)
```

```
<223> OTHER INFORMATION: n is a, c, g, or u

<400> SEQUENCE: 64
nucugucnnn nnnnnnnnn                                                  19

<210> SEQ ID NO 65
<211> LENGTH: 19
<212> TYPE: RNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (8)..(19)
<223> OTHER INFORMATION: n is a, c, g, or u

<400> SEQUENCE: 65
nacuugannn nnnnnnnnn                                                  19

<210> SEQ ID NO 66
<211> LENGTH: 19
<212> TYPE: RNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (8)..(19)
<223> OTHER INFORMATION: n is a, c, g, or u

<400> SEQUENCE: 66
nuuucccnnn nnnnnnnnn                                                  19

<210> SEQ ID NO 67
<211> LENGTH: 19
<212> TYPE: RNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (8)..(19)
<223> OTHER INFORMATION: n is a, c, g, or u

<400> SEQUENCE: 67
naccagcnnn nnnnnnnnn                                                  19

<210> SEQ ID NO 68
<211> LENGTH: 19
<212> TYPE: RNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
```

```
<222> LOCATION: (8)..(19)
<223> OTHER INFORMATION: n is a, c, g, or u

<400> SEQUENCE: 68
nuuaccannn nnnnnnnnn                                                    19

<210> SEQ ID NO 69
<211> LENGTH: 19
<212> TYPE: RNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (8)..(19)
<223> OTHER INFORMATION: n is a, c, g, or u

<400> SEQUENCE: 69
ncuaguunnn nnnnnnnnn                                                    19

<210> SEQ ID NO 70
<211> LENGTH: 19
<212> TYPE: RNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (8)..(19)
<223> OTHER INFORMATION: n is a, c, g, or u

<400> SEQUENCE: 70
nguuagcnnn nnnnnnnnn                                                    19

<210> SEQ ID NO 71
<211> LENGTH: 19
<212> TYPE: RNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (8)..(19)
<223> OTHER INFORMATION: n is a, c, g, or u

<400> SEQUENCE: 71
nguuccgnnn nnnnnnnnn                                                    19

<210> SEQ ID NO 72
<211> LENGTH: 19
<212> TYPE: RNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or u
<220> FEATURE:
```

```
<221> NAME/KEY: misc_feature
<222> LOCATION: (8)..(19)
<223> OTHER INFORMATION: n is a, c, g, or u

<400> SEQUENCE: 72
ngucugannn nnnnnnnnn                                                    19

<210> SEQ ID NO 73
<211> LENGTH: 19
<212> TYPE: RNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (8)..(19)
<223> OTHER INFORMATION: n is a, c, g, or u

<400> SEQUENCE: 73
nuccugunnn nnnnnnnnn                                                    19

<210> SEQ ID NO 74
<211> LENGTH: 19
<212> TYPE: RNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (8)..(19)
<223> OTHER INFORMATION: n is a, c, g, or u

<400> SEQUENCE: 74
nuacuggnnn nnnnnnnnn                                                    19

<210> SEQ ID NO 75
<211> LENGTH: 19
<212> TYPE: RNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (8)..(19)
<223> OTHER INFORMATION: n is a, c, g, or u

<400> SEQUENCE: 75
naucugunnn nnnnnnnnn                                                    19

<210> SEQ ID NO 76
<211> LENGTH: 19
<212> TYPE: RNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or u
```

```
<220> FEATURE:
<221> NAME/KEY: misc_feature
<222> LOCATION: (8)..(19)
<223> OTHER INFORMATION: n is a, c, g, or u

<400> SEQUENCE: 76
nuugcagnnn nnnnnnnnn                                                    19

<210> SEQ ID NO 77
<211> LENGTH: 19
<212> TYPE: RNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (8)..(19)
<223> OTHER INFORMATION: n is a, c, g, or u

<400> SEQUENCE: 77
nuccuggnnn nnnnnnnnn                                                    19

<210> SEQ ID NO 78
<211> LENGTH: 19
<212> TYPE: RNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (8)..(19)
<223> OTHER INFORMATION: n is a, c, g, or u

<400> SEQUENCE: 78
nacugacnnn nnnnnnnnn                                                    19

<210> SEQ ID NO 79
<211> LENGTH: 19
<212> TYPE: RNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (8)..(19)
<223> OTHER INFORMATION: n is a, c, g, or u

<400> SEQUENCE: 79
nccagccnnn nnnnnnnnn                                                    19

<210> SEQ ID NO 80
<211> LENGTH: 19
<212> TYPE: RNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
```

<223> OTHER INFORMATION: n is a, c, g, or u
<220> FEATURE:
<221> NAME/KEY: misc_feature
<222> LOCATION: (8)..(19)
<223> OTHER INFORMATION: n is a, c, g, or u

<400> SEQUENCE: 80
nuacaccnnn nnnnnnnnn                                                      19

<210> SEQ ID NO 81
<211> LENGTH: 19
<212> TYPE: RNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (8)..(19)
<223> OTHER INFORMATION: n is a, c, g, or u

<400> SEQUENCE: 81
naaguacnnn nnnnnnnnn                                                      19

<210> SEQ ID NO 82
<211> LENGTH: 19
<212> TYPE: RNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (8)..(19)
<223> OTHER INFORMATION: n is a, c, g, or u

<400> SEQUENCE: 82
nuaaguannn nnnnnnnnn                                                      19

<210> SEQ ID NO 83
<211> LENGTH: 19
<212> TYPE: RNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (8)..(19)
<223> OTHER INFORMATION: n is a, c, g, or u

<400> SEQUENCE: 83
nccuggcnnn nnnnnnnnn                                                      19

<210> SEQ ID NO 84
<211> LENGTH: 19
<212> TYPE: RNA
<213> ORGANISM: Artificial Sequence
<220> FEATURE:
<223> OTHER INFORMATION: Completely synthesized in the lab.
<220> FEATURE:
<221> NAME/KEY: misc_feature

```
<222> LOCATION: (1)..(1)
<223> OTHER INFORMATION: n is a, c, g, or u
<220> FEATURE:
<221> NAME/KEY: misc_feature
<222> LOCATION: (8)..(19)
<223> OTHER INFORMATION: n is a, c, g, or u

<400> SEQUENCE: 84
naccuggnnn nnnnnnnn                                                  19

<210> SEQ ID NO 85
<211> LENGTH: 19
<212> TYPE: RNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (8)..(19)
<223> OTHER INFORMATION: n is a, c, g, or u

<400> SEQUENCE: 85
ngcaggunnn nnnnnnnn                                                  19

<210> SEQ ID NO 86
<211> LENGTH: 19
<212> TYPE: RNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (8)..(19)
<223> OTHER INFORMATION: n is a, c, g, or u

<400> SEQUENCE: 86
nugcaggnnn nnnnnnnn                                                  19

<210> SEQ ID NO 87
<211> LENGTH: 19
<212> TYPE: RNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (8)..(19)
<223> OTHER INFORMATION: n is a, c, g, or u

<400> SEQUENCE: 87
ngacuugnnn nnnnnnnn                                                  19

<210> SEQ ID NO 88
<211> LENGTH: 19
<212> TYPE: RNA
<213> ORGANISM: Artificial Sequence
<220> FEATURE:
<223> OTHER INFORMATION: Completely synthesized in the lab.
<220> FEATURE:
```

```
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (8)..(19)
<223> OTHER INFORMATION: n is a, c, g, or u

<400> SEQUENCE: 88
ngaugccnnn nnnnnnnnn                                                     19

<210> SEQ ID NO 89
<211> LENGTH: 19
<212> TYPE: RNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (8)..(19)
<223> OTHER INFORMATION: n is a, c, g, or u

<400> SEQUENCE: 89
nuaaggcnnn nnnnnnnnn                                                     19

<210> SEQ ID NO 90
<211> LENGTH: 19
<212> TYPE: RNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (8)..(19)
<223> OTHER INFORMATION: n is a, c, g, or u

<400> SEQUENCE: 90
nugauagnnn nnnnnnnnn                                                     19

<210> SEQ ID NO 91
<211> LENGTH: 19
<212> TYPE: RNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (8)..(19)
<223> OTHER INFORMATION: n is a, c, g, or u

<400> SEQUENCE: 91
nuuagccnnn nnnnnnnnn                                                     19

<210> SEQ ID NO 92
<211> LENGTH: 19
<212> TYPE: RNA
<213> ORGANISM: Artificial Sequence
<220> FEATURE:
<223> OTHER INFORMATION: Completely synthesized in the lab.
```

```
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (8)..(19)
<223> OTHER INFORMATION: n is a, c, g, or u

<400> SEQUENCE: 92
nuguuuannn nnnnnnnnn                                              19

<210> SEQ ID NO 93
<211> LENGTH: 19
<212> TYPE: RNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (8)..(19)
<223> OTHER INFORMATION: n is a, c, g, or u

<400> SEQUENCE: 93
nuucggcnnn nnnnnnnnn                                              19

<210> SEQ ID NO 94
<211> LENGTH: 19
<212> TYPE: RNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (8)..(19)
<223> OTHER INFORMATION: n is a, c, g, or u

<400> SEQUENCE: 94
nuacugunnn nnnnnnnnn                                              19

<210> SEQ ID NO 95
<211> LENGTH: 19
<212> TYPE: RNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (8)..(19)
<223> OTHER INFORMATION: n is a, c, g, or u

<400> SEQUENCE: 95
nuacugannn nnnnnnnnn                                              19

<210> SEQ ID NO 96
<211> LENGTH: 19
<212> TYPE: RNA
<213> ORGANISM: Artificial Sequence
<220> FEATURE:
```

```
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (8)..(19)
<223> OTHER INFORMATION: n is a, c, g, or u

<400> SEQUENCE: 96
ngugugunnn nnnnnnnnn                                              19

<210> SEQ ID NO 97
<211> LENGTH: 19
<212> TYPE: RNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (8)..(19)
<223> OTHER INFORMATION: n is a, c, g, or u

<400> SEQUENCE: 97
nauguacnnn nnnnnnnnn                                              19

<210> SEQ ID NO 98
<211> LENGTH: 19
<212> TYPE: RNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (8)..(19)
<223> OTHER INFORMATION: n is a, c, g, or u

<400> SEQUENCE: 98
nuaucaunnn nnnnnnnnn                                              19

<210> SEQ ID NO 99
<211> LENGTH: 19
<212> TYPE: RNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (8)..(19)
<223> OTHER INFORMATION: n is a, c, g, or u

<400> SEQUENCE: 99
ngauagannn nnnnnnnnn                                              19

<210> SEQ ID NO 100
<211> LENGTH: 19
<212> TYPE: DNA
<213> ORGANISM: Artificial Sequence
```

```
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (8)..(19)
<223> OTHER INFORMATION: n is a, c, g, or t

<400> SEQUENCE: 100
ntctgtcnnn nnnnnnnnn                                                    19

<210> SEQ ID NO 101
<211> LENGTH: 19
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (8)..(19)
<223> OTHER INFORMATION: n is a, c, g, or t

<400> SEQUENCE: 101
nacttgannn nnnnnnnnn                                                    19

<210> SEQ ID NO 102
<211> LENGTH: 19
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (8)..(19)
<223> OTHER INFORMATION: n is a, c, g, or t

<400> SEQUENCE: 102
ntttcccnnn nnnnnnnnn                                                    19

<210> SEQ ID NO 103
<211> LENGTH: 19
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (8)..(19)
<223> OTHER INFORMATION: n is a, c, g, or t

<400> SEQUENCE: 103
nttaccannn nnnnnnnnn                                                    19

<210> SEQ ID NO 104
<211> LENGTH: 19
<212> TYPE: DNA
```

```
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (8)..(19)
<223> OTHER INFORMATION: n is a, c, g, or t

<400> SEQUENCE: 104
nctagttnnn nnnnnnnnn                                              19

<210> SEQ ID NO 105
<211> LENGTH: 19
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (8)..(19)
<223> OTHER INFORMATION: n is a, c, g, or t

<400> SEQUENCE: 105
ngttagcnnn nnnnnnnnn                                              19

<210> SEQ ID NO 106
<211> LENGTH: 19
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (8)..(19)
<223> OTHER INFORMATION: n is a, c, g, or t

<400> SEQUENCE: 106
ngttccgnnn nnnnnnnnn                                              19

<210> SEQ ID NO 107
<211> LENGTH: 19
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (8)..(19)
<223> OTHER INFORMATION: n is a, c, g, or t

<400> SEQUENCE: 107
ngtctgannn nnnnnnnnn                                              19

<210> SEQ ID NO 108
<211> LENGTH: 19
```

```
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (8)..(19)
<223> OTHER INFORMATION: n is a, c, g, or t

<400> SEQUENCE: 108
ntcctgtnnn nnnnnnnn                                              19

<210> SEQ ID NO 109
<211> LENGTH: 19
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (8)..(19)
<223> OTHER INFORMATION: n is a, c, g, or t

<400> SEQUENCE: 109
ntactggnnn nnnnnnnn                                              19

<210> SEQ ID NO 110
<211> LENGTH: 19
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (8)..(19)
<223> OTHER INFORMATION: n is a, c, g, or t

<400> SEQUENCE: 110
natctgtnnn nnnnnnnn                                              19

<210> SEQ ID NO 111
<211> LENGTH: 19
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (8)..(19)
<223> OTHER INFORMATION: n is a, c, g, or t

<400> SEQUENCE: 111
nttgcagnnn nnnnnnnn                                              19

<210> SEQ ID NO 112
```

```
<211> LENGTH: 19
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (8)..(19)
<223> OTHER INFORMATION: n is a, c, g, or t

<400> SEQUENCE: 112
ntcctggnnn nnnnnnnn                                                   19

<210> SEQ ID NO 113
<211> LENGTH: 19
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (8)..(19)
<223> OTHER INFORMATION: n is a, c, g, or t

<400> SEQUENCE: 113
nactgacnnn nnnnnnnn                                                   19

<210> SEQ ID NO 114
<211> LENGTH: 19
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (8)..(19)
<223> OTHER INFORMATION: n is a, c, g, or t

<400> SEQUENCE: 114
nccagccnnn nnnnnnnn                                                   19

<210> SEQ ID NO 115
<211> LENGTH: 19
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (8)..(19)
<223> OTHER INFORMATION: n is a, c, g, or t

<400> SEQUENCE: 115
ntacaccnnn nnnnnnnn                                                   19
```

```
<210> SEQ ID NO 116
<211> LENGTH: 19
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (8)..(19)
<223> OTHER INFORMATION: n is a, c, g, or t

<400> SEQUENCE: 116
naagtacnnn nnnnnnnnn                                                    19

<210> SEQ ID NO 117
<211> LENGTH: 19
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (8)..(19)
<223> OTHER INFORMATION: n is a, c, g, or t

<400> SEQUENCE: 117
ntaagtannn nnnnnnnnn                                                    19

<210> SEQ ID NO 118
<211> LENGTH: 19
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (8)..(19)
<223> OTHER INFORMATION: n is a, c, g, or t

<400> SEQUENCE: 118
ncctggcnnn nnnnnnnnn                                                    19

<210> SEQ ID NO 119
<211> LENGTH: 19
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (8)..(19)
<223> OTHER INFORMATION: n is a, c, g, or t

<400> SEQUENCE: 119
nacctggnnn nnnnnnnnn                                                    19
```

```
<210> SEQ ID NO 120
<211> LENGTH: 19
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (8)..(19)
<223> OTHER INFORMATION: n is a, c, g, or t

<400> SEQUENCE: 120
ngcaggtnnn nnnnnnnn                                                    19

<210> SEQ ID NO 121
<211> LENGTH: 19
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (8)..(19)
<223> OTHER INFORMATION: n is a, c, g, or t

<400> SEQUENCE: 121
ntgcaggnnn nnnnnnnn                                                    19

<210> SEQ ID NO 122
<211> LENGTH: 19
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (8)..(19)
<223> OTHER INFORMATION: n is a, c, g, or t

<400> SEQUENCE: 122
ngacttgnnn nnnnnnnn                                                    19

<210> SEQ ID NO 123
<211> LENGTH: 19
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (8)..(19)
<223> OTHER INFORMATION: n is a, c, g, or t

<400> SEQUENCE: 123
ngatgccnnn nnnnnnnn                                                    19
```

<210> SEQ ID NO 124
<211> LENGTH: 19
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (8)..(19)
<223> OTHER INFORMATION: n is a, c, g, or t

<400> SEQUENCE: 124
ntaaggcnnn nnnnnnnnn                                               19

<210> SEQ ID NO 125
<211> LENGTH: 19
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (8)..(19)
<223> OTHER INFORMATION: n is a, c, g, or t

<400> SEQUENCE: 125
ntgatagnnn nnnnnnnnn                                               19

<210> SEQ ID NO 126
<211> LENGTH: 19
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (8)..(19)
<223> OTHER INFORMATION: n is a, c, g, or t

<400> SEQUENCE: 126
nttagccnnn nnnnnnnnn                                               19

<210> SEQ ID NO 127
<211> LENGTH: 19
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (8)..(19)
<223> OTHER INFORMATION: n is a, c, g, or t

<400> SEQUENCE: 127
ntgtttannn nnnnnnnnn                                                    19

<210> SEQ ID NO 128
<211> LENGTH: 19
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (8)..(19)
<223> OTHER INFORMATION: n is a, c, g, or t

<400> SEQUENCE: 128
nttcggcnnn nnnnnnnnn                                                    19

<210> SEQ ID NO 129
<211> LENGTH: 19
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (8)..(19)
<223> OTHER INFORMATION: n is a, c, g, or t

<400> SEQUENCE: 129
ntactgtnnn nnnnnnnnn                                                    19

<210> SEQ ID NO 130
<211> LENGTH: 19
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (8)..(19)
<223> OTHER INFORMATION: n is a, c, g, or t

<400> SEQUENCE: 130
ntactgannn nnnnnnnnn                                                    19

<210> SEQ ID NO 131
<211> LENGTH: 19
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (8)..(19)
<223> OTHER INFORMATION: n is a, c, g, or t

<400> SEQUENCE: 131

-continued ngtgtgtnnn nnnnnnnnn                                             19

<210> SEQ ID NO 132
<211> LENGTH: 19
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (8)..(19)
<223> OTHER INFORMATION: n is a, c, g, or t

<400> SEQUENCE: 132
natgtacnnn nnnnnnnnn                                             19

<210> SEQ ID NO 133
<211> LENGTH: 19
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (8)..(19)
<223> OTHER INFORMATION: n is a, c, g, or t

<400> SEQUENCE: 133
ntatcatnnn nnnnnnnnn                                             19

<210> SEQ ID NO 134
<211> LENGTH: 19
<212> TYPE: DNA
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (8)..(19)
<223> OTHER INFORMATION: n is a, c, g, or t

<400> SEQUENCE: 134
ngatagannn nnnnnnnnn                                             19